United States Patent
O'Keefe

(10) Patent No.: US 9,107,892 B2
(45) Date of Patent: Aug. 18, 2015

(54) IDENTIFICATION OF A NOVEL RETROVIRUS IN PATIENTS WITH BENIGN PROSTATIC HYPERPLASIA

(75) Inventor: Denise S. O'Keefe, Wexford, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 592 days.

(21) Appl. No.: 13/282,888

(22) Filed: Oct. 27, 2011

(65) Prior Publication Data

US 2012/0107338 A1    May 3, 2012

Related U.S. Application Data

(60) Provisional application No. 61/407,846, filed on Oct. 28, 2010.

(51) Int. Cl.
| | | |
|---|---|---|
| A61K 39/21 | (2006.01) | |
| C12Q 1/70 | (2006.01) | |
| C12N 7/00 | (2006.01) | |
| C12Q 1/68 | (2006.01) | |
| C12Q 1/00 | (2006.01) | |
| A61K 39/00 | (2006.01) | |

(52) U.S. Cl.
CPC . *A61K 39/21* (2013.01); *C12N 7/00* (2013.01); *C12Q 1/701* (2013.01); *A61K 2039/545* (2013.01); *C12N 2740/13011* (2013.01); *C12N 2740/13021* (2013.01); *C12N 2740/13022* (2013.01); *C12N 2740/13034* (2013.01); *C12Q 1/00* (2013.01); *C12Q 1/686* (2013.01); *C12Q 1/6844* (2013.01); *C12Q 1/6846* (2013.01)

(58) Field of Classification Search
None
See application file for complete search history.

(56) References Cited

U.S. PATENT DOCUMENTS

| | | |
|---|---|---|
| 2004/0126762 A1 | 7/2004 | Morris et al. |
| 2004/0166490 A1 | 8/2004 | Morris et al. |
| 2004/0170982 A1 | 9/2004 | Morris et al. |
| 2004/0180344 A1 | 9/2004 | Morris et al. |
| 2004/0197778 A1 | 10/2004 | Morris et al. |
| 2008/0274467 A1 | 11/2008 | Morris et al. |
| 2009/0214542 A1 | 8/2009 | Morris et al. |
| 2009/0214546 A1 | 8/2009 | Morris et al. |
| 2009/0215711 A1 | 8/2009 | Morris et al. |
| 2009/0221437 A1 | 9/2009 | Harkin et al. |

FOREIGN PATENT DOCUMENTS

WO    WO 2006/110589    * 10/2006

OTHER PUBLICATIONS

Sabaliauskaite, et al. 2011; XMRV complete proviral genome, isolate 5-162. GenBank: FR672816.1.*
Schlaberg et al., "XMRV is present in malignant prostatic epithelium and is associated with prostate cancer, especially high-grade tumors," Proc. Natl. Acad. Sci. USA vol. 106, No. 38, pp. 16351-16356, 2009.
Urisman et al., "Identification of a Novel Gammaretrovirus in Prostate Tumors of Patients Homozygous for R462Q RNASEL Variant," PLoS Pathogens, vol. 2, No. 3, e25, 2006 (15 pages).

* cited by examiner

Primary Examiner — Zachariah Lucas
Assistant Examiner — Stuart W Snyder
(74) Attorney, Agent, or Firm — Klarquist Sparkman, LLP

(57) ABSTRACT

Methods for producing an immune response to a benign prostatic hyperplasia (BPH) virus are disclosed herein. In several examples, the immune response is a protective immune response. In additional embodiments, methods are disclosed for inhibiting an infection with BPH virus, or treating an infection with BPH virus. Also disclosed are methods for detecting presence of BPH virus in a subject. The methods include detecting the presence of one or more BPH virus polynucleotides or polypeptides in a sample from the subject, or presence of at least one antibody that specifically binds to a BPH virus polypeptide.

4 Claims, 18 Drawing Sheets

FIG 2

```
GB339_BV1              ---------------CCTGGGAGGGTCTCCTCAGATTGATTGACTACCCAC
GB620D_BV1             ----------------TGGGAGGGTCTCCTCAGATTGATTGACTACCCAC
TP08-300512_BV1        ---------------CCTGGGAGGGTCTCCTCAGATTGATTGACTACCCAC
GB620B_BV1             ---------------CCTGGGAGGGTCTCCTCAGATTGATTGACTACCCAC
TP08-300036_BV1        --------------CCTGGGAGGG-CTCCTCAGATTGATTGACTACCCAC
GB209_BV1              ---------------CCTGGGAGGGTCTCCTCAGATTGATTGACTACCCAC
GB620A_BV1             ---------------CCTGGGAGGGTCTCCTCAGATTGATTGACTACCCAC
TP08-300606_BV1        ---------------CCTGGGAGGGTCTCCTCAGATTGATTGACTACCCAC
GB250_BV1              ---------------CCTGGGAGGGTCTCCTCAGATTGATTGACTACCCAC
BP8-1_BV1              ---------------CCTGGGAGGGTCTCCTCAGATTGATTGACTACCCAC
HB106R_BV1             ---------------CCTGGGAGGGTCTCCTCAGATTGATTGACTACCCAC
NPMYY_T7_BV1           ---------------CCTGGGAGGGTCTCCTCAGATTGATTGACTACCCAC
NPMYY_SP6_BV1          ---------------CCTGGGAGGGTCTCCTCAGATTGATTGACTACCCAC
GB338_BV1              ---------------CCTGGGAGGGTCTCCTCAGATTGATTGACTACCCAC
1390XNOR_BV1           ---------------CCTGGGAGGGTCTCCTCAGATTGATTGACTACCCAC
HB068A_BV1             ---------------CCTGGGAGGGTCTCCTCAGATTGATTGACTACCCAC
HB068C_BV1             ---------------CCTGGGAGGGTCTCCTCAGATTGATTGACTACCCAC
mouse_polytropic_51    ---GTCTGCTGGTCCTGGGAGGGTCTCCTGAATGATTGACTACCTGC
GB529_BV1              ---------------CCTGGGAGGGTCTCCTGAATTGATTGACTGCCCAC
TP08-300192_BV2        ---------------CCTGGGAGGGTCTCCTGAATTGATTGACTACCTGC
GB534_BV1              ---------------CCTGGGAGGGTCTCCTGAATTGATTGACTGCCCGC
GB620C_BV1             ---------------CCTGGGAGGGTCTCCTGAATTGATTGACTGCCCGC
HB063B_BV1             ---------------GTCTCCTCAGATTGATTGACTGCCCGC
XMRV_VP62              --GCTCGCTGTCCTGGGAGGGTCTCCTGAGATTGATTGACTACCTGC
TP08-300076A_BV2       ---------------CCTGGGAGGGTCTCCTGAATTGATTGACCACCCGC
TP08-300076C_BV2       ---------------CCTGGGAGGGTCTCCTGAATTGATTGACCACCCGC
TP08-300076B_BV2       ---------------CCTGGGAGGGTCTCCTGAATTGATTGACCACCCGT
TP08-300685B_BV2       ---------------CCTGGGAGGGTCTCCTAGATTGATTGACCACCCGC
TP08-300685C_BV2       ---------------CCTGGGAGGGTCTCCTGAATTGATTGACCACCCGC
DG75_MLV               --GTCTGCTGATCCTGGGAGGGTCTCCTCAGATTGATTGACCACCCAC
TP08-300685A_BV2       ---------------CCTGGGAGGGTCTCCTGAATTGATTGACCACCCGC
HB4120NOR_BV2          ---------------CCTGGGAGGGTCTCCTCAGATTGATTGACTACCCAC
GB606_BV2              ---------------CCTGGGAGGGTCTCCTCAGATTGATTGACTACCCAC
TP08-300288_BV2        ---------------CCTGGGAGGGTCTCCTCAGATTGATTGACTACCCAC
NAIDS                  AGCTCTCAAAGTTACAAGAAGTTCAGTTAAGATTAACAGTTACAAT
                                      *   *    *    *       *   *
```

```
GB339_BV1           TAGATCTGTATCTGGCCGGTTCCGCGGAAGAACTGACGAGTTCGTATTCCC
GB200_BV1           TAGATCTGTATCTGGCCGGTTCCGCGGAAGAACTGACGAGTTCGTATTCCC
TP08-S00512_BV1     TAGATCTGTATCTGGCCGGTTCCGCGGAAGAACTGACGAGTTCGTATTCCC
GB208_BV1           TAGATCTGTATCTGGAGGATCCGCGGAAGAACTGACGAGTTCGTATTCCC
TP08-S00234_BV1     TAGATCTGTATCTGGCCGGTTCCGCGGAAGAACTGACGAGTTCGTATTCCC
GB209_BV1           TAGATCTGTATCTGGCCGGTTCCGCGGAAGAACTGACGAGTTCGTATTCCC
GB620A_BV1          TAGATCTGTATCTGGCCGGTTCCGCGGAAGAACTGACGAGTTCGTATTCCC
TP08-S00509_BV1     TAGATCTGTATCTGGCCGGTCCCGCGGAAGAACTGACGAGTTCGTATTCCC
GB250_BV1           TAGATCTGTATCTGGCCGGTTCCACGGAAGAACTGACGAGTTCGTACTCCC
BFB-1_BV1           TAGATCTGTATCTGGCCGGTTCCGCGGAAGAACTGACGAGTTCGTATTCCC
KB106K_BV1          TAGATCTGTATCTGGCCGGTTCCGCGGAAGAACTGACGAGTTCGTATTCCC
RFMIY_17_BV1        TAGATCTGTATCTGGCCGGTTCCGCGGAAGAACTGACGAGTTCGTATTCCC
RFMIY_SF6_BV1       TAGATCTGTATCTGGCCGGTTCCGCGGAAGAACTGACGAGTTCGTATTCCC
GB338_BV1           TAGATCTGTATCTGGCCGGTTCCGCGGAAGAACTGACGAGTTCGTATTCCC
1390DGDX_BV1        TAGATCTGTATCTGGCCGGTCCCGCGGAAGAACTGACGAGTTCGTATTCCC
BB068A_BV1          TAGATCTGTATCTGGCCGGTTCCGCGGAAGAACTGACGAGTTCGTATTCCC
BB068C_BV1          TAGATCTGTATCTGGCCGGTACCGCGGAAGAACTGACGAGTTCGTATTCCC
mouse_polytropic_51 TAGATCTGTATCTGGCCGGTTCCGCGGAAGAACTGACGAGTTCGTATTCCC
GB529_BV1           TAGATCTGTATCTGGCCGGTCCCGCGGAAGAACTGACGAGTTCGTATTCCC
TP08-S00192_BV2     TAGATCTGTATCTGGCCGGTCCCGCGGAAGAACTGACGAGTTCGTATTCCC
GB534_BV1           TAGATCTGTATCTGGCCGGTTCCGCGGAAGAACTGACGAGTTCGTATTCCC
GB600C_BV1          TAGATCTGTATCTGGCCGGTCCCGCGGAAGAACTGACGAGTTCGTATTCCC
BB048B_BV1          TAGATCTGTATCTGGCCGGTTCCGCGGAAGAACTGACGAGTTCGTATTCCC
XMRV_VP62           TAGATCTGTATCTGGCCGGTTCCGCGGAAGAACTGACGAGTTCGTATTCCC
TP08-S0076A_BV2     TAGATCTGAATCTGGCCGGTCCGGTGGAAGAACTGACGAGTTCATATTCCC
TP08-S0076C_BV2     TAGATCTGAATCTGGCCGGTCCGGTGGAAGAACTGACGAGTTCATATTCCC
TP08-S0076B_BV2     TAGATCTGAATCTGGCCGGTCCGGTGGAAGAACTGACGAGTTCATATTCCC
TP08-S00651A_BV2    TAGATCTGAATCTGGCCGGTCCGGTGGAAGAACTGACGAGTTCATATTCCC
TP08-S00655C_BV2    TAGATCTGAATCTGGCCGGTCCGGTGGAAGAACTGACGAGTTCATATTCCC
DG75_MLV            TAGATCTGAATCTGGCCGGTCCGGTGGAAGAACTGACGAGTTCATATTCCC
TP08-S00655A_BV2    TAGATCTGAATCTGGCCGGTCCGGTGGAAGAACTGACGAGTTCATATTCCC
BB4122KNOR_BV2      TAGATCTGAATCTGGCCGGTCCGGTGGAAGAACTGACGAGTTCATATTCCC
GB606_BV2           TAGATCTGAATCTGGCCGGTCCGGTGGAAGAACTGACGAGTTCATATTCCC
TP08-S00288_BV2     TAGATCTGAATCTGGCCGGTCCGGTGGAAGAACTGACGAGTTCATATTCCC
MR183               TAACACTGACTCTGT-CTCGGTTCTGTAGCCGGTTTTTGTCCCC
                    **  ** *   *   *  **     **         ***
```

```
GB339_BV1           TTGTGGCCCATTCTGT-ATCAGTTAACCT----ACCCGAGTCGGACTTTTT
GB620D_BV1          TTGTGGCCCATTCTGT-ATCAGTTAACCT----ACCCGAGTCGGACTTTTT
TP08-S00512_BV1     TTGTGGCCCATTCTGT-ATCAGTTAACCT----ACCCGAGTCGGACTTTTT
GB620B_BV1          TTGTGGCCCATTCTGT-ATCAGTTAACCT----ACCCGAGTCGGACTTTTT
TP08-S00236_BV1     TTGTGGCCCATTCTGT-ATCAGTTAACCT----ACCCGAGTCGGACTTTTT
GB209_BV1           TTGTGGCCCATTCTGT-ATCAGTTAACCT----ACCCGAGTCGGACTTTTT
GB620A_BV1          TTGTGGCCCATTCTGT-ATCAGTTAACCT----ACCCGAGTCGGACTTTTT
TP08-S00506_BV1     TTGTGGCCCATTCTGT-ATCAGTTAACCT----ACCCGAGTCGGACTTTTT
GB250_BV1           TTGTGGCCCATTCTGT-ATCAGTTAACCT----ACCCGAGTCGGACTTTTT
BPH-1_BV1           TTGTGGCCCATTCTGT-ATCAGTTAACCT----ACCCGAGTCGGACTTTTT
RK106N_BV1          TTGTGGCCCATTCTGT-ATCAGTTAACCT----ACCCGAGTCGGACTTTTT
SFWYI_37_BV1        TTGTGGCCCATTCTGT-ATCAGTTAACCT----ACCCGAGTCGGACTTTTT
SFWYI_3P6_BV1       TTGTGGCCCATTCTGT-ATCAGTTAACCT----ACCCGAGTCGGACTTTTT
GB338_BV1           TTGTGGCCCATTCTGT-ATCAGTTAACCT----ACCCGAGTCGGACTTTTT
1390DONOR_BV1       TTGTGGCCCATTCTGT-ATCAGTTAACCT----ACCCGAGTCGGACTTTTT
BK068A_BV1          TTGTGGCCCATTCTGT-ATCAGTTAACCT----ACCCGAGTCGGACTTTTT
BK068C_BV1          TTGTGGCCCATTCTGT-ATCAGTTAACCT----ACCCGAGTCGGACTTTTT
mouse_polytropic_53 TTGTGGCCCATTCTGT-ATCAGTTAACCT----ACCCGAGTCGGACTTTTT
GB529_BV1           TTGTGGCCCATTCTGT-ATCAGTTAACCT----ACCCGAGTCGGACTTTTT
TP08-S00192_BV2     TTGTGGCCCATTCTGT-ATCAGTTAACCT----GCCCGAGTCGGATTTTTT
GB534_BV1           TTGTGGCCCATTCTGT-ATCAGTTAAACT----ACCCGAGTCGGACTTTTT
GB620C_BV1          TTGTGGCCCATTCTGT-ATCAGTTAACCT----ACCCGAGTCGGACTTTTT
BK068B_BV1          TTGTGGCCCATTCTGT-ATCAGTTAACCT----ACCCGAGTCGGACTTTTT
XMRV_VP62           TTGTGGCCCATTCTGT-ATCAGTTAACCT----ACCCGAGTCGGACTTTTT
TP08-S0076A_BV2     TTGTGGCCCAATCTGT-ATCTGAGAACCG----ACCCGTCTCGGACTCCTT
TP08-S0076C_BV2     TTGTGGCCCAATCTGT-ATCTGAGAACCG----ACCCGTCTCGGACTCCTT
TP08-S0076B_BV2     TTGTGGCCCAATCTGT-ATCTGAGAACCG----ACCCGTCTCGGACTCCTT
TP08-S00654B_BV2    TTGTGGCCCAATCTGT-ATCTGAGAACCG----ACCCGTCTCGGACTCCTT
TP08-S00655C_BV2    TTGTGGCCCAATCTGT-ATCTGAGAACCG----ACCCGTCTCGGACTCCTT
0675_MLV            TTGTGGCCCAATCTGT-ATCTGAGAACCG----ACCCGTCTCGGACTCCTT
TP08-S00655A_BV2    TTGTGGCCCAATCTGT-ATCTGAGAACCG----ACCCGTCTCGGACTCCTT
BB412DONOR_BV2      TTGTGGCCCAATCTGT-ATCTGAGAACCG----ACCCGTCTCGGACTCCTT
GB604_BV2           TTGTGGCCCAATCTGT-ATCTGAGAACCG----ACCCGTCTCGGACTCCTT
TP08-S00288_BV2     TTGTGGCCCAATCTGT-ATCTGAGAACCG----ACCCGTCTCGGACTCCTT
MAIDS               CTCCGACAGACTGAGTCGCCCGGGTACCCGTGTTCCCAATAAAGCCTCTT
                      *   *       *  **    *      *      **    *    **
```

FIG 2 (cont.)

```
GB339_BV1           -GGAGCTCCGCCACTGT----------ACGTGGCTTTGTTGGGGGACGAGA
GB620D_BV1          -GGAGCTCCGCCACTGT----------ACGTGGCTTTGTTGGGGGACGAGA
TP08-S00512_BV1     -GGAGCTCCGCCACTGT----------ACGTGGCTTTGTTGGGGGACGAGA
GB620B_BV1          -GGAGCTCCGCCACTGT----------ACGTGGCTTTGTTGGGGGACGAGA
TP08-S00236_BV1     -GGAGCTCCGCCACTGT----------ACGTGGCTTTGTTGGGGGACGAGA
GB209_BV1           -GGAGCTCCGCCACTGT----------ACGTGGCTTTGTTGGGGGACGAGA
GB620A_BV1          -GGAGCTCCGCCACTGT----------ACGTGGCTTTGTTGGGGGACGAGA
TP08-S00508_BV1     -GGAGCTCCGCCACTGT----------ACGTGGCTTTGTTGGGGGACGAGA
GB250_BV1           -GGAGCTCCGCCACTGT----------ACGTGGCTTTGTTGGGGGACGAGA
SPB-1_BV1           -GGAGCTCCGCCACTGT----------ACGTGGCTTTGTTGGGGGACGAGA
KB106R_BV1          -GGAGCTCCGCCACTGT----------ACGTGGCTTTGTTGGGGGACGAGA
WBMYV_77_BV1        -GGAGCTCCGCCACTGT----------ACGTGGCTTTGTTGGGGGACGAGA
WBMYV_SPG_BV1       -GGAGCTCCGCCACTGT----------ACGTGGCTTTGTTGGGGGACGAGA
GB238_BV1           -GGAGCTCCGCCACTGT----------ACGTGGCTTTGTTGGGGGACGAGA
I39O2ONOR_BV1       -GGAGCTCCGCCACTGT----------ACGTGGCTTTGTTGGGGGACGAGA
RB068A_BV1          -GGAGCTCCGCCACTGT----------ACGTGGCTTTGTTGGGGGACGAGA
RB068C_BV1          -GGAGCTCCGCCACTGT----------ACGTGGCTTTGTTGGGGGACGAGA
mouse_polytropic_51 -GGAGCTCCGCCACTGT----------ACGTGGCTTTGTTGGGGGACGAGA
GB529_BV1           -GGAGCTCCTCCACTGT----------ACGTGGCTTTGTCGGGGGACGAGA
TP08-S00192_BV2     TGGAGCTCCTCCACTGTCGAGGGTACGTGGCTTTGTCGGGGGACGAGA
GB534_BV1           -GGAGCTCCGCCACTGT----------ACGTGGCTTTGTTGGGGGACGAGA
GB620C_BV1          -GGAGCTCCGCCACTGT----------ACGTGGCTTTGTTGGGGGACGAGA
RB068B_BV1          -GGAGCTCCGCCACTGT----------ACGTGGCTTTGTTGGGGGACGAGA
XMRV_VP62           -GGAG-----------------------TGGTTTGTTGGGGGACGAGA
TP08-S007AA_BV2     -GGAGCCTCTCCTTTGACCGAGGGATACGTGTTCTGTTGGGCGGGGAGG
TP08-S007AC_BV2     -GGAGCCTCTCCTTTGACCGAGGGATACGTGTTCTGTTGGGCGGGGAGG
TP08-S00762_BV2     -GGAGCCTCTCCTTTGACCGAGGGATACGTGTTCTGTTGGGCGGGGAGG
TP08-S00655B_BV2    -GGAGCCTCTCCTTTGACCGAGGGATACGTGTTCTGTTGGGCGGGGAGG
TP08-S00655C_BV2    -GGAGCCTCTCCTTTGACCGAGGGATACGTGTTCTGTTGGGCGGGGAGG
DG75_SLV            -GGAGCCTCTCCTTTGACCGAGGGATACGTGTTCTGTTGGGCGGGGAGG
TP08-S00655A_BV2    -GGAGCCTCTCCTTTGACCGAGGGATACGTGTTCTGTTGGGCGGGGAGG
RB4120ONOR_BV2      -GGAGCCTCTCCTTTGACCGAGGGATACGTGTTCTGTTGGGCGGGGAGG
GB606_BV2           -GGAGCCTCTCCTTTGACCGAGGGATACGTGTTCTGTTGGGCGGGGAGG
TP08-S00288_BV2     -GGAGCCTCTCCTTTGACCGAGGGATACGTGTTCTGTTGGGCGGGGAGG
AIDS                GCTGATTACATCCGAAT----------CGTGGTCTGGCTGATCCTGGGA
                                                   ***    *  *      *  *
```

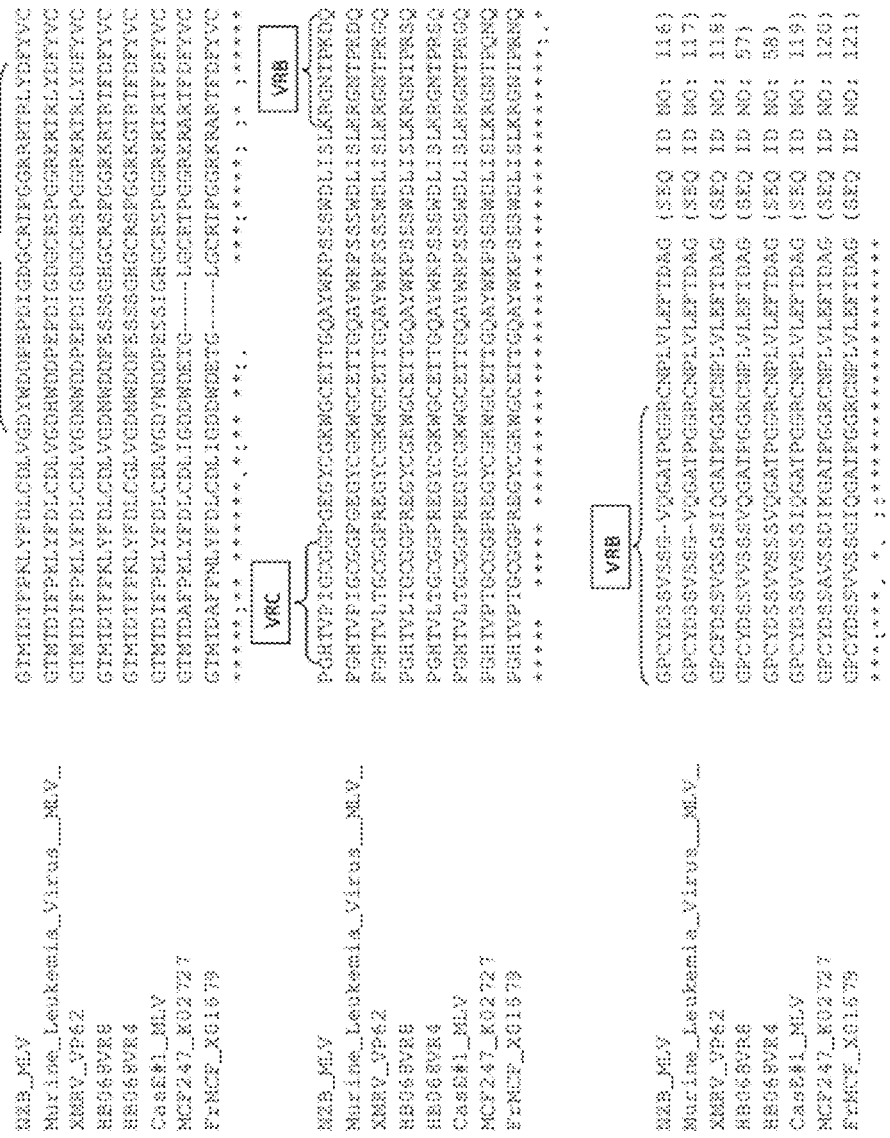

FIG 5

```
GB534a          AAGAACAGATGGCTCTC  (SEQ ID NO: 122)
GB534b          AAGAACAGATGGTACCC  (SEQ ID NO: 123)
GB529           AAGAACCGATGGTACCC  (SEQ ID NO: 124)
GB339           AAGAACAGATGGTCCCC  (SEQ ID NO: 125)
ARE consensus    AGAACAnnnTGTTCT   (SEQ ID NO: 126)
```

| | | |
|---|---|---|
| HB0688_BV1_sequence_ | CGAAGAACTGACGAGTTCGTATTCCGGCCGCCAACCCTGAGACGTCC | |
| GB606_BV2_sequence_ | CGAAGAACTGACGAGTTCATATTCCGGCCGCCAG--CCTGAGACGTCT | |
| XMRV | GGAAGAACTGACGAGTCGAGTTCGTATTCCCGGCCAG-CCCTGGAGACGTCC | |
| | ************************, *, ********, *, ** ***** | |
| | | |
| HB0688_BV1_sequence_ | CAGCGGCCTCGGGGGCCGTTTGTGGCCATTCTGTATCAGTTAACCT- | |
| GB606_BV2_sequence_ | CAGAGGCCATCGGGGGGCCCATCTTTGTGCCAATCTGTATCTGAGTTAACCG | |
| XMRV | CAGGGGCCTCGGGGCCCGGTTTGTGACCATTCTGTATCAGTTAACCT- | |
| | ***, ****, ****** ****, **** ********** ****** | |
| | | |
| HB0688_BV1_sequence_ | ACCCGAGTCGACTTTTGGAC TCCGCCACTG------ TACGTGGC | |
| GB606_BV2_sequence_ | ACCCGTCTCGGACTCTTTGGAGCCCTTCGTTTACGGAGGGATACGTGGT | |
| XMRV | ACCCGAGTCGGACTTTTG-----------------------CAGTGGC | |
| | ****** *, *****, **** | |
| | | |
| HB0688_BV1_sequence_ | TTTTGTGGGGGACGAGAGACAGAGACACTTC--CGGCCCCCGGTCTGAATT | |
| GB606_BV2_sequence_ | TCTGTTGGGGCCCCCCGAGCGGCCGAAACGGCCTCTCCCCCCCATCTGAATT | |
| XMRV | TTTGTTGGAGGACGAAGAGACAGAGACACTTC--CCGGCCCCGGTCTGAATT | |
| | * ****, **, *********, ***, *** *, *********** | |
| | | |
| HB0688_BV1_sequence_ | TTGCTTTCGGTTTATGCCGAACCGCGCCGCGGGTCTG------ (SEQ ID NO: 10) | |
| GB606_BV2_sequence_ | TTGCTTTCGGTTTCCGGTGAACCGGCGGCCGGGGGTCTG------ (SEQ ID NO: 17) | |
| XMRV | TTGCTTTCGGTTTACGCCGAAACCGCGCCGCGGGTCTGATTTGT (SEQ ID NO: 104) | |
| | ***********, *, ** *, *** *********** * | |

IDENTIFICATION OF A NOVEL RETROVIRUS IN PATIENTS WITH BENIGN PROSTATIC HYPERPLASIA

CROSS REFERENCE TO RELATED APPLICATION

This claims the benefit of U.S. Provisional Application No. 61/407,846, filed Oct. 28, 2010, which is incorporated herein in its entirety.

ACKNOWLEDGMENT OF GOVERNMENT SUPPORT

This invention was made with government support under grant number CA124892 awarded by the National Institutes of Health. The government has certain rights in the invention.

FIELD

This disclosure relates to retroviruses associated with benign prostatic hyperplasia, more specifically to methods for detecting presence of the virus in a sample and methods for eliciting an immune response to the virus in a subject.

BACKGROUND

The prevalence of benign prostatic hyperplasia (BPH) increases sharply with age after 40 years, and by age 75 approximately 75% of men will have evidence of this disease. Despite intensive investigation, little is known about the molecular events that lead to BPH. At the histological level, it is clear that BPH arises from the transitional zone of the prostate, including either formation of nodules containing mostly stromal elements reminiscent of embryonic mesenchyme, or a mix of both stromal and epithelial elements with increased proliferation in one or both cellular compartments. This increased cell number leads to compression of the urethra, which can lead to problems with voiding and, in the worst case scenarios, renal dysfunction caused by bladder outlet obstruction (BOO).

Androgen signaling does not appear to be involved in initiation of the disease, however it is necessary for continued proliferation of the cells, and thus, pharmacological interventions for BPH include 5-alpha-reductase inhibitors to prevent the conversion of testosterone to dihydrotestosterone, reducing the benign prostatic enlargement (BPE). Patients are also typically treated with alpha-adrenergic antagonists, which release tension on the bladder neck, prostate, and prostatic capsule and therefore relieve BOO. Alpha-adrenergic antagonists are more effective as a short term treatment for BPH/ lower urinary tract symptoms but over the long term, 5-alpha reductase inhibitors reduce the need for surgical intervention. Anti-androgens and gonadotropin-releasing hormone (GnRH) agonists may be more effective, but patients find the side-effects of androgen ablation unacceptable. In addition, treatment with alpha-1-adrenergic antagonists for BPH can be complicated by their hypotensive actions, in some cases leading to heart failure. Other side-effects of these treatments include asthenia (muscle weakness) and sudden falls in blood pressure resulting in dizziness. These side effects are bothersome enough to result in up to 10% of patients withdrawing from treatment. Reduction of the size of the prostate gland usually takes 6-12 months of treatment with 5-alpha-reductase inhibitors before symptoms are significantly improved.

SUMMARY

Accordingly, there is a need in the art for additional diagnostic methods to detect the presence of BPH or determine a risk for developing BPH. There is also a need for agents to inhibit (or even prevent) and/or treat BPH. Disclosed herein are novel retroviruses associated with BPH and viral nucleic acids and polypeptides encoded by such nucleic acids. Also disclosed are methods of detecting presence of BPH virus in a sample from a subject and agents that can produce an immune response to a BPH virus that can be used for treatment and/or protection from a BPH virus infection. The BPH viruses disclosed herein are related to previously identified gammaretroviruses such as murine leukemia virus and xenotropic murine leukemia virus-related virus (XMRV), but are distinct from these viruses based on nucleic acid and amino acid sequences. Therefore, the methods disclosed herein include methods of specifically detecting BPH virus (such as a BPH virus polynucleotide or polypeptide) in a sample from a subject, for example discriminating the presence of BPH virus in a sample as opposed to XMRV. In some examples, the disclosed methods include detecting the presence of a BPH virus and the absence of XMRV in a sample from a subject.

Methods for producing an immune response to a BPH virus are disclosed herein. Methods for treating a BPH virus infection, or inhibiting (or even preventing) a BPH virus infection in a subject, are also disclosed herein. The BPH virus infection can be latent or active.

In several embodiments, the methods include administering to the subject a therapeutically effective amount of a BPH virus polypeptide (or an immunogenic fragment thereof), or a polynucleotide encoding the polypeptide. In some examples, the polypeptide comprises an amino acid sequence at least 75% identical (such as at least 80%, 85%, 90%, 95%, or more identical) to at least one of the amino acid sequences set forth as SEQ ID NOs: 39-58 or an immunogenic fragment thereof. In additional embodiments, the methods include administering to the subject a therapeutically effective amount of a polypeptide comprising at least eight consecutive amino acids of at least one of the amino acid sequences set forth as SEQ ID NOs: 39-58. In some examples, the polypeptide includes a conservative variant of the polypeptide (for example, one or more conservative amino acid substitutions).

In other examples, the methods include administering to the subject a therapeutically effective amount of a polynucleotide comprising a nucleic acid sequence at least 75% (such as at least 80%, 85%, 90%, 95%, or more) identical to at least one of the nucleic acid sequences set forth as SEQ ID NOs: 1-38 or at least 24 consecutive nucleotides of SEQ ID NOs: 1-38. Also provided are methods of eliciting an immune response to a BPH virus in a subject by administering a virus-like particle (VLP) containing a BPH virus polypeptide disclosed herein. In several examples, the immune response is a protective immune response. In additional embodiments, methods are disclosed for inhibiting an infection with BPH virus, or treating an infection with BPH virus.

Methods for detecting presence of BPH virus in a sample are also disclosed herein. The methods include detecting the presence of a BPH virus polynucleotide in a sample from the subject. In some examples, the BPH virus polynucleotide includes a BPH virus gag nucleic acid, gag-related nucleic acid (such as a glyco-gag nucleic acid), env nucleic acid, pol nucleic acid, variable region nucleic acid, androgen response element (ARE) nucleic acid, or a combination of two or more thereof. In particular examples, the BPH polynucleotide includes a nucleic acid sequence at least 75% (such as at least 80%, 85%, 90%, 95%, or more) identical to at least one of the nucleic acid sequences set forth as SEQ ID NOs: 1-38 or a portion thereof (such as at least 10 or at least 24 consecutive nucleotides), wherein the nucleic acid sequence is not an XMRV nucleic acid sequence. In one example, a BPH virus polynucleotide is detected using real-time PCR.

In other examples the method includes detecting the presence of a BPH virus polypeptide (or a fragment thereof) in a sample from the subject. The BPH virus polypeptide includes a BPH virus gag polypeptide, gag-related polypeptide (such as a glyco-gag polypeptide), env polypeptide, pol polypeptide, or a combination of two or more thereof. In particular examples, the BPH polypeptide includes an amino acid sequence at least 75% identical (such as at least 80%, 85%, 90%, 95%, or more identical) to at least one of the amino acid sequences set forth as SEQ ID NOs: 39-58. In one example, a BPH virus polypeptide is detected using an immunoassay, such as ELISA. In other examples, the methods include detecting the presence of a BPH virus antibody that specifically binds to a BPH virus polypeptide. The BPH polypeptide includes an amino acid sequence at least 75% identical (such as at least 80%, 85%, 90%, 95%, or more identical) to at least one of the amino acid sequences set forth as SEQ ID NOs: 39-58. In some examples, detecting presence of BPH virus (such as a BPH virus polynucleotide, polypeptide, or antibody) in a sample from a subject diagnoses the subject as having BPH or being at risk for developing BPH.

The foregoing and other features of the disclosure will become more apparent from the following detailed description, which proceeds with reference to the accompanying figures.

BRIEF DESCRIPTION OF THE DRAWINGS

FIG. 2 is a multiple sequence alignment (CLUSTALW) of gag region nucleic acid sequences obtained from BPH patient samples, prostate tissue from organ donors, WPMY cell line, XMRV, and other murine retroviruses. An asterisk (*) indicates that the nucleotide is completely conserved.

FIG. 4A is an alignment of envelope variable region (VR) amino acid sequences from two BPH virus clones from a BPH patient (HB068VR8 and HB068VR4), and from closely related murine leukemia-related viruses, including a virus isolated from a wild mouse caught in Los Casitas, Calif., XMRV, Mink cell forming virus (MCF247), Friend Mink Cell forming virus (FrMCF), NZB-9-1, and murine leukemia virus.

FIG. 5 is an alignment of androgen response element (ARE) sequences from three BPH samples compared to an ARE consensus sequence.

FIG. 6 is an alignment of gag region nucleic acid sequences from a sample with BV1 virus (HB068B), a sample with BV2 virus (GB606), and XMRV_VP62. The bold sequence indicates the BV1 real-time PCR probe and the italicized sequence indicates the BV2 real-time PCR probe.

SEQUENCE LISTING

Figure 1:
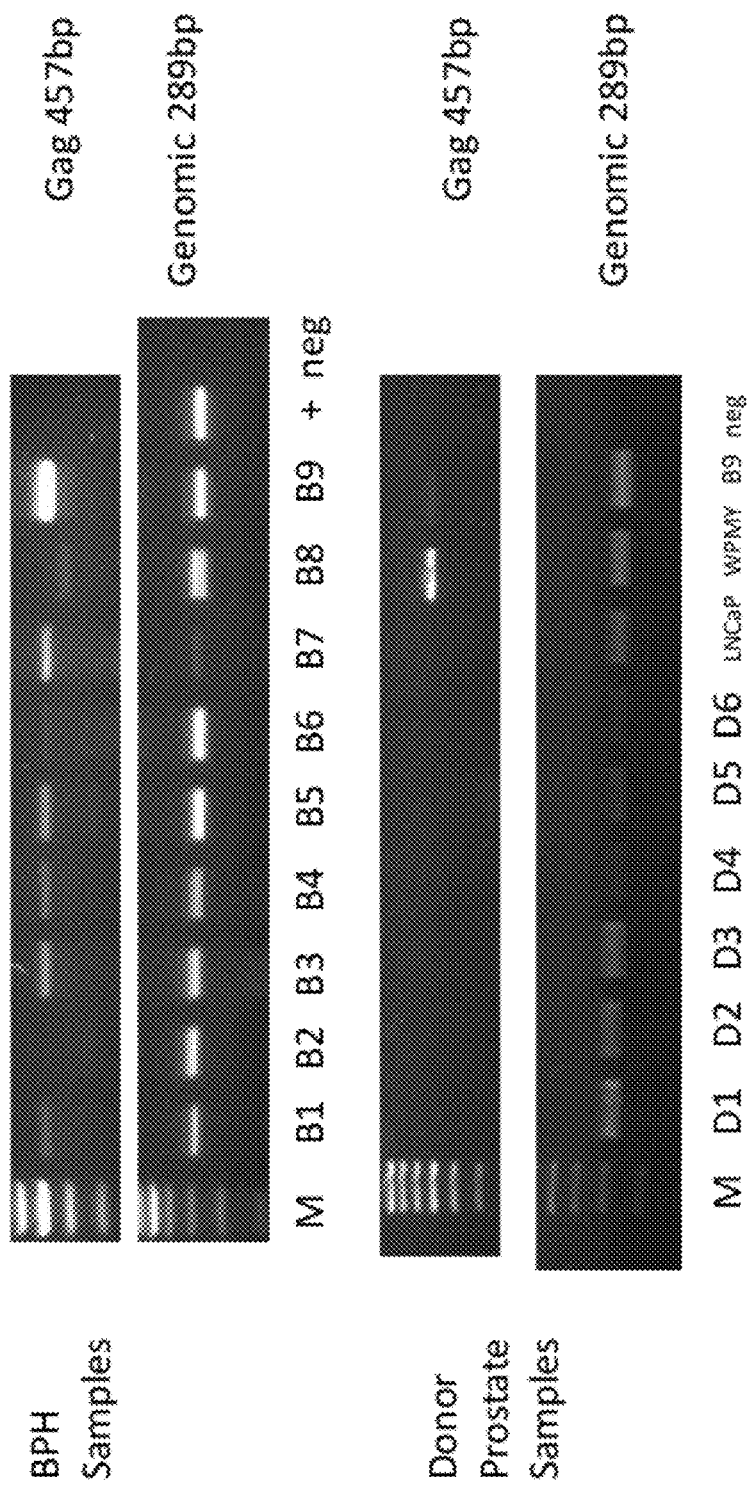
FIG. 1 is a series of digital images showing amplification of a gag region from a novel retrovirus in BPH samples, donor samples, and prostate cell lines. Genomic PCR was performed on all samples to confirm the integrity of the DNA utilizing a sequence-tagged site (STR D7S820). +, positive control (LNCaP cell line); neg, negative control (water only); LNCaP, prostate cancer cell line; WPMY, non-cancer prostate stromal cell line.

The nucleic acid and amino acid sequences listed herein are shown using standard letter abbreviations for nucleotide bases, and one letter code for amino acids. Only one strand of each nucleic acid sequence is shown, but the complementary strand is understood as included by any reference to the displayed strand.

The Sequence Listing is submitted as an ASCII text file in the form of the file named Sequence_Listing.txt, which was created on Oct. 27, 2011, and is 97,000 bytes, which is incorporated by reference herein.

In the accompanying sequence listing:

SEQ ID NOs: 1-27 are the nucleic acid sequences of BPH virus gag or gag-related polynucleotides.

SEQ ID NOs: 28-29 are nucleic acid sequences of BPH virus envelope region polynucleotides.

SEQ ID NOs: 30-33 are nucleic acid sequences of BPH virus variable region polynucleotides.

SEQ ID NOs: 34-38 are nucleic acid sequences of BPH virus androgen response element polynucleotides.

SEQ ID NOs: 39-54 are amino acid sequences of glyco-gag polypeptides.

SEQ ID NOs: 55-56 are amino acid sequences of partial envelope proteins.

SEQ ID NOs: 57-58 are amino acid sequences of envelope variable region polypeptides.

SEQ ID NOs: 59-68 are nucleic acid sequences of primers used to amplify BPH virus nucleotides.

SEQ ID NOs: 69 and 70 are nucleic acid sequences of genomic control primers.

SEQ ID NOs: 71 and 72 are nucleic acid sequence of BPH virus forward and reverse PCR primers, respectively.

SEQ ID NO: 73 is a nucleic acid sequence of an exemplary BPH virus 1 (BV1) probe.

SEQ ID NO: 74 is a nucleic acid sequence of an exemplary BPH virus 2 (BV2) probe.

SEQ ID NOs: 75-77 are nucleic acid sequences of exemplary RNase P primers and probe.

SEQ ID NOs: 78 and 79 are nucleic acid sequences of forward and reverse LTR methylation-specific primers, respectively.

SEQ ID NO: 80 is the nucleic acid sequence of XMRV VP62 isolate.

SEQ ID NOs: 81-115 are gag region nucleic acid sequences from BPH virus and other murine retroviruses.

SEQ ID NOs: 116-121 are envelope variable region amino acid sequences from murine leukemia virus and related viruses.

SEQ ID NOs: 122-126 are androgen response element nucleic acid sequences.

DETAILED DESCRIPTION

I. Abbreviations

ARE androgen response element
BOO bladder outlet obstruction
BPE benign prostatic enlargement
BPH benign prostatic hyperplasia
BV1 BPH virus 1
BV2 BPH virus 2
LTR long terminal repeat
ORF open reading frame
RNase P ribonuclease P
TURP transurethral resection of prostate VLP virus-like particle
VR: variable region
XMRV xenotropic murine leukemia virus-related virus

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Adjuvant: A vehicle used to enhance antigenicity. Adjuvants include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants (for example see U.S. Pat. No. 6,194,388; U.S. Pat. No. 6,207,646; U.S. Pat. No. 6,214,806; U.S. Pat. No. 6,218,371; U.S. Pat. No. 6,239,116; U.S. Pat. No. 6,339,068; U.S. Pat. No. 6,406,705; and U.S. Pat. No. 6,429,199). Adjuvants include biological molecules (a "biological adjuvant"), such as costimulatory molecules. Exemplary biological adjuvants include IL-2, RANTES, GM-CSF, TNF-α, IFN-γ, G-CSF, LFA-3, CD72, B7-1, B7-2, OX-40L and 4-1 BBL.

Androgen response element (ARE): A nucleic acid sequence that is recognized by the androgen receptor typically following androgen binding to the receptor. Androgen receptor binding to an ARE results in modulation of transcription (such as increase or decrease in transcription) of a downstream gene. AREs are generally a 15 base pair palindromic nucleic acid sequence. In one example, a consensus ARE includes AGAACANNNTGTTCT (SEQ ID NO: 126; wherein N is any nucleotide). In some examples, an ARE is an ARE from a BPH virus, such as ARE sequences disclosed herein.

Benign Prostatic Hyperplasia (BPH): A non-cancerous condition resulting from enlargement of the prostate gland. BPH is characterized by hyperplasia of prostate stromal and/or epithelial cells, which can result in formation of nodules in the periurethral region of the prostate. The nodules or expanded tissue eventually reaches a size that compresses the urethral canal, causing at least partial obstruction of the urethra. This leads to problems with voiding the bladder and can lead to renal dysfunction caused by bladder outlet obstruction (BOO).

BPH is typically diagnosed based on symptoms and clinical examination. Symptoms include weak urinary stream, prolonged emptying of bladder, hesitancy, incomplete bladder emptying, frequent urination, and urgency. Enlargement of the prostate can by detected by rectal examination and/or ultrasound examination. Prostate specific antigen testing and digital rectal examination can be used to help rule out prostatic malignancy.

Current treatments for BPH include α1-adrenergic receptor antagonists and/or 5α reductase inhibitors. If drug therapy is not effective, transurethral microwave therapy or transurethral needle ablation, which specifically deliver energy to create sufficient heat to cause cell death in the prostate. Surgical intervention includes transurethral resection of prostate (TURP) to remove enlarged prostate tissue.

Bisulfite treatment: The treatment of DNA with bisulfite or a salt thereof, such as sodium bisulfite ($NaHSO_3$). Bisulfite reacts readily with the 5,6-double bond of cytosine, but poorly with methylated cytosine. Cytosine reacts with the bisulfite ion to form a sulfonated cytosine reaction intermediate which is susceptible to deamination, giving rise to a sulfonated uracil. The sulfonate group can be removed under alkaline conditions, resulting in the formation of uracil. Uracil is recognized as a thymine by polymerases and amplification will result in an adenine-thymine base pair instead of a cytosine-guanine base pair.

BPH virus: A retrovirus identified in prostate samples from subjects with BPH. The BPH virus is distinct (for example at the nucleic acid or amino acid level) from XMRV. In particular examples, a BPH virus includes one or more nucleic acids having at least 75% identity (such as at least 80%, 85%, 90%, 95%, or more identity) with a nucleic acid sequence set forth as any one of SEQ ID NOS: 1-38, or the reverse complement thereof, wherein the nucleic acid sequence is not an XMRV nucleic acid sequence. In other examples, a BPH virus includes one or more polypeptides having at least 75% identity (such as at least 80%, 85%, 90%, 95%, or more identity) with an amino acid sequence set forth as any one of SEQ ID NOS: 39-58.

Conservative variants: A substitution of an amino acid residue for another amino acid residue having similar biochemical properties. "Conservative" amino acid substitutions include those substitutions that do not substantially affect or decrease an activity or antigenicity of a BPH virus polypeptide. A peptide can include one or more amino acid substitutions, for example 1-10 conservative substitutions, 2-5 conservative substitutions, 4-9 conservative substitutions, such as 1, 2, 3, 4, 5, 6, 7, 8, 9, or 10 conservative substitutions. Specific, non-limiting examples of a conservative substitution include the following examples:

| Original Amino Acid | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide, or that an immune response can be generated against the substituted polypeptide that is similar to the immune response against the unsubstituted polypeptide, such as a BPH virus polypeptide. Thus, in one embodiment, non-conservative substitutions are those that reduce an activity or antigenicity.

Consists Essentially Of/Consists Of: With regard to a polypeptide, a polypeptide consists essentially of a specified amino acid sequence if it does not include any additional amino acid residues. However, the polypeptide can include additional non-peptide components, such as labels (for example, fluorescent, radioactive, or solid particle labels), sugars or lipids. A polypeptide that consists of a specified amino acid sequence does not include any additional amino acid residues, nor does it include additional non-peptide components, such as lipids, sugars or labels.

With regard to a polynucleotide, a polynucleotide consists essentially of a specified nucleic acid sequence if it does not include any additional nucleotides. However, the polynucleotide can include additional non-nucleotide components, such as labels (for example, fluorescent, radioactive, or solid particle labels), sugars or lipids. A polynucleotide that consists of a specified nucleic acid sequence does not include any additional nucleotides, nor does it include additional non-nucleotide components, such as lipids, sugars or labels.

Diagnostic: Identifying the presence or nature of a pathologic condition, such as, but not limited to, BPH. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" means predicting the probability of development (for example, severity) of a pathologic condition, such as BPH.

DNA methylation: The covalent addition of a methyl group (—CH$_3$) to the 5'-carbon of cytosine, usually in a CpG dinucleotide, or sometimes adenine (particularly in bacteria). CpG sites are located throughout the genome. In eukaryotic cells, methylation is a means of inhibiting gene expression.

Hybridization: The ability of complementary single-stranded DNA or RNA to form a duplex molecule (also referred to as a hybridization complex). Nucleic acid hybridization techniques can be used to form hybridization complexes between a probe or primer and a nucleic acid, such as a BPH virus nucleic acid molecule (such as a BPH virus gag, gag-related, env, pol, variable region, or ARE nucleic acid). For example, a probe or primer (such as any of SEQ ID NOs: 59-68 or 71-74) having some homology to a disclosed BPH virus or human nucleic acid molecule can form a hybridization complex with a complementary nucleic acid molecule (such as any of SEQ ID NOs: 1-38).

Specifically hybridizable" and "specifically hybridizes" are terms which indicate a sufficient degree of complementarity such that stable and specific binding occurs between an oligonucleotide and its DNA or RNA target. An oligonucleotide need not be 100% complementary to its target DNA or RNA sequence to be specifically hybridizable. An oligonucleotide is specifically hybridizable when there is a sufficient degree of complementarity to avoid non-specific binding of the oligonucleotide to non-target sequences (such as XMRV sequences) under conditions in which specific binding is desired, or under conditions in which an assay is performed.

Hybridization conditions resulting in particular degrees of stringency will vary depending upon the nature of the hybridization method and the composition and length of the hybridizing nucleic acid sequences. Generally, the temperature of hybridization and the ionic strength (such as the Na$^+$ concentration) of the hybridization buffer will determine the stringency of hybridization. Calculations regarding hybridization conditions for attaining particular degrees of stringency are discussed in Sambrook et al., (1989) *Molecular Cloning*, second edition, Cold Spring Harbor Laboratory, Plainview, N.Y. (chapters 9 and 11). The following is an exemplary set of hybridization conditions and is not limiting:

Very High Stringency (detects sequences that share at least 90% identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (detects sequences that share at least 80% identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (detects sequences that share at least 50% identity)
Hybridization: 6×SSC at RT to 55° C. for 16-20 hours
Wash at least twice: 2×-3×SSC at RT to 55° C. for 20-30 minutes each.

The probes and primers disclosed herein can hybridize to nucleic acid molecules under low stringency, high stringency, and very high stringency conditions. In particular examples, the probes and primers disclosed herein hybridize to a BPH virus nucleic acid molecule and do not hybridize to an XMRV nucleic acid molecule.

Immune response: A response of a cell of the immune system, such as a B cell, natural killer cell, or a T cell, to a stimulus. In one embodiment, the response is specific for a particular antigen (an "antigen-specific response"), such as a BPH virus polypeptide or immunogenic fragment thereof. In one embodiment, an immune response is a T cell response, such as a Th1, Th2, or Th3 response. In another embodiment, an immune response is a response of a suppressor T cell.

Immunogenic composition: A composition comprising an effective amount of an immunogenic BPH virus polypeptide or a nucleic acid encoding the immunogenic BPH virus polypeptide that induces a measurable T response against the BPH virus, such as a CD8$^+$ T cell response, or induces a measurable B cell response (such as production of antibodies that specifically bind a BPH virus polypeptide). For in vitro use, the immunogenic composition can consist of the isolated nucleic acid, vector including the nucleic acid/or immunogenic peptide. For in vivo use, the immunogenic composition will typically comprise the nucleic acid, vector including the nucleic acid, and/or immunogenic polypeptide in pharmaceutically acceptable carriers and/or other agents. An immunogenic composition can optionally include an adjuvant, a costimulatory molecule, or a nucleic acid encoding a costimulatory molecule.

Immunogenic peptide: A peptide which comprises an allele-specific motif or other sequence such that the peptide will bind an MHC molecule and induce a T cell response, such as a CD8$^+$ or CD4$^+$ T cell response, or a B cell response (such as antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunogenic peptides can also be identified by measuring their binding to a specific MHC protein and by their ability to stimulate CD4 and/or CD8 when presented in the context of the MHC protein. In one example, an immunogenic "BPH virus peptide" is a series of contiguous amino acid residues from the BPH virus protein generally between 8 and 20 amino acids in length, such as about 8 to 12 or 9 to 10 residues in length. In some examples, an immunogenic peptide includes the disclosed BPH virus polypeptides (such as SEQ ID NOs: 39-58) or immunogenic fragments thereof.

Inhibiting or treating a disease: "Inhibiting" a disease or disorder refers to inhibiting the full development of a disease, for example in a person who is known to have a disease or be at risk for developing a disease, such as BPH. Inhibition of a disease can span the spectrum from partial inhibition to substantially complete inhibition (prevention) of the disease. In some examples, the term "inhibiting" refers to reducing or delaying the onset or progression of a disease or disorder. In other examples, inhibiting a disease refers to lessening symptoms of the disease or disorder. A subject to be administered with a therapeutically effective amount of the pharmaceutical compound to inhibit or treat the disease or disorder can be identified by standard diagnosing techniques for such a disorder, for example, basis of family history, or risk factors to develop the disease or disorder. In contrast, "treatment" refers to a therapeutic intervention that ameliorates a sign or symptom of a disease or pathological condition after it has begun to develop.

Isolated: An "isolated" biological component (such as a nucleic acid molecule, protein, or organelle) has been substantially separated or purified away from other biological components in the cell of the organism in which the component naturally occurs, such as other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids or proteins, or fragments thereof.

Label: A detectable compound or composition that is conjugated directly or indirectly to another molecule to facilitate detection of that molecule. Specific, non-limiting examples of labels include fluorescent tags, enzymatic linkages, and radioactive isotopes.

Long Terminal Repeat (LTR): An "LTR" is a "long terminal repeat" that is generated as a DNA duplex at both ends of the retrovirus when a retrovirus integrates into a host genome. The 5' LTR includes a U3, R, and U5 nucleic acid element. The 3' LTR also includes U3, R, and U5 nucleic acid element. In a replication competent retrovirus, LTRs also contain an active RNA polymerase II promoter which allows transcription of the integrated provirus by host cell RNA polymerase II to generate new copies of the retroviral RNA genome.

Methylation: A chemical or biochemical process of introducing a methyl group into an organic molecule. DNA methylation, the addition of a methyl group onto a nucleotide, is a post-replicative covalent modification of DNA that is catalyzed by a DNA methyltransferase enzyme (Koomar et al., *Nucl. Acids Res.* 22:1-10, 1994; and Bestor et al., *J. Mol. Biol.* 203:971-983, 1988).

In biological systems, DNA methylation can serve as a mechanism for changing the structure of DNA without altering its coding function or its sequence. DNA methylation is a heritable, reversible and epigenetic change. In some embodiments, it can alter gene expression, particularly by inactivating genes, which has profound developmental and disease consequences. For example, methylation of CpG islands that are associated with tumor suppressor genes can cause decreased gene expression. Increased methylation of such regions can lead to a reduction of normal gene expression, which may cause the selection of a population of cells having a selective growth advantage and thus may become malignant.

Open reading frame (ORF): A series of nucleotide triplets (codons) coding for amino acids without any termination codons. These sequences are usually translatable into a polypeptide.

Pharmaceutical agent or drug: A chemical compound or composition capable of inducing a desired therapeutic or prophylactic effect when properly administered to a subject.

Pharmaceutically acceptable carriers: The pharmaceutically acceptable carriers useful with the polypeptides and nucleic acids described herein are conventional. *Remington: The Science and Practice of Pharmacy*, The University of the Sciences in Philadelphia, Editor, Lippincott, Williams, & Wilkins, Philadelphia, Pa., $21^{st}$ Edition (2005) describes compositions and formulations suitable for pharmaceutical delivery of the polypeptides or polynucleotides herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. In some examples, an oligonucleotide is a polynucleotide of between 6 and 100 nucleotides in length. In some examples, polynucleotides or oligonucleotides include one or more phosphorothioate bonds and/or modified nucleotides (such as one or more peptide nucleic acids or locked nucleic acids).

Polypeptide: A polymer in which the monomers are amino acid residues which are joined together through amide bonds. When the amino acids are alpha-amino acids, either the L-optical isomer or the D-optical isomer can be used. The terms "polypeptide," "peptide," or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

Probes and primers: Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989, and *Current Protocols in Molecular Biology*, ed. Ausubel et al., Greene Publishing and Wiley-Interscience, New York, 1987 (with periodic updates). PCR primer pairs can be derived from a known sequence, for example, by using computer programs intended for that purpose such as Primer3 (Version 0.4.0, Whitehead Institute for Biomedical Research, Cambridge, Mass.).

Purified: The term purified does not require absolute purity; rather, it is intended as a relative term. Thus, for example, a purified antigen preparation is one in which the antigen is more pure than the protein in its originating environment within a cell or sample. A preparation of an antigen is typically purified such that the antigen represents at least 50% of the total protein content of the preparation. However, more highly purified preparations may be required for certain applications. For example, for such applications, preparations in which the antigen comprises at least 75% (such as at least 80%, 85%, 90%, or more) of the total protein content may be employed.

Retrovirus: Any virus in the family Retroviridae. These viruses have similar characteristics; specifically they share a replicative strategy. This strategy includes as essential steps reverse transcription of the virion RNA into linear double-stranded DNA, and the subsequent integration of this DNA into the genome of the cell. A retrovirus generally contains three genes known as "gag," "pol," and "env" that code for virion proteins.

A "pol" protein is a retroviral reverse transcriptase, which contains both DNA polymerase and associated RNAse H activities, and Integrase (IN). Pol mediates replication of the viral genome in vivo. A "gag" protein is a retroviral "group specific antigen" polypeptide which is proteolytically processed into the mature proteins MA (matrix), CA (capsid), and NC (nucleocapsid), and other proteins that are numerically designated. A "glyco-gag" protein is a gag-related protein that includes a glycosylated gag polypeptide that is non structural but is found in some infectious murine leukemia viruses, such as AKV and DG75. The glyco-gag protein of MLVs plays a role in viral pathogenesis and in vivo infectivity. It utilizes an alternative start codon (CUG) from the gag protein. An "env" polypeptide is a retroviral "envelope" protein which encodes the surface (SU) glycoprotein and the transmembrane (TM) protein of the virion. The SU glycoprotein and the TM protein form a complex that interacts specifically with cellular receptors.

In one embodiment, a retrovirus is a novel retrovirus (such as a retrovirus distinct from XMRV) associated with BPH virus, for example, BPH virus 1 and BPH virus 2, disclosed herein.

Sample: A sample, such as a biological sample, is a sample obtained from a plant or animal subject. As used herein, biological samples include cells, tissues, and bodily fluids, such as: blood; derivatives and fractions of blood, such as plasma or serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; or bone marrow aspirates. In a particular example, a sample includes a prostate tissue biopsy obtained from a human subject.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Variants of antigen polypeptides will possess a relatively high degree of sequence identity when aligned using standard methods.

Methods of alignment of sequences for comparison are well known in the art. Altschul et al. (1994) presents a detailed consideration of sequence alignment methods and homology calculations. The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website. A description of how to determine sequence identity using this program is available at the NCBI website, as are the default parameters.

Variants of antigenic polypeptides, such as a BPH virus polypeptide, are typically characterized by possession of at least 50% sequence identity counted over the full length alignment with the amino acid sequence of a native antigen sequence using the NCBI Blast 2.0, gapped blastp set to default parameters. Proteins with even greater similarity to the reference sequences will show increasing percentage identities when assessed by this method, such as at least 60%, at least 65%, at least 70%, at least 75%, at least 80%, at least 90%, at least 95%, or more sequence identity. When less than the entire sequence is being compared for sequence identity, variants will typically possess at least 75% sequence identity over short windows of 10-20 amino acids, and may possess sequence identities of at least 85% or at least 90%, 95%, or more, depending on their similarity to the reference sequence. Methods for determining sequence identity over such short windows are described at the NCBI website.

Subject: Living multi-cellular vertebrate organisms, a category that includes both human and non-human mammals.

Therapeutically effective amount: A dose sufficient to inhibit or prevent advancement, or to cause regression of a disease, or which is capable of relieving symptoms caused by a disease. In one embodiment, a therapeutically effective dose is a dose sufficient to inhibit advancement or relieve symptoms of BPH.

Variable region (VR): A portion of a retrovirus nucleic acid that is variable in sequence (for example in the envelope region). There are three "variable" regions in the envelope, called VRA, VRB and VRC. In some examples, variable region sequences can be used to differentiate between viruses. In a particular example, VR nucleic acid sequences differ between BPH virus and XMRV and can be utilized to differentiate these viruses.

Virus-like particle (VLP): Virus particles made up of one of more viral structural proteins, but lacking the viral genome. Because VLPs lack a viral genome, they are non-infectious. In addition, VLPs can often be produced by heterologous expression and can be easily purified. Most VLPs comprise at least a viral core protein that drives budding and release of particles from a host cell. One example of such a core protein is BPH virus gag or gag-related protein. As described herein, BPH virus VLPs can be produced by transfection of host cells with plasmids encoding at least a BPH virus gag or gag-related protein, such as those disclosed herein. After incubation of the transfected cells for an appropriate time to allow for protein expression (such as for approximately 72 hours), VLPs can be isolated from cell culture supernatants. In some examples, VLPs are isolated by low speed centrifugation (to remove cell debris), vacuum filtration and ultracentrifugation through 20% glycerol.

Xenotropic murine leukemia virus-related virus (XMRV): A gammaretrovirus (a genus that includes murine leukemia virus, feline leukemia virus, and gibbon ape leukemia virus) identified in prostate cancer samples. See e.g., International Pat. Publication No. WO 06/110589; Urisman et al., *PLoS Pathogens* 2:e25, 2006; each incorporated herein by reference. XMRV has not been identified in samples from subjects with BPH, and is distinct from the BPH viruses disclosed herein. In some examples, XMRV is disclosed in PCT Publication No. WO 06/110589. In another, non-limiting example, an exemplary XMRV sequence is disclosed herein as SEQ ID NO: 80.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. BPH Virus Polynucleotides and Polypeptides

It is disclosed herein that several viral polynucleotides or polypeptides encoded by such polynucleotides can be used to diagnose an individual with BPH or at risk for developing BPH. Such polynucleotides or polypeptides encoded by such polynucleotides (or immunogenic fragments thereof) can also be used to induce an immune response to BPH virus to inhibit or treat BPH. The BPH virus polynucleotides and polypeptides disclosed herein are distinct from previously identified XMRV both at the molecular level and clinically (for example XMRV has been identified in prostate cancer samples, but has not been identified in BPH samples). In some examples, a BPH virus polynucleotide or polypeptide is not an XMRV polynucleotide or polypeptide if the nucleic acid or amino acid sequence is not identical to an XMRV nucleic acid or amino acid sequence (such as the XMRV sequences disclosed in PCT Publication No. WO 06/110589).

A. BPH Virus Polynucleotides

BPH virus polynucleotides are disclosed herein. In several embodiments, the polynucleotide is a gag or gag-related (such as glyco-gag) nucleic acid that comprises or consists of the nucleic acid sequence set forth as:

```
                                                                    (SEQ ID NO: 1)
CCTTGGGAGGGTCTCCTCAGATTGATTGACTACCCACGTCGGGGTCTTTCATTTGGAGGTTCCACCGAGATTTGGAG

ACCCCTGCCCAGGGACCACCGACCCCCGCCGGGAGGTAAGCTGGCCAGCGGTCGTTTCGTGTCTGTCTCTGTCTTCG

TGCGTGTTTGTGCCGGCATCCAATGTTTGCGCCTGCGTCTGTACTAGTTAGCTAACTAGATCTGTATCTGGCGGTTCC

GCGGAAGAACTGACGAGTTCGTATTCCCGGCCGCAGCCCCTGGGAGACGTCCCAGCGGCCTCGGGGGCCCGTTTTGTG

GCCCATTCTGTATCAGTTAACCTACCCGAGTCGGACTTTTTGGAGCTCCGCCACTGTACGTGGCTTTGTTGGGGACG

AGAGACAGAGACACTTCCCGCCCCCGTCTGGATTTTTGCTTTCGGTTTTACGCCGAAACCGCGCCGCGCGTCTG (SEQ ID NO: 2)
CCTTGGGAGGGTCTCCTCAGATTGATTGACTACCCACGTCGGGGTCTTTCATTTGGAGGTTCCACCGAGATTTGGAG

ACCCCTGCCCAGGGACCACCGACCCCCGCCGGGAGGTAAGCTGGCCAGCGGTCGTTTCGTGTCTGTCTCTGTCTTCG

TGCGTGTTTGTGCCGGCATCCAATGTTTGCGCCTGCGTCTGTACTAGTTAGCTAACTAGATCTGTATCTGGCGGTTCC

ACGGAAGAACTGACGAGTTCGTACTCCCGGCCGCAGCCCCTGGGAGACGTCCCAGCGGCCTCGGGGGCCCGTTTTGTG

GCCCATTCTGTAGCAGTTAACCTACCCGAGTCGGACTTTTTGGAGCTCCGCCACTGTACGTGGCTTTGTTGGGGACG

AGAGACAGAGACACTTCCCGCCCCCGTCTGAATTTTGCTTTCGGTTTTACGCCGAAACCGCGCCGCGCGTCTG
```

-continued (SEQ ID NO: 3)
CCTTGGGAGGGTCTCCTCAGATTGATTGACTACCCACGTCGGGGTCTTTCATTTGGAGGTTCCACTGAGATTTGGAG

ACCCCTGCCCAGGGACCACCGACCCCCGCCGGGAGGTAAGCTGGCCAGCGGTCGTTTCGTGTCTGTCTCTGTCTTCG

TGCGTGTTTGTGCCGGCATCCAATGTTTGCGCCTGCGTCTGTACTAGTTAGCTAACTAGATCTGTATCTGGCGGTTCC

GCGGAAGAACTGACGAGTTCGTATTCCCGGCCGCAGCCCTGGGAGACGTCCCAGCGGCCTCGGGGGCCCGTTTTGTG

GCCCATTCTGTATCAGTTAACCTACCCGAGTCGGACTTTTTGGAGCTCCGCCACTGTACGTGGCTTTGTTGGGGACG

AGAGACAGAGACACTTCCCGCCCCCGTCTGAATTTTTGCTTTCGGTTTTATGCCGAAACCGCGCCGCGCGTCTG (SEQ ID NO: 4)
CCTTGGGAGGGTCTCCTCAGATTGATTGACTGCCCACCTGGGGGTCTTTCATTTGGAGGTCCCACCGAGATCAGGAG

ACCCCTGCCCAGGGACCACCGACCCCCGCCGGGAGGTAAGCTGGCCAGCGGTCGTTTCGTGTCTGTCTCTGTCTCCGT

GCGTGTTTGTGCCGGCATCTAATGTTTGCGCCTGCGTCTGTACTGGTTGGCTAACTAGATCTGTATCTGGCGGTTCCG

TGGAAGAACTGACGAGTTCGTATTCCCGGCCGCAGCCCTGGGAGACGTCCCAGCGGCCTCGGGGGCCCGTTTTGTGGC

CCATTCTGTATCAGTTAACCTACCCGAGTCGGACTTTTTGGAGCTCCTCCACTGTACGTGGCTTTGTCGGGGACGAG

AGGCAGAGACACTTCCCTCCCCCGTCTGAATTTTTGCTTTCGGTTTTACGCCGAAACCGCGCCGCGCGTCTG (SEQ ID NO: 5)
CCTTGGGAGGGTCTCCTCAGATTGATTGACTGCCCACCTGGGGGTCTTTCATTTGGAGGTTCCACCGAGATCAGGAG

ACCCCTGCCCAGGGACCACCGACCCCCGCCGGGAGGTAAGCTGGCCAGCGGTCGTTTTGTGTCTGTCTCTGTCTCCGT

GCGTGTTTGTGCCGGCATCTAATGTTTGCGCCTGCGTCTGTACTAGTTGGCTAACTAGATCTGTATCTGGCGGTTTCG

CGGAAGAACTGACGAGTTCGTATTCCCGGCCGCAGCCCTGGGAGACGTCCCAGCGGCCTCGGGGCCCGTTTTGTGG

CCCATTCTGTATCAGTTAAACTACCCGAGTCGGACTTTTTGGAGCTCCGCCACTGTACGTGGCTTTGTTGGGGACGA

GAGACAGAGACACTTCCCGCCCCCGTCTGGATTTTTGCTTTCGGTTTTACGCCGAAACCGCGCCGCGCGTCTG (SEQ ID NO: 6)
CCTTGGGAGGGTCTCCTCAGATTGATTGACTACCCACGTCGGGGTATTTCATTTGGAGGTTCCACCGAGATTTGGAG

ACCCCTGCCCAGGGACCACCGACCCCCGTCGGGAGGTAAGCTGGCCAGCGGTCGTTTCGTGTCTGTCTCTGTCTTCG

TGCGTGTTTGTGCCGGCATCCAATGTTTGCGCCTGCGTCTGTACTAGTTACGCTAACTAGATCTGTATCTGGAGGATC

CGCGGAAGAACTGAGGAGTTCGTATTCCCGGCCGCAGCCCTGGGAGACGTCCCAGTGGCCTCGGGGGCCCGGTTTGT

GGTCCATTCTGTATCACTGAACCTACCCGAGTCTGACTTTTTGGAGCTCCGCCACTGTACGTGGGTTTGGTGGGGGAC

GAGAGACAGAGACACTTCCCGCCCCCGTCTGGATTTTTGCTTTCGGCTTTACGCCGAAACCGCGCCGCGCGTCTG (SEQ ID NO: 7)
CCTTGGGAGGGTCTCCTCAGATTGATTGACTGCCCACCTGGGGGGTCTTTCATTTGGAGGTTCCACCGAGATCAGGA

GACCCCTGCCCAGGGACCACCGACCCCCGCCGGGAGGTAAGCTGGCCAGCGGTCGTTTCGTGTCTGTCTCTGTCTCCG

TGCGTGTTTGTGCCGGCATCTAATGTTTGCGCCTGCGTCTGTACTAGTTGGCTAACTAGATCTGTATCTGGCGGTTCC

GCGGAAGAACTGACGAGTTCGTATTCCCGGCCGCAGCCCTGGGAGACGTCCCAGCGGCCTCGGGGGCCCGTTTTGTG

GCCCATTCTGTATCAGTTAACCTACCCGAGTCGGACTTTTTGGAGCTCCGCCACTGTACGTGGCTTTGTTGGGGACG

AGAGACAGAGACACTTCCCGCCCCCGTCTGGATTTTTGCTTTCGGTTTTACGCCGAAACCGCGCCGCGCGTCTG (SEQ ID NO: 8)
CCTTGGGAGGGTCTCCTCAGATTGATTGACTACCCACGTCGGGGTCTTTCATTTGGAGGTCCCACCGAGATTTGGAG

ACCCCTGCCCAGGGACCACCGATCCCCGCCGGGAGGTAAGCTGGCCAGCGGTCGTTTCGTGTCTGTCTCTGTCTTCG

TGCGTGTTTGTGCCGGCATCCAATGTTTGCGCCTGCGTCTGTACTAGTTAGCTAACTAGATCTGTATCTGGCGGTTCC

GCGGAAGAACTGACGAGTTCGTATTCCCGGCCGCAGCCCTGGGAGACGTCCCAGCGGCCTCGGGGGCCCGTTTTGTG

GCCCATTCTGTATCAGTTAACCTACCCGAGTCGGACTTTTTGGAGCTCCGCCACTGTACGTGGCTTTGTTGGGGACG

AGAGACAGAGACACTTCCCGCCCCCGTCTGAATTTTTGCTTTCGGTTTTATGCCGAAACCGCGCCGCGCGTCTG (SEQ ID NO: 9)
CCTTGGGAGGGTCTCCTCAGATTGATTGACTACCCACGTTCGGGGGTCTTTCATTTGGAGGTTCCACCGAGATTTGGA

GACCCATGCCCAGGGACCACCGACCCCCGCCGGGAGGTAAGCTGGCCAGCGGTCGTTTCGTGTCTGTCTCTGTCTCCG

TGCGTGTTTGTGCCGGCATCCAATGTTTGCGCCTGCGTCTGTACTAGTTAGCTAACTAGATCTGTATCTGGCGGTACC

GCGGAAGAACTGACGAGTTCGTATTCCCGGCCGCAGCCCTGGGAGACGTCCCAGCGGCCTCGGGGGCCCGTTTTGTG

GCCCATTCTGTATCAGTTAACCTACCCGAGTCGGACTTTTTGGAGCTCCGCCACTGTACGTGGCTTTGTTGGGGGACG

AGAGACAGAGACACTTCCCGCCCCCGTCTGAATTTTTGCTTTCGGTTTTATGCCGAAACCGCGCCGCGCGTCTG (SEQ ID NO: 10)
GTCTCCTCAGATTGATTGACTGCCCACCTGGGGGGGTCTTTCATTTGGAGGTTCCACCGAGATCAGGAGACCCCTGCC

CAGGGACCACCGACCCCCGCCGGGAGGTAAGCTGGCCAGCGGTCGTTTCGTGTCAGTCTCTGTCTCCGTGCGTGTTTG

TGCCGGCATCTAATGTTTGCGCCTGCGTCTGTACTAGTTGGCTAACTAGATCTGTATCTGGCGGGTCCGCGGAAGAAC

TGACGAGTTCGTATTCCCGGCCGCAGCCCTGGGAGACGTCCCAGCGGCCTCGGGGGCCCGTTTTGTGGCCCATTCTG

TATCAGTTAACCTACCCGAGTCGGACTTTTTGGAGCTCCGCCACTGTACGTGGCTTTGTTGGGGGACGAGAGACAGAG

ACACTTCCCGCCCCCGTCTGAATTTTTGCTTTCGGTTTTATGCCGAAACCGCGCCGCGCGTCTG (SEQ ID NO: 11)
CCTTGGGAGGGTCTCCTCAGATTGATTGACTACCCACGTCGGGGGTCTTTCATTTGGAGGTTCCACTGAGATTTGGAG

ACCCCTGCCCAGGGACCACCGACCCCCCGCCGGGAGGTAAGCTGGCCAGCGGTCGTTTCGTGTCTGTCTCTGTCTTCG

TGCGTGTTTGTGCCGGCATCCAATGTTTGCGCCTGCGTCTGTACTAGTTAGCTAACTAGATCTGTATCTGGCGGTTCC

GCGGAAGAACTGACGAGTTCGTATTCCCGGCCGCAGCCCTGGGAGACGTCCCAGCGGCCTCGGGGGCCCGTTTTGTG

GCCCATTCTGTATCAGTTAACCTACCCGAGTCGGACTTTTTGGAGCTCCGCCACTGTACGTGGCTTTGTTGGGGGACG

AGAGACAGAGACACTTCCCGCCCCCGTCTGAATTTTTGCTTTCGGTTTTACGCCGAAACCGCGCCGCGCGTCTGAATC

G (SEQ ID NO: 12)
CCTTGGGAGGGTCTCCTCAGATTGATTGACTACCCACGTCGGGGGTCTTTCATTTGGAGGTTCCACCGAGATTTGGAG

ACCCCTGCCCAGGGACCACCGACCCCCGCCGGGAGGTAAGCTGGCCAGCGGTCGTTTCGTGTCTGTCTCTGTCTTCG

TGCGTGTTTGTGCCGGCATCCAATGTTTGCGCCTGCGTCTGTACTAGTTAGCTAACTAGATCTGTATCTGGCGGTTCC

GCGGAAGAACTGACGAGTTCGTATTCCCGGCCGCAGCCCTGGGAGACGTCCCAGCGGCCTCGGGGGCCCGTTTTGTG

GCCCATTCTGTATCAGTTAACCTACCCGAGTCGGACTTTTTGGAGCTCCGCCACTGTACGTGGCTTTGTTGGGGGCG

AGAGACAGAGACACTTCCCGCCCCCGTCTGGATTTTTGCTTTCGGTTTTACGCCGAAACCGCGCCGCGCGTCTG (SEQ ID NO: 13)
CCTTGGGAGGGTCTCCTCAGATTGATTGACTACCCACGTCGGGGGTCTTTCATTTGGAGGTTCCACCGAGATTTGGAG

ACCCCTGCCCAGGGACCACCGACCCCCCGCCGGGAGGTAAGCTGGCCAGCGGTCGTTTCGTGTCTGTCTCTGTCTTC

GTGCGTGTTTGTGCCGGCATCCAATGTTTGCGCCTGCGTCTGTACTAGTTAGCTAACTAGATCTGTATCTGGCGGTTC

CGCGGAAGAACTGACGAGTTCGTATTCCCGGCCGCAGCCCTGGGAGACGTCCCAGCGGCCTCGGGGGCCCGTTTTGT

GGCCCATTCTGTATCAGTTAACCTACCCGAGTCGGACTTTTTGGAGCTCCGCCACTGTACGTGGCTTTGTTGGGGGAC

GAGAGACAGAGACACTTCCCGCCCCCGTCTGAATTTTTGCTTTCGGTTTTACGCCGAAACCGCGCCGCGCGTCTG (SEQ ID NO: 14)
CCTTGGGAGGGTCTCCTCAGATTGATTGACTACCCACGTCGGGGGTCTTTCATTTGGAGGTCCCACCGAGATTTGGAG

ACCCCTGCCCAGGGACCACCGACCCCCCGCCGGGAGGTAAGCTGGCCAGCGGTCGTTTCGTGTCTGTCTCTGTCTTC

GTGCGTGTTTGTGCCGGCATCCAATGTTTGCGCCTGCGTCTGTACTAGTTAGCTAACTAGATCTGTATCTGGCGGTTC

CGCGGAAGAACTGACGAGTTCGTATTCCCGGCCGCAGCCCTGGGAGACGTCCCAGCGGCCTCGGGGGCCCGTTTTGT

GGCCCATTCTGTATCAGTTAACCTACCCGAGTCGGACTTTTTGGAGCTCCGCCACTGTACGTGGCTTTGTTGGGGGAC

GAGAAACAGAGACACTTCCCGCCCCCGTCTGAATTTTTGCTTTCGGTTTTACGCCGAAACCGCGCCGCGCGTCTGA

-continued (SEQ ID NO: 15)
TCTCCTCAGATTGATTGACCACCCACCTCGGGGGTCTTTCATTTGGAGGTTCCACCGAGATTAGGAGACCCCTGCCCA

GGGACCACCGACCCCCGCCGGGAGGTAAGCTGGCCAGCGGTCGTTTCGTGTCTGTCTCTGTCTCCGTGCGTGTTTGTG

CCGGCATCTAATGTTTGCGCCTGCGTCTGTACTAGTTGGCTAACTAGATCTGAATCTGGCGGTTCCGTGGAAGAACTG

ACGAGTTCATATTCCCGGCCGCAGCCCTGGGAGACGTCTCAGAGGCATCGGGGGCCATCTTTGTGGCCCAATCTGTAT

CTGAGAACCCGACCCGTCTCGGACTCCTTGGAGCCTCTCCTTTGACCGAGGGATACGTGGTTCTGTTGGGCGGCGAGG

GGCCGAAACGCTCCTCTCCCCATCTGAATTTTTGCTTTCGGTTT (SEQ ID NO: 16)
CCTTGGGAGGGTCTCCTCAGATTGATTGACTACCCACGTCGGGGTCTTTCATTTGGAGGTTCCACTGAGATTTGGAG

ACCCCTGCCCAGGGACCACCGACCCCCGCCGGGAGGTAAGCTGGCCAGCGGTCGTTTCGTGTCTGTCTCTGTCTTCG

TGCGTGTTTGTGCCGGCATCCAATGTTTGCGCCTGCGTCTGTACTAGTTAGCTAACTAGATCTGTATCTGGCGGTTCC

GCGGAAGAACTGACGAGTTCGTATTCCCGGCCGCAGCCCTGGGAGACGTCCCAGCGGCCTCGGGGGCCCGTTTTGTG

GCCCATTCTGTATCAGTTAACCTACCCGAGTCGGACTTTTTGGAGCTCCGCCACTGTACGTGGCTTTGTTGGGGGACG

AGAGACAGAGACACTTCCCGCCCCCGTCTGAATTTTTGCTTTCGGTTTTACGCCGAAACCGCGCCGCGCGTCTG (SEQ ID NO: 17)
CCTTGGGAGGGTCTCCTCAGATTGATTGACTACCCACCGCGGGGTCTTTCATTTGGAGGTCCCACCGAGATTAGGAG

ACCCCTGCCCAGGGACCACCGACCCCCGCCGGGAGGTAAGCTGGCCAGCGGTCGTTTCGTGTCTGTCTCTGTCTCCAT

GCGTGTTGCGTGTTTGTGCCGGCATCTAATGTTTGCGCCTGCGTCTGTACTAGTTAGCTAACTAGATCTGAATCTGGC

GGTTCCGTGGAAGAACTGACGAGTTCATATTCCCGGCCGCAGCCCTGGGAGACGTCTCAGAGGCATCGGGGCCATCT

TTGTGGCCCAATCTGTATCTGAGAACCCGACCCGTCTCGGACTCTTGGAGCCTCTCCTTTGACCGAGGGATACGTGG

TTCTGTTGGGCGGCGAGGGGCCGAAACGCTCCTCCCCCCCATCTGAATTTTTGCTTTCGGTTTTCCGCCGAAACCGC

GCCGCGCGTCTG (SEQ ID NO: 18)
CCTTGGGAGGGTCTCCTCAGATTGATTGACCACCCACCTCGGGGTCTTTCATTTGGAGGTTCCACCGAGATTAGGAG

ACCCCTGCCCAGGGACCACCGACCCCCGCCGGGAGGTAAGCTGGCCAGCGGTCGTTTCGTGTCTGTCTCTGTCTCCGT

GCGTGTTTGTGCCGGCATCTAATGTTTGCGCCTGCGTCTGTACTAGTTGGCTAACTAGATCTGAATCTGGCGGTTCCG

TGGAAGAACTGACGAGTTCATATTCCCGGCCGCAGCCCTGGGAGACGTCTCAGAGGCATCGGGGGCCATCTTTGTGGC

CCAATCTGTATCTGAGAACCCGACCCGTCTCGGACTCCTTGGAGCCTCTCCTTTGACCGAGGGATACGTGGTTCTGTT

GGGCGGCGAGGGGCCGAAACGCTCCTCTCCCCCATCTGAATTTTTGCTTTCGGTTTTCCGCCGAAACCGCGCCGCGCG

TCTG (SEQ ID NO: 19)
CCTTGGGAGGGTCTCCTCAGATTGATTGACCACCCATCTCGGGGTCTTTCATTTGGAGGTTCCACCGAGATTAGGAG

ACCCCTGCCCAGGGACCACCGACCCCCGCCGGGAGGTAAGCTGGCCAGCGGTCGTTTCGTGTCTGTCTCTGTCTCCGT

GCGTGTTTGTGCCGGCATCTAATGTTTGCGCCTGCGTCTGTACTAGTTGGCTAACTAGATCTGAATCTGGCGGTTCCG

TGGAAGAACTGACGAGTTCATATTCCCGGCCGCAGCCCTGGGAGACGTCTCAGAGGCATCGGGGGCCATCTTTGTGGC

CCAATCTGTATCTGAGAACCCGACCCGTCTCGGACTCCTTGGAGCCTCTCCTTTGACCGAGGGATACGTGGTTCTGTT

GGGCGGCGAGGGGCCGAAACGCTCCTCTCCCCCATCTGAATTTTTGCTTTCGGTTTTCCGCCGAAACCGCGCCGCGCG

TCTG (SEQ ID NO: 20)
CCTTGGGAGGGTCTCCTCAGATTGATTGACTACCCACGTCGGGGTCTTTCATTTGGAGGTCCCACCGAGATTTGGAG

ACCCCTGCCCAGGGACCACCGATCCCCGCCGGGAGGTAAGCTGGCCAGCGGTCGTTTCGTGTCTGTCTCTGTCTTCG

TGCGTGTTTGTGCCGGCATCCAATGTTTGCGCCTGCGTCTGTACTAGTTAGCTAACTAGATCTGTATCTGGCGGTTCC

GCGGAAGAACTGACGAGTTCGTATTCCTGGCCGCAGCCCTGGGAGACGTCCCAGCGGCCTCGGGGGCCCGTTTTGTG

-continued

GCCCATTCTGTATCAGTTAACCTACCCGAGTCGGACTTTTTGGAGCTCCGCCACTGTACGTGGCTTTGTTGGGGACG

AGAGACAGAGACACTTCCCGCCCCC (SEQ ID NO: 21)
CCTTGGGAGGGTCTCCTCAGATTGATTGACTACCCACCTCGGGGGTCTTTCATTTGGAGGTCCCACCGAGATTAGGAG

ACCCCTGCCCAGGGACCACCGACCCCCGCCGGGAGGTAAGCTGGCCAGCGGTCGTTTCGTGTCTGTCTCTGTCTCCGT

GCGTGTTTGTGCCGGCATCTAATCTTTGCGCCTGCGTCTGTACTAGTTGGCTAACTAGATCTGTATCTGGCGGTTCCG

CGGAAGAACTGACGAGTTCGTATTCCCGGCCGCAGCCCTGGGAGACGTCCCAGCGGCCTCGGGGGCCCGTTTTGTGGC

CCATTCTGTATCAGTTAACCTGCCCGAGTCGGATTTTTTGGAGCTCCTCCACTGTCCGAGGGGTACGTGGCTTTGTC

GGGGGACGAGAGGCAGAGACACTTCCCTCCCCCGTCTGAATTTTTGCTTTCGGTTTTACGCCGAAACCGCGCCGCGCG

TC (SEQ ID NO: 22)
CCTTGGGAGGGTCTCCTCAGATTGATTGACTACCCACCGCGGGGGTCTTTCATTTGGAGGTCCCACCGAGATTAGGAG

ACCCCTGCCCAGGGACCACCGACCCCCGCCGGGAGGTAAGCTGGCCAGCGGTCGTTTCGTGTCTGTCTCTGTCTCCGT

GCGTGTTGCGTGTTTGTGCCGGCATCTAATGTTTGCGCCTGCGTCTGTACTAGTTAGCTAACTAGATCTGAATCTGGC

GGTTCCGTGGAAGAACTGACGAGTTCATATTCCCGGCCGCAGCCCTGGGAGACGTCTCAGAGGCATCGGGGCCATCT

TTGTGGCCCAATCTGTATCTGAGAACCCGACCCGTCTCGGACTCTTTGGAGCCTCTCCTTTGACCGAGGGATACGTGG

TTCTGTCGGCGGCGAGGGGCCGAAGCGCTCCTCCCCCCCCATCTGAATTTTTGCTTTCGGTTTTCCGCCGAAACCGC

GCCGCGCGTCTGACCTCCTTGGGAGGGTCTCCTCAGTTGCGGTGAGCCGAAACCGCGCCGCGCGTCTG (SEQ ID NO: 23)
CCTTGGGAGGGTCTCCTCAGATTGATTGACTACCCACCGCGGGGTCTTCCATTTGGAGGTCCCACCGAGATTAGGAG

ACCCCTGCCCAGGGACCACCGACCCCCGCCGGGAGGTAAGCTGGCCAGCGGTCGTTTCGTGTCTGTCTCTGTCTCCGT

GCGTGTTGCGTGTTTGTGCCGGCATCTAATGTTTGCGCCTGCGTCTGTACTAGTTAGCTAACTAGATCTGAATCTGGC

GGTTCCGTGGAAGAACTGACGAGTTCATATTCCCGGCCGCAGCCCTGGGAGACGTCTCAGAGGCATCGGGGCCATCT

TTGTGGCCCAATCTGTATCTGAGAACCCGACCCGTCTCGGACTCTTTGGAGCCTCTCCTTTGACCGAGGGATACGTGG

TTCTGTTGGGCGGCGAGGGGCCGAAACGCTCCTCCCCCCCCATCTGAATTTTTGCTTTCGGTTTTCCGCCGAAACCGC

GCCGCGCG (SEQ ID NO: 24)
CCTTGGGAGGGTCTCCTCAGATTGATTGACCACCCACCTCGGGGTCTTTCATTTGGAGGTTCCACCGAGATTAGGAG

ACCCCTGCCCAGGGACCACCGACCCCCGCCGGGAGGTAAGCTGGCCAGCGGTCGTTTCGTGTCTGTCTCTGTCTCCGT

GCGTGTTTGTGCCGGCATCTAATGTTTGCGCCTGCGTCTGTACTAGTTGGCTAACTAGATCTGAATCTGGCGGTTCCG

TGGAAGAACTGACGAGTTCATATTCCCGGCCGCAGCCCTGGGAGACGTCTCAGAGGCATCGGGGCCATCTTTGCGGC

CCAATCTGTATCTGAGAACCCGACCCGTCTCGGACTCCTTGGAGCCTCTCCTTTGACCGAGGGATACGTGGTTCTGTT

GGGCGGCGAGGGGCCGAAACGCTCCTCTCCCCCATCTGAATTTTTGCTTTCGGTTTTCCGCCGAAACCGCGCCGCGCG

TCTG (SEQ ID NO: 25)
CCTTGGGAGGGTCTCCTCAGATTGATTGACCACCCACCTCGGGGTCTTTCATTTGGAGGTTCCACCGAGATTAGGAG

ACCCCTGCCCAGGGACCACCGACCCCCGCCGGGAGGTAAGCTGGCCAGCGGTCGTTTCGTGTCTGTCTCTGTCTCCGC

GCGTGTTTGTGCCGGCATCTAATGTTTGCGCCTGCGTCTGTACTAGTTGGCTAACTAGATCTGAATCTGGCGGTTCCG

TGGAAGAACTGACGAGTTCATATTCCCGGCCGCAGCCCTGGGAGACGTCTCAGAGGCATCGGGGCCATCTTTGTGGC

CCAATCTGTATCTGAGAACCCGACCCGTCTCGGACTCCTTGGAGCCTCTCCTTTGACCGAGGGATACGTGGTTCTGTT

GGGCGGCGAGGGGCCGAAACGCTCCTCTCCCCCATCTGAATTTTTGCTTTCGGTTTTCCGCCGAAACCGCGCCGCGCG

TCTG (SEQ ID NO: 26)
CCTTGGGAGGGTCTCCTCAGATTGATTGACTACCCACCGCGGGGGTCTTTCATTTGGAGGTCCCACCGAGATTAGGAG

ACCCCTGCCCAGGGACCACCGACCCCCGCCGGGAGGTAAGCTGGCCAGCGGTCGTTTCGTGTCTGTCTCTGTCTCCGT

GCGTGTTGCGTGTTTGTGCCGGCATCTAATGTTTGCGCCTGCGTCTGTACTAGTTAGCTAACTAGATCTGAATCTGGC

GGTTCCGTGGAAGAACTGACGAGTTCATATTCCCGGCCGCAGCCCTGGGAGACGTCTCAGAGGCATCGGGGGCCATCT

TTGTGGCCCAATCTGTATCTGAGAACCCGACCCGTCTCGGACTCTTTGGAGCCTCTCCTTTGACCGAGGGATACGTGG

TTCTGTTGGGCGGCGAGGGGCCGAAACGCTCCTCCCCCCCCATCTGAATTTTTGCTTTCGGTTTTCCGCCGAAACCGC

GCCGCGCGTCCG (SEQ ID NO: 27)
CCTTGGGAGGGTCTCCTCAGATTGATTGACTACCCACCGCGGGGGTCTTTCATTTGGAGGTCCCACCGAG

ATTAGGAGACCCCTGCCCAGGGACCACCGACCCCCGCCGGGAGGTAAGCTGGCCAGCGGTCGTTTCGTGT

CTGTCTCTGTCTCCGTGCGTGTTGCGTGTTTGTGCCGGCATCTAATGTTTGCGCCTGCGTCTGTACTAGT

TAGCTAACTAGATCTGAATCTGGCGGTTCCGTGGAAGAACTGACGAGTTCATATTCCCGGCCGCAGCCCT

GGGAGACGTCTCAGAGGCATCGGGGGCCATCTTTGTGGCCCAATCTGTATCTGAGAACCCGACCCGTCTC

GGACTCTTTGGAGCCTCTCCTTTGACCGAGGGATACGTGGTTCTGTTGGGCGGCGAGGGGCCGAAACGCT

CCTCCCCCCCCATCTGAATTTTTGCTTTCGGTTTTCCGCCGAAACCGCGCCGCGCGTCTG

In some embodiments, a BPH virus polynucleotide of use in the methods disclosed herein has a sequence at least 75% (such as at least 80%, 85%, 90%, 95%, 96%, 97%, 98%, 99%, or more) identical to the nucleic acid sequence set forth in one of SEQ ID NOs: 1-27. Exemplary sequences can be obtained using computer programs that are readily available on the internet and the nucleic acid sequences set forth herein. In some examples, the BPH virus polynucleotide is a BV1 BPH virus polynucleotide (such as SEQ ID NOs: 1-16) or a BV2 BPH virus polynucleotide (such as SEQ ID NOs: 17-27).

In other examples, the polynucleotide is an envelope (env) nucleic acid sequence, for example, comprising or consisting of the nucleic acid sequence set forth as:

(SEQ ID NO: 28)
CCTCAACCTCACCAGTCCCGACAAAACCCAAGAGTGCTGGTTGTGTCTGGTATCGGGACCCCCCTACTACGAAGGGGT

TGCCGTCCTAGGTACCTACTCCAACCATACCTCTGCCCCAGCTAACTGCTCCGTGGCCTCCCAACACAAGCTGACCCT

GTCCGAAGTGACCGGACAGGGACTCTGCGTAGGAGCAGTTCCCAAAACCCATCAGGCCCTGTGTAATACCACCCAGAA

GACGAGCGACGGGTCCTACTATCTGGCTGCTCCCGCCGGGACCATCTGGGCTTGCAACACCGGGCTCACTCCCTGCCT

ATCTACTACTGTACTCAACCTCACCACCGATTACTGTGTCCTGGTTGAGCTCTGGCCAAAGGTGACCTACCACTCCCC

TGGTTATGCTTATGGCCAGTTTGAGAGAAAAACCAAATATAAAAGAGAGCCGGTGTCATTAACTCTGGCCCTGCTGTT

GGGAGGACTTACTATGGGCGGCATAGCTGCAGGAGTAGGAACAGGGACTACAGCCCTAGTGGCCACCAAACAATTCGA

GCAGCTCCAGGCAGCCATACATACAGACCTTAGGGCCTTAGAAAAATCAGTCAGTGCCCTAGAAAAGTCTCTGACCTC

GTTGTCTGAGGTGGTCCTACAGAACCGGAGAGGATTAGATCTGCTGTTCCTAAAAGAAGGAGGATTATGTGCTGCCCT

AAAAGAAGAATGCTGTTTCTACGCGGACCACACTGGCGTAGTGAGAGATAGCATGGCAAAGCTAAGAGAAAGGTTAAA

CCAGAGACAAAAATTGTTCGAATCAGGACAAGGGTGGTTTGAGGGACTGTTTAACAGGTCCCCATGGTTCACGACCTT

GATATCCACCATTATGGGCCCCTTGATAATACTTTTATTAATCCTACTCCTCGGACCCTGTATTCTCAACCGCTTGGT

CCAGTTTGTAAAAAAAGAATTTCGGGGGGGCAGGCCCTGGTTCTGACCCACAGTATCCCCACTCAATTAATAAATCCC

AAAAAAAAGGCGTCCCTGCAGAAAAAATTTATTATTTTTCCGG (SEQ ID NO: 29)
CCATGCCTTGCAAAATGGCGTTACTGCAGCTAGCTTGCTAAGCCTGATGGTGGGGTCTTTCATTCCCCCCTCTTTCTG

GAAACTGAATAAAATCTTTTATTCACGTGATTCCACTTCTTCTGGATCTATTGATTTGAGTTGGTGATACTGTTGGGT

CAAAGCCAGGGCCTGCACTACCGAAATTCTGTCTTTTACAAACTGGACCAAGCGGTTGAGAATACAGGGTCCGAAGAG

TAGGATTAATAAAAGTATTATCAAGGGGCCCATAATGGTAGATATTAAGGTCGTGAACCATGGGGACCTGTTAAACAG

-continued

```
TCCCTCAGACCACCCTTGTCCTGATTCGAACAATTTTTGTCTCTGGTTCAACCTTTCTCTTAGCTTTGCCATGCTATC

TCTTACTACGCCAGTGTGGTCCGCGTAGAAACAGCATTCTTCTTTTAGGGCAGCACATAATCCTCCTTCTTTTAGGAA

CAGTAGATCTAATCCCCTCCGGTTCTGTAGGACCACCTCAGACAACGAGGTCAGAGACTTTTCTAGGGCACTGACTGA

CTTTTCTAAAGCCCCAAGGTCTGTATGTATGGCTGCCTGGAGCTGCTCGAATTGTTTGGTGGCCACTAGGGCTGTAGT

CCCGGTTCCTACTCCTGCAGCTATGCCGCCCATAGTAAGTCCTCCCAACAGCAGGGCCAGAGTTAATGACACCGGCTC

TCTTTTATATTTGGTTTTTTTCTCAAACTGGCCATAAACATAACCAGGGGAGTGGTAGGTCACCTTTGGCCAGAGCTC

AACCAGGACACAGTAATCGGTGGTTAAGTTAAGCACAGTAGTAGATAGACAGGGAGTGAGCCCGGTGCTGCAGGCCCA

AATGGTCCCGGCGGGAGAGGCCAAATAGTAGGACCCGTCGCTCGTCTTCTGGGTGGTATTACACAGGGCCTGATGGGG

TTTTGGGGAACTGCTCCTACGCAGAAACCCTGGTCCGGTCCCTTCGGACAGGGTCACCTTGGGTTGGGGAGGCCCGGA

ACAGTTAGCTGGGGCAAAAAAAGGGTGGGAAAAGGTACC
```

In some embodiments, a BPH virus polynucleotide of use in the methods disclosed herein has a sequence at least 90% (such as at least 91%, 92%, 93%, 94%, 95%, 96%, 97%, 98%, 99%, or more) identical to the nucleic acid sequence set forth in one of SEQ ID NOs: 28 or 29. Exemplary sequences can be obtained using computer programs that are readily available on the internet and the nucleic acid sequences set forth herein.

In other examples, the polynucleotide is a variable region nucleic acid sequence, for example, comprising or consisting of the nucleic acid sequence set forth as:

(SEQ ID NO: 30)

GGGACGATGACAGACACTTTCCCTAAACTATATTTTGACTTGTGTGGTTTAGTTGGAGATAACTGGGATGACCCGGAA

TCCTCTAGTGGACATGGTTGCCGCTCTCCCGGGGGAAGAAAAGGGACAAGAACATTTGATTTCTATGTTTGCCCCGGT

CATACTGTACTAACAGGGTGTGGAGGGCCGAGGGAGGGCTACTGTGGCAAATGGGGATGTGAGACCACTGGACAGGCA

TACTGGAAGCCATCATCATCATGGGACCTAATTTCCCTTAAGCGAGGAAACACTCCTAGGAGTCAGGGCCCCTGTTAT

GATTCCTCAGTGGTCTCCAGTAGCGTCCAGGGTGCCACACCGGGGGGTCGATGCAACCCCCTAGTCCTAGAATTCACT

GACGCGGGTAA (SEQ ID NO: 31)

GGGACGATGACAGACACTTTCCCTAAACTATATTTTGACTTGTGTGATTTAGTTGGAGATAACTGGGATGACCCGGAA

TCCTCTAGTGGACATGGTTGCCGCTCTCCCGGGGGAAGAAAAAGGACAAGAACATTTGATTTCTATGTTTGCCCCGGT

CATACTGTACTAACAGGGTGTGGAGGGCCGAGGGAGGGCTACTGTGGCAAATGGGGATGTGAGACCACTGGACAGGCA

TACTGGAAGCCATCATCATCATGGGACCTAATTTCCCTTAAGCGAGGAAACACTCCTAGGAGTCAGGGCCCCTGTTAT

GATTCCTCAGTGGTCTCCAGTAGCGTCCAGGGTGCCAC (SEQ ID NO: 32)

TACCCGCGTCAGTGAATTCTAGGACTAGGGGGTTGCATCGACCCCCCGGTGTGGCACCCTGGACGCCACTGGAGACCG

AGGAATCATAACAGGGGCCCTGATCCTTAGGAGTGTTTCCTCGCTTAAGGGAAATTAGGTCCCATGATGATGATGGCT

TCCAGTATGCCTGTCCAGTGGTCTCACATCCCCATTTGCCACAGTAGCCCTCTCCCGGCCCTCCACACCCTATTGGTA

CAGTATGACCGGGGCAAACATAGAAGTCATACAGTCTTGTCCTTTTTCTTCCCCCGGGAGAGCGGCAACCATCTCCAT

CTGGGTCATCCCAATCCCAGTAGTCTCCTACTAAATCACACAGGTCAAAATATAGTTTAGGGAAAGTGTCTGTCATCG

TCCC (SEQ ID NO: 33)

TACCCGCGTCAGTGAATTCTAGGACTAGGGGGTTGCATCGACCCCCCGGTGTGGCACCCTGGACGTCACTGGAGACCG

AGGAATCATAACAGGGGCCCTGATCCTTAGGAGTGTTTCCTCGCTTAAGGGAAATTAGGTCCCATGATGATGATGGCT

TCCAGTATGCCTGTCCAGTGGTCTCACATCCCCATTTGCCACAGTAGCCCTCTCTCGGCCCTCCACACCCTATTGGTA

CAGTATGACCGGGGCAAACATAGAAGTCATACAGTCTTGTCCTTTTTCTTCCCCCGGGAGAGCGGCAACCATCTCCAT

CTGGGTCATCCCAGTAGTCTCCTACTAAATCACACAGGTCAAAATATAGTTTAGGGAAAGTGTCTGTCATCGTCCC

In some embodiments, a BPH virus polynucleotide of use in the methods disclosed herein has a sequence at least 90% (such as at least 91%, 92%, 93%, 94%, 95%, 96%, 97%, 98%, 99%, or more) identical to the nucleic acid sequence set forth in one of SEQ ID NOs: 30-33. Exemplary sequences can be obtained using computer programs that are readily available on the internet and the nucleic acid sequences set forth herein.

In other examples, the polynucleotide is an androgen response element nucleic acid sequence, for example, comprising or consisting of the nucleic acid sequence set forth as:

```
                                                            (SEQ ID NO: 34)
GGGAGCAAAAAGCGCGGGTACAGAAGCGAGAAGCGAGCTGATTGGTTAGTTTAAATGAGGCTTGGGGTTGATCCCCGG

TCATCTGGGGAACCTTGAGACAGTTTCTGGGTCTCTTGAAACTGTTGTTGTTTTAGCTATTTCTGGGGACCATCTGTT

CTTGGCCCTGGGCCGGGGCCCTAGTGCTTGACCACAGATACCCTGTTTGGCCCTAGTCCCGGTACTTTCCAGCCTCTC

TGTACTTCCTTGTTCTTGTTTTTCTGAGAACATCAGCTCTGGTATTTTCCCATGCCTTGCAAAATGGCG (SEQ ID NO: 35)
CGCCATTTTGCAAGGCATGGAAAAGTACCAGAGCTGAGTTCTCAAAAGTTACAAGGAAGTTCAGTTAAAGATTAACAG

TTAAAAATCAAGGCTGAATAATACTAGGACAAGGGCCAAGAACCGATGGTACCCACCGGGGCCCCGGCTCAAGGCCAA

GAACCGATGGTACCCACCTGGGCCCCGGCTCAGGGCCAAGAACAGATGGTACCCAGATAAGGCGGAACCAGCAACAGT

TTCTAAAAAAGTCCCACCTCAGTTTCAGGTTCCCCAAATGACCAGGAAATACCCCAAGCCTTGATTTGAACTAACCAC

TCAGCTCGCTTCTCGCTTCTGTACCCGCGCTTTTTGCTCCCC (SEQ ID NO: 36)
CGCCATTTTGCAAGGCATGGCAAAAGTACCAGAGCTGAGTTCTCAAAAGTTACAAGAAAGTTCAGTTAAAGATTAACA

GTTAAAGATTAAGGCTGAATAATACTGGGACAGGGGCCAAATATCGGTGGTCAAGCACCTGGGCCCCGGCTCAGGGCC

AAGAACAGATGGCTCTCAGACGTCAGTGTTAGCAGAACTAGCTTCACTGATTTAGAAAAATAGAGGTGCACAATGCTC

TGGCCACTCCTTGAACCTGTGTGTCTGCCAATGTTCTGACCAGGTGTGTGCCCATTGCTGCACCTTCATTAGACTCTT

TCCTTGTACCCCTCCCATACCCATTTCTTGAAAATAGACATTGTTTAGATCTAAAAAGTTCCACCTCAGTTTCAGGTT

CCCCAAATGACCGGAAAATACCCCAAACCTTATTTGAACTAACCAACCAGCTCGCTTCTTGCTTCTGTACCCGCGCTT

TTTGCTCCC (SEQ ID NO: 37)
CGCCATTTTGCAAGGCATGGAAAAGTACTAGAGCTGAGACCTCAAAAGTTACAAGGAAGTTCAGTTAAAGTTTAAGGC

TAAATAACAACGGGACAGGGGCCAAACAGGATATCTATGGTCAAGCACCTGGGCCCCGGCTCAGGGCCAAGAACAGAT

GGTACCCAGATAGAGCGGAACCAGCAACAGTTTCGAGACTGCCCCACCAGCCAAGAACAGATGGTACCCAGATAGAGC

GGAACCAGCAACAGTTTCGAGACTGCCCCACATCAGTTTCAAGGTTCCCCAAATGGCCGGGACTTTCCCCTAGCCTTA

TTTGAACTAACCAATCAGCTCGCTTCTCGCTTCTGTACCCGCGCTTTTTGCTCCC (SEQ ID NO: 38)
GGGAGCAAAAAGCGCGGGTACAGAAGCGAGAAGCGAGCTGATTGGTTAGTTTAAATAAGGCTTGGGGTATTTCCCGGT

CATTTGGGGAACCTGAAACTGAGGTGGGACTTTCCAGAAACTGTTGCTAGTTTCGCTTTATCTGAGTACCATCTGTTC

TTGGCCCTGAGCCGGGGCCCAGGTGCTTGACCACAGATATCCTGTTTGGCCCCTGTCCCAGTATTATTCAGCCTTATT

CTTTAACTAAACTTCCTTGTAACTTTTGAGAACTCAGCTCTGGTACTTTTCCATGCCTTGCAAAATGGCG
```

In some embodiments, a BPH virus polynucleotide of use in the methods disclosed herein has a sequence at least 90% (such as at least 91%, 92%, 93%, 94%, 95%, 96%, 97%, 98%, 99%, or more) identical to the nucleic acid sequence set forth in one of SEQ ID NOs: 34-38. Exemplary sequences can be obtained using computer programs that are readily available on the internet and the nucleic acid sequences set forth herein.

In some examples, a nucleic acid sequence can be utilized to differentiate between BPH virus and another retrovirus (such as XMRV). In one example, a variable region nucleic acid sequence is used to specifically identify a BPH virus. In some examples, a BPH virus differs from another retrovirus (such as XMRV) at one or more of positions 60, 79, 82, 83, 91, 130, 134, 166, 189, 293, 295, 311, 326, 331, and/or 337 of SEQ ID NO: 30. In specific, non-limiting examples, a BPH virus differs from another retrovirus (such as XMRV) at one or more of positions 12, 27, 49, 52, 55, 60, 65, 75, 95, 97, 98, 111, 116, 120, 127, 130, 132, 145, 154, 171, 172, and/or 174 of SEQ ID NO: 10 or at one or more of positions 22, 37, 58, 61, 64, 69, 74, 84, 104, 106, 107, 120, 125, 129, 136, 139, 141, 154, 163, 187, 188, and/or 190 of SEQ ID NO: 17 (for example, see FIG. 6).

In other examples, a BPH virus nucleic acid sequence can be utilized to differentiate between subtypes of BPH virus (such as BV1 and BV2 BPH virus subtypes). In one example, a gag or glyco-gag BPH virus nucleic acid is used to specifically identify a BPH virus subtype. In specific, non-limiting examples, BV1 BPH virus differs from BV2 BPH virus at one or more of positions 12, 22, 27, 30, 49, 52, 55, 56, 60, 64, 65, 75, 95, 97, 98, 111, 116, 120, 127, 130, 132, 133, 144-146, 154, 171, 172, 174, 196, 221, 261, 345,-361, and/or 431 of SEQ ID NO: 10 and/or one or more of positions 22, 32, 37, 58, 61, 62, 64, 65, 69, 74, 84, 104, 106, 107, 120, 125, 129, 136, 139, 141, 153-155, 163-166, 170, 187, 188, 190, 227, 242, 261, 291, 295, 299, 309-311, 323, 332, 334, 335, 340, 341, 347, 348, 356, 361-386, 391, 393, 401, 403, 408, 410, 412, 415, 418, 420, 422, 425, 431, and/or 455 of SEQ ID NO: 17 (for example, see FIG. 6).

The disclosed polynucleotides (such as polynucleotides encoding a BPH virus gag or gag-related protein or envelope protein) include a recombinant DNA which is incorporated into a vector, into an autonomously replicating plasmid or virus, or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single- and double-stranded forms of DNA.

In one embodiment, vectors are used for expression in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (such as AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation.

Viral vectors including the disclosed polynucleotides (such as polynucleotides encoding a BPH virus gag or gag-related protein or envelope protein) can also be prepared. A number of viral vectors have been constructed, including polyoma, SV40 (Madzak et al., 1992, *J. Gen. Virol.,* 73:15331536), adenovirus (Berkner, 1992, *Curr. Top. Microbiol. Immunol.,* 158:39-6; Berliner et al., 1988, *BioTechniques,* 6:616-629; Gorziglia et al., 1992, *J. Virol.,* 66:4407-4412; Quantin et al., 1992, *Proc. Natl. Acad. Sci. USA,* 89:2581-2584; Rosenfeld et al., 1992, *Cell,* 68:143-155; Wilkinson et al., 1992, *Nucl. Acids Res.,* 20:2233-2239; Stratford-Perricaudet et al., 1990, *Hum. Gene Ther.,* 1:241-256), vaccinia virus (Mackett et al., 1992, *Biotechnology,* 24:495-499), adeno-associated virus (Muzyczka, 1992, *Curr. Top. Microbiol. Immunol.,* 158:91-123; On et al., 1990, *Gene,* 89:279-282), herpes viruses including HSV and EBV (Margolskee, 1992, *Curr. Top. Microbiol. Immunol.,* 158:67-90; Johnson et al., 1992, *J. Virol.,* 66:2952-2965; Fink et al., 1992, *Hum. Gene Ther.* 3:11-19; Breakfield et al., 1987, *Mol. Neurobiol.,* 1:337-371; Fresse et al., 1990, *Biochem. Pharmacol.,* 40:2189-2199), Sindbis viruses (Herweijer et al., 1995, *Hum. Gene Ther.* 6:1161-1167; U.S. Pat. Nos. 5,091,309 and 5,2217,879), alphaviruses (S. Schlesinger, 1993, *Trends Biotechnol.* 11:18-22; Frolov et al., 1996, *Proc. Natl. Acad. Sci. USA* 93:11371-11377) and retroviruses of avian (Brandyopadhyay et al., 1984, *Mol. Cell Biol.,* 4:749-754; Petropouplos et al., 1992, *J. Virol.,* 66:3391-3397), murine (Miller, 1992, *Curr. Top. Microbiol. Immunol.,* 158:1-24; Miller et al., 1985, *Mol. Cell Biol.,* 5:431-437; Sorge et al., 1984, *Mol. Cell Biol.,* 4:1730-1737; Mann et al., 1985, *J. Virol.,* 54:401-407), and human origin (Page et al., 1990, *J. Virol.,* 64:5370-5276; Buchschalcher et al., 1992, *J. Virol.,* 66:2731-2739). Baculovirus (Autographa californica multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Thus, in one embodiment, a polynucleotide encoding a BPH virus polypeptide is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like.

Basic techniques for preparing recombinant DNA viruses containing a heterologous DNA sequence are known in the art. Such techniques involve, for example, homologous recombination between the viral DNA sequences flanking the DNA sequence in a donor plasmid and homologous sequences present in the parental virus (Mackett et al., 1982, *Proc. Natl. Acad. Sci. USA* 79:7415-7419). In particular, recombinant viral vectors such as a poxviral vector can be used in delivering the gene. The vector can be constructed for example by steps known in the art, such as steps analogous to the methods for creating synthetic recombinants of the fowlpox virus described in U.S. Pat. No. 5,093,258, incorporated herein by reference. Other techniques include using a unique restriction endonuclease site that is naturally present or artificially inserted in the parental viral vector to insert the heterologous DNA.

DNA sequences encoding a BPH virus polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

As noted above, a polynucleotide sequence encoding a BPH virus polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (e.g., ATG) in front of a protein-encoding gene, splicing signal for introns, maintenance of the correct reading frame of that gene to permit proper translation of mRNA, and stop codons.

Host cells can include microbial, yeast, insect and mammalian host cells. Methods of expressing DNA sequences having eukaryotic or viral sequences in prokaryotes are well known in the art. Non-limiting examples of suitable host cells include bacteria, archea, insect, fungi (for example, yeast), mycobacterium (such as *M. smegmatis*), plant, and animal cells (for example, mammalian cells, such as human). Exemplary cells of use include *E. coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), 1979, Cell Culture. *Meth. Enzymol*., volume 58, Academic Press, Inc., Harcourt Brace Jovanovich, N.Y.). Examples of commonly used mammalian host cell lines are VERO and HeLa cells, CHO cells, and WI38, BHK, and COS cell lines, although other cell lines may be used, such as cells designed to provide higher expression, desirable glycosylation patterns, or other features. As discussed above, techniques for the transformation of yeast cells, such as polyethylene glycol transformation, protoplast transformation and gene guns are also known in the art (see Gietz and Woods *Meth. Enzymol.* 350: 87-96, 2002).

Transformation of a host cell with recombinant DNA can be carried out by conventional techniques well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with a polynucleotide encoding a BPH virus polypeptide and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

B. BPH Virus Polypeptides

Polypeptides encoded by BPH virus polynucleotides disclosed herein are also provided. In some embodiments, the polypeptides include gag polypeptides or gag-related polypeptides (such as glyco-gag polypeptides), for example, comprising or consisting of the amino acid sequence set forth as:

(SEQ ID NO: 39)
LTSSYSRPQPLGDVPAASGARFVAHSVAVNLPESDFLELRHCTWLCWGTRDRDTSRPRLNFAFGFTPKPRRAS;

(SEQ ID NO: 40)
LTSSYSRPQPWETSQRPRGPVLWPILYQLTYPSRTFWSSSTVRGFVGGREAETLPSPVIFAFGFTPKPRRAS;

(SEQ ID NO: 41)
LTSSYSRPQPLGDVPAASGARFVAHSVSVNLPESDFLELRHCTCLCWGTRDRDTSRPRLDFCFRFYAETAPRV;

(SEQ ID NO: 42)
LTSSYSRPQPWETSQRHRGPSLWPNLYLRTRPVSDSLEPLLPRDTWFCWAARGRNAPPPPSEFLLSVFRRNRA;

(SEQ ID NO: 43)
LRSSYSRPQPLGDVPVASGARFVVHSVSLNLPESDFLELRHCTWVWWGTRDRDTSRPRLDFCFRLYAETAPRV;

(SEQ ID NO: 44)
LTSSYSRPQPLGDVPAASGARFVAHSVSVNLPESDFLELRHCTWLCWGTRDRDTSRPRLNFCFRFYAETAPRV;

(SEQ ID NO: 45)
LTSSYSRPQPLGDVPAASGARFVAHSVSVNLPESDFLELRHCTWLCWGARDRDTSRPRLDFCFRFYAETAPRV;

(SEQ ID NO: 46)
LTSSYSRPQPWETSQRHRGPSLWPNLYLRTRPVSDSLEPLLPRDTWFCWAARGRNAPLPHLNFCFRFXAETAPRV;

(SEQ ID NO: 47)
LTSSYSRPQPWETSQRHRGPSLWPNLYLRTRPVSDSLEPLLPRDTWFCWAARGRNAPLPHLNFCFRFSAETAPRV;

(SEQ ID NO: 48)
LTSSYSRPQPWETSQRPRGPVLWPILYQLTCPSRIFLELLHCPRGTWLCRGTRGRDTSLPRLNFCFRFYAETAPRV;

(SEQ ID NO: 49)
LTSSYSRPQPWETSQRHRGPSLWPNLYLRTRPVSDSLEPLLPRDTWFCRAARGRSAPPPPSEFLLSVFRRNRAARLTS
LGGSPQLRAETAPRV;

(SEQ ID NO: 50)
LTSSYSRPQPWETSQRHRGPSLRPNLYLRTRPVSDSLEPLLPRDTWFCWAARGRNAPLPHLNFCFRFSAETAPRV;

(SEQ ID NO: 51)
LTSSYSRPQPLGDVPAGSGARFVAHSVSVNLPESDFLELRHCTWLCWGTRDRDTSRPRLNFCFRXYAETAPRV;

(SEQ ID NO: 52)
LTSSYSRPQPLGDVPAASGARFVAHSVSVNLPESDFLELRHCTWLCWGTRDRDTSRPRLDFCFRFYAETAPRV;

(SEQ ID NO: 53)
LTSSYSRPQPLGDVPAASGARFVAHSVSVNLPESDFLELRHCTWLCWGTRDRDTSRPRLDFCFRFYAETAPRV;

(SEQ ID NO: 54)
LTSSYSWPQPLGDVPAASGARFVAHSVSVNLPESDFLELRHCTWLCWGTRDRDTSRPRLDFCFRFYAETAPRV wherein "X" indicates any amino acid.

In some embodiments, a BPH virus polypeptide of use in the methods disclosed herein has a sequence at least 75%, 80%, 85%, 90%, 95%, 96%, 97%, 98% or 99% identical to the amino acid sequence set forth in one of SEQ ID NOs: 39-54. Exemplary sequences can be obtained using computer programs that are readily available on the internet and the amino acid sequences set forth herein.

In other embodiments, the polypeptides include envelope polypeptides, for example, comprising or consisting of the amino acid sequence set forth as:

(SEQ ID NO: 55)
LNLTSPDKTQECWLCLVSGPPYYEGVAVLGTYSNHTSAPANCSVASQHKLTLSEVTGQGLCVGAVPKTHQALCNTTQK

TSDGSYYLAAPAGTIWACNTGLTPCLSTTVLNLTTDYCVLVELWPKVTYHSPGYAYGQFERKTKYKREPVSLTLALLL

GGLTMGGIAAGVGTGTTALVATKQFEQLQAAIHTDLRALEKSVSALEKSLTSLSEVVLQNRRGLDLLFLKEGGLCAAL

KEECCFYADHTGVVRDSMAKLRERLNQRQKLFESGQGWFEGLFNRSPWFTTLISTIMGPLIILLLILLLGPCILNRLV

QFVKKEFRGGRPWF (SEQ ID NO: 56)
GTFSHPFFAPANCSGPPQPKVTLSEGTGPGFLRRSSSPKPHQALCNTTQKTSDGSYYLASPAGTIWACSTGLTPCLST

TVLNLTTDYCVLVELWPKVTYHSPGYVYGQFEKKTKYKREPVSLTLALLLGGLTMGGIAAGVGTGTTALVATKQFEQL

QAAIHTDLGALEKSVSALEKSLTSLSEVVLQNRRGLDLLFLKEGGLCAALKEECCFYADHTGVVRDSMAKLRERLNQR

QKLFESGQGWSEGLFNRSPWFTTLISTIMGPLIILLLILLFGPCILNRLVQFVKDRISVVQALALTQQYHQLKSIDPE

EVESRE

In some embodiments, a BPH virus polypeptide of use in the methods disclosed herein has a sequence at least 90% (such as at least 91%, 92%, 93%, 94%, 95%, 96%, 97%, 98%, 99%, or more) identical to the amino acid sequence set forth in one of SEQ ID NOs: 55 and 56. Exemplary sequences can be obtained using computer programs that are readily available on the internet and the amino acid sequences set forth herein.

In other embodiments, the polypeptides include envelope variable region (VR) polypeptides, for example, comprising or consisting of the amino acid sequence set forth as:

(SEQ ID NO: 57)
GTMTDTFPKLYFDLCDLVGDNWDDPESSSGHGCRSPGGRKRTRTFDFYVCPGHTVLTGCGGPREGYCGKWGCETTGQA

YWKPSSSWDLISLKRGNTPRSQGPCYDSSVVSSSVQGATPGGRCNPLVLEFTDAG (SEQ ID NO: 58)
GTMTDTFPKLYFDLOGLVGDNWDDPESSSGHGCRSPGGREGTRTFDFYVCPGHTVLTGOGGPREGYOGEWGCETTGQA

YWKPSSSWDLISLKRGNTPRSQGPCYDSSVVSSSVQGATPGGRCNPLVLEFTDAG

In some embodiments, a BPH virus polypeptide of use in the methods disclosed herein has a sequence at least 90% (such as at least 91%, 92%, 93%, 94%, 95%, 96%, 97%, 98%, 99%, or more) identical to the amino acid sequence set forth in one of SEQ ID NOs: 57 or 58. Exemplary sequences can be obtained using computer programs that are readily available on the internet and the amino acid sequences set forth herein.

In some examples, a polypeptide sequence can be utilized to differentiate between BPH virus and another retrovirus (such as XMRV). In one example, a variable region amino acid sequence is used to specifically identify a BPH virus. In another example, a glyco-gag amino acid sequence is used to specifically identify a BPH virus. In specific, non-limiting examples, a BPH virus differs from another retrovirus (such as XMRV) at one or more of positions 27-29, 31, 44, 45, 98, 104, 109, 111, and 113 of SEQ ID NO: 57 or one or more of positions 16, 27-29, 31, 41, 44, 45, 98, 105, 109, 111, and 113 of SEQ ID NO: 58 (for example, as shown in FIG. 4A).

In other examples, a BPH amino acid sequence can be utilized to differentiate between subtypes of BPH virus (such as BV1 and BV2 BPH virus subtypes). In one example, a gag or glyco-gag BPH virus polypeptide is used to specifically identify a BPH virus subtype. In specific, non-limiting examples, a BV1 virus differs from a BV2 virus at one or more of positions 2, 11-18, 20-31, 33, 36, 40-42, 45-46, 48-49, 51, 53-56, 58, 60, 65, and/or 66 of SEQ ID NO: 41. In other specific, non-limiting examples, a BV2 virus differs from a BV1 virus at one of more of positions 2, 11-18, 20-31, 33, 36, 42-44, 47-48, 50-51, 53, 55-58, 60, 62, 67, and/or 68 of SEQ ID NO: 46.

Minor modifications of a BPH virus polypeptide primary amino acid sequence may result in peptides which have substantially equivalent activity as compared to the unmodified counterpart polypeptide described herein. Such modifications may be deliberate, as by site-directed mutagenesis, or may be spontaneous. All of the polypeptides produced by these modifications are included herein. Thus, a specific, non-limiting example of a BPH virus polypeptide is a conservative variant of the BPH virus polypeptide (such as a single conservative amino acid substitution, for example, one or more conservative amino acid substitutions, for example 1-10 conservative substitutions, 2-5 conservative substitutions, 4-9 conservative substitutions, such as 1, 2, 3, 4, 5, 6, 7, 8, 9, or 10 conservative substitutions). A list of exemplary conservative substitutions is provided herein. Substitutions of the amino acids sequence shown in SEQ ID NOs: 39-58 can be made based on this table.

BPH virus polypeptides (including immunogenic fragments thereof) are disclosed herein that can be used to generate or detect an immune response to BPH virus. These peptides include or consist of at least 8 consecutive amino acids (such as at least 9, 10, 11, 12, 13, 14, 15, 16, or more consecutive amino acids) of a BPH virus polypeptide set forth above. In other examples, peptides include or consist of about 8 to 20 consecutive amino acids (such as 8 to 12 or 9 to 10 consecutive amino acids) of a BPH virus polypeptide set forth above. In several embodiments, the isolated BPH virus polypeptide is included in a fusion protein. Thus, the fusion protein can include a BPH virus polypeptide (see above) and a second heterologous moiety, such as a myc protein, an enzyme or a carrier (such as a hepatitis carrier protein or bovine serum albumin) covalently linked to the BPH virus polypeptide. In several examples, a polypeptide consisting of at least eight consecutive amino acids of one of the amino acid sequences set forth as SEQ ID NOs: 39-58 is covalently linked to a carrier. In additional examples, a polypeptide consisting of one of the amino acid sequences set forth as one of SEQ ID NOs: 39-58 is covalently linked to a carrier.

In additional examples, the polypeptide can be a fusion protein and can also include heterologous sequences to BPH virus. Thus, in several specific non-limiting examples, the immunogenic peptide is a fusion polypeptide, for example the polypeptide includes six sequential histidine residues, a β-galactosidase amino acid sequence, or an immunoglobulin amino acid sequence. The polypeptide can also be covalently linked to a carrier. In additional embodiments, the protein consists of the BPH virus polypeptide.

Further provided herein are BPH virus-like particles (VLPs) containing a gag or gag-related BPH virus polypeptide disclosed herein. In some embodiments, the gag or gag-related protein of the VLP is at least 94%, at least 95%, at least 96%, at least 97%, at least 98%, at least 99%, or 100% identical to one of SEQ ID NOs: 39-58. The BPH virus VLPs can further include any additional BPH virus proteins necessary to form the virus particle.

The polypeptide can optionally include repetitions of one or more of the BPH virus polypeptides disclosed herein (or a fragment thereof, such as at least 8 consecutive amino acids). In one specific, non-limiting example, the polypeptide includes two, three, four, five, or up to ten repetitions of one of the BPH virus polypeptides described above. Alternatively, more than one polypeptide can be included in a fusion polypeptide. Thus, in several examples, the polypeptide can include at least two, at least three, at least four, at least five or at least six of the amino acid sequences set forth as SEQ ID NOs: 39-58 or at least eight consecutive amino acids of one of the amino acid sequences set forth as SEQ ID NOs: 39-58 and repetitions of these sequences. A linker sequence can optionally be included between the BPH virus polypeptides.

The polypeptides disclosed herein can be chemically synthesized by standard methods, or can be produced recombinantly. An exemplary process for polypeptide production is described in Lu et al., *FEBS Lett.* 429:31-35, 1998. They can also be isolated by methods including preparative chromatography and immunological separations. Polypeptides can also be produced using molecular genetic techniques, such as by inserting a nucleic acid encoding the polypeptide or an epitope thereof into an expression vector, introducing the expression vector into a host cell, and isolating the polypeptide.

IV. Methods of Eliciting an Immune Response and Pharmaceutical Compositions

The BPH virus polynucleotides disclosed herein, or polypeptides encoded by the BPH virus polynucleotides (including immunogenic fragments thereof), can be used to generate an immune response in a subject. In several examples, the subject is infected with BPH virus or is at risk of being infected with BPH virus. Alternatively, the subject is a male at risk of developing BPH or worsening BPH, such as a male of at least 40 years of age. Other risk factors (such as diet) or symptoms (such as nocturia or urinary urgency) can be used to select subjects for treatment. Thus, in several embodiments, the methods include administering to such a subject a therapeutically effective amount of one or more of the BPH virus polynucleotides disclosed herein (or polypeptides encoded by these polynucleotides) in order to generate an immune response, such as, but not limited to, a protective immune response.

In exemplary applications, compositions are administered to a subject in an amount sufficient to produce an immune response to BPH virus. The disclosed BPH polynucleotides, polypeptides encoded by the polynucleotides, or immunogenic fragments thereof, are of use to inhibit an infection with BPH, avoid development of BPH in a subject who is either known or not known to be infected with BHP virus, progression to disease in a subject (for example a subject having a latent BPH virus infection), or to treat BPH in a subject infected with BPH virus. In several examples, administration of a therapeutically effective amount of a composition including one or more of the BPH polynucleotides or polypeptides encoded by the polynucleotides disclosed herein induces a sufficient immune response to decrease a symptom of BPH due to BPH virus infection, to inhibit or even prevent the development of one or more symptoms of BPH, or to inhibit or even prevent infection with BPH virus.

In some examples, the compositions are of use in inhibiting a future infection with BPH virus. Thus, a therapeutically effective amount of the composition is administered to a subject at risk of becoming infected with BPH virus. The composition inhibits the development of BPH in the subject upon subsequent exposure to BPH virus. In additional examples, the compositions are administered to a subject with a latent BPH virus infection, and inhibit or otherwise decrease the likelihood of developing symptoms of BPH.

Amounts effective for these uses will depend upon various factors, such as the general state of the patient's health and the robustness of the patient's immune system. In one example, a therapeutically effective amount of the compound is that which provides either subjective relief of at least one symptom or an objectively identifiable improvement as noted by the clinician or other qualified observer. In other examples, a therapeutically effective amount is an amount sufficient to inhibit an infection with BPH virus in a subject upon subsequent exposure of the subject to BPH virus. In additional examples, a therapeutically effective amount is an amount sufficient to inhibit development of one or more symptoms of BPH in a subject infected with BPH virus.

In some examples, one or more BPH virus polypeptides (such as a gag or gag-related protein or env protein) described herein may be covalently linked to at least one other immunogenic protein, wherein the conjugate elicits an immune response to the BPH virus polypeptide in a subject. The other immunogenic protein (sometimes referred to as a "carrier" protein) ideally has the properties of being immunogenic by itself, usable in a subject, and of a size that can be easily purified and conjugated to at least one other protein or peptide. Suitable carrier proteins are known to one of skill in the art. In particular examples, the other immunogenic protein (carrier protein) is bovine serum albumin (BSA), ovalbumin, tetanus toxoid, diphtheria toxoid, cholera toxin, *Clostridium difficile* toxin A, *C. difficile* toxin B, Shiga toxin, or *Pseudomonas aeruginosa* recombinant exoprotein A.

A BPH virus polypeptide can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) either locally or systemically, such as by intramuscular injection, subcutaneous injection, intraperitoneal injection, intravenous injection, oral administration, nasal administration, transdermal administration, or even anal administration. In one embodiment, administration is by oral administration, subcutaneous injection, or intramuscular injection. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. (see, e.g., Banga, supra). A particulate carrier based on a synthetic polymer has been shown to act as an adjuvant to enhance the immune response, in addition to providing a controlled release. Aluminum salts can also be used as adjuvants to produce an immune response.

In one specific, non-limiting example, the BPH virus polypeptide is administered in a manner to direct the immune response to a cellular response (that is, a cytotoxic T lymphocyte (CTL) response), rather than a humoral (antibody) response.

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 4-1 BBL, or combinations of these molecules, can be used as biological adjuvants (see, for example, Salgaller et al., 1998, *J. Surg. Oncol.* 68(2):122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host. In several examples, IL-2, RANTES, GM-CSF, TNF-α, IFN-γ, G-CSF, LFA-3, CD72, B7-1, B7-2, B7-1 B7-2, OX-40L, 4-1 BBL, and/or ICAM-1 are administered.

A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinly-seryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

A pharmaceutical composition including a BPH virus polypeptide, or a fusion protein, or VLP comprising a BPH virus gag polypeptide is provided. These compositions are of use to promote an immune response to BPH virus. In some embodiments, the compositions further comprise a pharmaceutically acceptable carrier and/or an adjuvant. For example, the adjuvant can be alum, Freund's complete adjuvant, a biological adjuvant or immunostimulatory oligonucleotides (such as CpG oligonucleotides).

In one embodiment, the BPH virus polypeptide is mixed with an adjuvant containing two or more of a stabilizing detergent, a micelle-forming agent, and an oil. Suitable stabilizing detergents, micelle-forming agents, and oils are detailed in U.S. Pat. No. 5,585,103; U.S. Pat. No. 5,709,860; U.S. Pat. No. 5,270,202; and U.S. Pat. No. 5,695,770, all of which are incorporated by reference. A stabilizing detergent is any detergent that allows the components of the emulsion to remain as a stable emulsion. Such detergents include Tween® 20 (polyoxyethylenesorbitan monolaurate), Tween® 40 (polyoxyethylenesorbitan monopalmitate), Tween® 60 (polyoxyethylene sorbitan monostearate), Tween® 80 (polyoxyethylenesorbitan monooleate), Zwittergent® 3-12, Teepol® HB7, and Span® 85. These detergents are usually provided in an amount of approximately 0.05% to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, *J. Am. Oil. Chem. Soc.* 54:110, 1977, and Hunter et al., *J. Immunol.* 127:1244-1250, 1981, for example, Pluronic® L62LF, L101, and L64, polyethylene glycol 1000, and Tetronic® 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5% and 10%, or in an amount between 1.25% and 5%.

The oil included in the composition is chosen to promote the retention of the antigen in oil-in-water emulsion, such as to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, squalane, eicosane, tetratetracontane, glycerol, and peanut oil or other vegetable oils. In one specific, non-limiting example, the oil is provided in an amount between 1% and 10%, or between 2.5% and 5%. The oil should be both biodegradable and biocompatible so that the body can break down the oil over time, and so that no adverse affects, such as granulomas, are evident upon use of the oil.

In one embodiment, the adjuvant is a mixture of stabilizing detergents, micelle-forming agent, and oil available under the name Provax® (IDEC Pharmaceuticals, San Diego, Calif.). An adjuvant can also be an immunostimulatory nucleic acid, such as a nucleic acid including a CpG motif, or a biological adjuvant.

In one specific, non-limiting example, a pharmaceutical composition would include about 0.1 μg to 10 mg of immunogenic BPH virus polypeptide. Dosages from 0.1 mg to about 100 mg can be used, particularly if the agent is administered to a secluded site and not into the circulatory or lymph system, such as into a body cavity or into a lumen of an organ.

Also provided is a method of immunizing a subject against BPH virus by administering to the subject VLPs containing a BPH virus polypeptide disclosed herein (such as a BPH virus gag or gag-related polypeptide), or administering a composition thereof. In some embodiments of the method, the composition further comprises a pharmaceutically acceptable carrier and/or an adjuvant. For example, the adjuvant can be alum, Freund's complete adjuvant, a biological adjuvant or immunostimulatory oligonucleotides (such as CpG oligonucleotides). In some embodiments, the VLPs (or compositions thereof) are administered intramuscularly.

In some embodiments of the methods of eliciting an immune response or immunizing a subject, the subject is administered about 1 to about 25 μg of the VLPs containing a BPH virus polypeptide. In particular examples, the subject is administered about 5 to about 20 μg of the VLPs, or about 10 to about 15 μg of the VLPs. In one specific non-limiting example, the subject is administered about 15 μg of the VLPs. However, one of skill in the art is capable of determining a therapeutically effective amount (for example an amount that inhibits or provides protection against BPH virus infection) of VLPs to administer to a subject.

In another embodiment, a pharmaceutical composition includes a nucleic acid encoding a BPH virus polypeptide or a fragment thereof. A therapeutically effective amount of the BPH virus polynucleotide can be administered to a subject in order to generate an immune response.

Optionally, one or more cytokines, such as IL-2, IL-6, IL-12, RANTES, GM-CSF, TNF-α, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 4-1 BBL, or combinations of these molecules, can be used as biological adjuvants (see, for example, Salgaller et al., 1998, *J. Surg. Oncol.* 68(2):122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically to the host. It should be noted that these molecules can be co-administered via insertion of a nucleic acid encoding the molecules into a vector, for example, a recombinant pox vector (see, for example, U.S. Pat. No. 6,045,802). In various embodiments, the nucleic acid encoding the biological adjuvant can be cloned into same vector as the BPH virus polynucleotide, or the nucleic acid can be cloned into one or more separate vectors for co-administration. In addition, nonspecific immunomodulating factors such as BCG and levamisole can be co-administered.

One approach to administration of nucleic acids is direct immunization with plasmid DNA, such as with a mammalian expression plasmid. As described above, the nucleotide sequence encoding a BPH virus polypeptide or a fragment thereof can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMs (negatively charged cage-like structures of 30-40 nm in size formed spontaneously on mixing cholesterol and saponin). Protective immunity has been generated in a variety of experimental models of infection, including toxoplasmosis and Epstein-Barr virus-induced tumors, using ISCOMs as the delivery vehicle for antigens (Mowat and Donachie, *Immunol. Today* 12:383, 1991). Doses of antigen as low as 1 µg encapsulated in ISCOMs have been found to produce Class I mediated CTL responses (Takahashi et al., *Nature* 344:873, 1990).

In another approach to using nucleic acids for immunization, a BPH virus polypeptide can be expressed by attenuated viral hosts or vectors or bacterial vectors. Recombinant vaccinia virus, adeno-associated virus (AAV), herpes virus, retrovirus, or other viral vectors can be used to express the peptide or protein, thereby eliciting a CTL response. For example, vaccinia vectors and methods useful in immunization protocols are described in U.S. Pat. No. 4,722,848. BCG provides another vector for expression of the peptides (see Stover, *Nature* 351:456-460, 1991).

When a viral vector is utilized, it is desirable to provide the recipient with a dosage of each recombinant virus in the composition in the range of from about $10^5$ to about $10^{10}$ plaque forming units, although a lower or higher dose can be administered. The composition of recombinant viral vectors can be introduced into a mammal (1) prior to any evidence of an infection with BPH virus; (2) to inhibit development of BPH in an individual infected with BPH virus; or (3) to decrease one or more symptoms of BPH in a mammal infected with BPH virus. Examples of methods for administering the composition into mammals include, but are not limited to, exposure of cells to the recombinant virus ex vivo, or injection of the composition into the affected tissue or intravenous, subcutaneous, intradermal or intramuscular administration of the virus. Alternatively the recombinant viral vector or combination of recombinant viral vectors may be administered locally in a pharmaceutically acceptable carrier. Generally, the quantity of recombinant viral vector, carrying the nucleic acid sequence of one or more BPH virus polynucleotides to be administered is based on the titer of virus particles. An exemplary range of the immunogen to be administered is $10^5$ to $10^{10}$ virus particles per mammal, such as a human.

In the embodiment where a combination of a first recombinant viral vector carrying a nucleic acid sequence of one or more BPH virus polypeptides and a second recombinant viral vector carrying the nucleic acid sequence of one or more immunostimulatory molecules is used, the mammal can be immunized with different ratios of the first and second recombinant viral vector. In one embodiment the ratio of the first vector to the second vector is about 1:1, or about 1:3, or about 1:5. Optimal ratios of the first vector to the second vector may easily be titered using the methods known in the art (see, for example, U.S. Pat. No. 6,893,869, incorporated herein by reference).

In one embodiment the recombinant viruses are constructed to express cytokines (such as TNF-α, IL-6, GM-CSF, and IL-2), and costimulatory and accessory molecules (B7-1, B7-2) alone and in a variety of combinations. Simultaneous production of an immunostimulatory molecule and the BPH virus polypeptide enhances the generation of specific effectors. Without being bound by theory, dependent upon the specific immunostimulatory molecules, different mechanisms might be responsible for enhanced immunogenicity: augmentation of help signal (IL-2), recruitment of professional APC (GM-CSF), increase in CTL frequency (IL-2), effect on antigen processing pathway and MHC expression (IFNγ and TNFα) and the like. For example, IL-2, IL-6, interferon, tumor necrosis factor, or a nucleic acid encoding these molecules, can be administered in conjunction with a BPH virus polypeptide, or a nucleic acid encoding a BPH virus polypeptide. The co-expression of a BPH virus polypeptide together with at least one immunostimulatory molecule can be effective in an animal model to show therapeutic effects.

In one embodiment, a nucleic acid encoding a BPH polypeptide is introduced directly into cells. For example, the nucleic acid can be loaded onto gold microspheres by standard methods and introduced into the skin by a device such as the Helios™ Gene Gun (Bio-Rad, Hercules, Calif.). The nucleic acids can be "naked," consisting of plasmids under control of a strong promoter. Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, for example, U.S. Pat. No. 5,589,466).

Actual methods for preparing administrable compositions will be known or apparent to those skilled in the art and are described in more detail in such publications as *Remington: The Science and Practice of Pharmacy*, The University of the Sciences in Philadelphia, Editor, Lippincott, Williams, & Wilkins, Philadelphia, Pa., 21$^{st}$ Edition (2005).

Single or multiple administrations of the compositions are administered, depending on the dosage and frequency as required and tolerated by the subject. In one embodiment, the dosage is administered once as a bolus, but in another embodiment can be applied periodically until a therapeutic result is achieved. In one embodiment, the dose is sufficient to treat or ameliorate symptoms or signs of BPH without producing unacceptable toxicity to the subject. In another embodiment, the dose is sufficient to inhibit infection with BPH virus upon subsequent exposure to BPH virus. In a further embodiment, the dose is sufficient to inhibit one or more symptoms of BPH in a subject with a latent BPH virus infection. Systemic or local administration can be utilized.

V. Methods of Detecting BPH Virus Infection

Methods for detection of BPH virus infection in a subject are disclosed herein. In some examples, detection of BPH virus infection indicates that the subject has or is at risk of developing benign prostatic hyperplasia. The methods include the use of polynucleotide sequences disclosed above. BPH virus infection can be detected by detecting the presence, absence, or level of BPH virus polynucleotide in a biological sample. In several examples, PCR-based assays are utilized. In other examples, BPH virus infection can be detected by detecting the presence, absence, or level of BPH virus antibody in a sample, utilizing the BPH virus polypeptides disclosed herein. The methods disclosed herein include methods of specifically detecting BPH virus (such as a BPH virus polynucleotide or polypeptide) in a sample from a subject, for example discriminating the presence of BPH virus in a sample as opposed to XMRV. In some examples, the disclosed methods include detecting the presence of a BPH virus and the absence of XMRV in a sample from a subject.

In some embodiments, a biological sample is obtained from a subject of interest (such as a subject with BPH or suspected of having BPH). Suitable biological samples include, but are not limited to, blood; derivatives and fractions of blood (such as serum, plasma, or peripheral mononuclear cells); biopsied or surgically removed tissue, including tissues that are, for example, unfixed, frozen, fixed in formalin and/or embedded in paraffin; urine; saliva; cerebrospinal fluid; prostate fluid; pus; or bone marrow aspirates. In some examples, a sample includes prostate cells or tissue (such as tissue or cells obtained from a prostate biopsy or prostate tissue obtained by prostatectomy or TURP). In other examples, the sample includes urine.

A. Detecting BPH Virus Nucleic Acids

Methods for extracting nucleic acids such as RNA and/or DNA from a sample, such as a prostate tissue sample, are known to one of skill in the art. Nucleic acids can be extracted using standard methods. For instance, rapid nucleic acid preparation can be performed using a commercially available kit (such as kits and/or instruments from Qiagen (such as DNEasy® or RNEasy® kits), Roche Applied Science (such as MagNA Pure kits and instruments), Thermo Scientific (KingFisher mL), bioMérieux (Nuclisens® NASBA Diagnostics), or Epicentre (Masterpure™ kits)). In other examples, the nucleic acids may be extracted using guanidinium isothiocyanate, such as single-step isolation by acid guanidinium isothiocyanate-phenol-chloroform extraction (Chomczynski et al. *Anal. Biochem.* 162:156-159, 1987). The sample can be used directly or can be processed, such as by adding solvents, preservatives, buffers, or other compounds or substances.

In some embodiments, the method includes a probe that specifically hybridizes to a BPH virus polynucleotide, such as the BPH virus polynucleotides disclosed herein. In some examples, the probe is capable of specifically hybridizing (for example, under stringent conditions or very stringent conditions) to a BPH virus nucleic acid, but does not hybridize to an XMRV nucleic acid under the same conditions.

In some examples, the probe is detectably labeled, either with an isotopic or non-isotopic label; in alternative embodiments, the target nucleic acid is labeled. Non-isotopic labels can, for instance, comprise a fluorescent or luminescent molecule, or an enzyme, co-factor, enzyme substrate, or hapten. The probe is incubated with a single-stranded or double-stranded preparation of RNA, DNA, or a mixture of both, and hybridization is determined. In some examples, the hybridization results in a detectable change in signal such as in increase or decrease in signal, for example from the labeled probe. Thus, detecting hybridization comprises detecting a change in signal from the labeled probe during or after hybridization relative to signal from the label before hybridization.

Detecting presence of at least one BPH virus nucleic acid in a sample involves contacting the sample with at least one probe (such as at least one probe disclosed herein) that is capable of hybridizing to a BPH virus nucleic acid, under conditions of very high stringency. In particular examples, the probe is detectably labeled. In some examples, the probe is at least 10, 15, 20, 25, 30, 35, or 40 nucleotides in length. In other examples, the probe may be no more than 10, 15, 20, 25, 30, 35, or 40 nucleotides in length.

In one example, the method includes contacting the sample with a probe comprising a nucleic acid molecule between 10 and 40 nucleotides in length, wherein the probe is capable of specifically hybridizing under very high stringency conditions to a BPH virus nucleic acid (such as a BPH virus gag, gag-related (e.g., glyco-gag), env, pol, variable region, or ARE nucleic acid), wherein the probe does not hybridize under very high stringency conditions to an XMRV nucleic acid, and detecting hybridization between the BPH virus nucleic acid and the probe. In some examples, the BPH virus nucleic acid includes a nucleic acid sequence having at least 75% sequence identity (such as at least 80%, 85%, 90%, 95%, or more identity) with a nucleic acid sequence set forth as any one of SEQ ID NOs: 1-38. In additional examples, the probe can differentiate between BV1 and BV2 virus types. In particular examples, the probe includes a nucleic acid that is least 90% identical (such as 91%, 92%, 93%, 94%, 95%, 96%, 97%, 98%, 99%, or 100% identical) to the nucleotide sequence that comprises, consists essentially of, or consists of the nucleic acid sequence set forth as SEQ ID NO: 73 or SEQ ID NO: 74.

In some examples, the method further includes amplifying nucleic acids (such as BPH virus nucleic acids) in a sample prior to probe hybridization for detection. Any nucleic acid amplification method can be used to detect the presence of one or more BPH virus nucleic acids in a sample. In one specific, non-limiting example, polymerase chain reaction (PCR) is used to amplify the viral-specific nucleic acids. In other specific, non-limiting examples, real-time PCR, reverse transcriptase-polymerase chain reaction (RT-PCR), real-time reverse transcriptase-polymerase chain reaction (rt RT-PCR), ligase chain reaction, or transcription-mediated amplification (TMA) is used to amplify the nucleic acids. In a specific example, one or more (such as 1, 2, 3, or 4) BPH virus nucleic acids are amplified by real-time PCR (for example, multiplex real-time PCR), for example real-time TaqMan® PCR. Techniques for nucleic acid amplification are well-known to those of skill in the art.

Typically, at least two primers are utilized in the amplification reaction. Amplification of BPH virus nucleic acid involves contacting the sample with one or more primers (such as two or more primers) that are capable of hybridizing to and directing the amplification of a BPH virus nucleic acid, wherein the one or more primers do not hybridize to and/or do not direct amplification of an XMRV nucleic acid (for example under very high stringency conditions). In some examples, the primer is capable of hybridizing under very high stringency conditions to at least one nucleic acid sequence having at least 75% sequence identity (such as at least 80%, 85%, 90%, 95%, or more identity) with a nucleic acid sequence set forth as SEQ ID NOs: 1-38 and directing amplification of a BPH virus nucleic acid. In other examples, amplification of BPH virus nucleic acid involves contacting the sample with one or more primers (such as two or more primers) that are capable of hybridizing to and directing the amplification of a BPH virus nucleic acid and hybridizing to and/or directing amplification of a nucleic acid from another virus (such as XMRV). In such examples, a BPH virus nucleic acid can be specifically detected utilizing a probe that hybridizes to a BPH virus nucleic acid, but does not hybridize to an XMRV nucleic acid (for example under very high stringency conditions). In some examples, the primer comprises, consists essentially of, or consists of a nucleic acid that is least 90% identical (such as 91%, 92%, 93%, 94%, 95%, 96%, 97%, 98%, 99%, or 100% identical) to the nucleotide sequence set forth as SEQ ID NOs: 59-68, 71, or 72.

The PCR step can use a variety of thermostable DNA-dependent DNA polymerases, for example, the Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN® RT-PCR can be performed using commercially available equipment, such as, for example, ABI PRISM 7700® Sequence Detection System™ (Perkin-Elmer-Applied Biosystems, Foster City, Calif., USA), or LightCycler® (Roche Applied Science, Mannheim, Germany). In one embodiment, the 5' nuclease procedure is run on a real-time quantitative PCR device such as the ABI PRISM 7700® Sequence Detection System®. The system includes a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

In some examples, real-time PCR assay data are initially expressed as $C_t$, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors and the effect of sample-to-sample variation, RT-PCR can be performed using an internal standard. The ideal internal standard is expressed at a constant level among different tissues, and is unaffected by the experimental treatment. In some examples, RNAs used to normalize patterns of gene expression are mRNAs for the housekeeping genes glyceraldehyde-3-phosphate-dehydrogenase (GAPDH), beta-actin, and 18S ribosomal RNA. In other examples, DNA used as a positive control includes ribonuclease P (RNase P).

A more recent variation of the RT-PCR technique is the real time quantitative PCR, which measures PCR product accumulation through a dual-labeled fluorogenic probe (e.g., a TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Heid et al., Genome Res. 6:986-994, 1996). Quantitative PCR is also described in U.S. Pat. No. 5,538, 848, the disclosure of which is incorporated herein by reference. Related probes and quantitative amplification procedures are described in U.S. Pat. Nos. 5,716,784 and 5,723, 591, the disclosures of which are incorporated herein by reference. Instruments for carrying out quantitative PCR in microtiter plates are available from PE Applied Biosystems (Foster City, Calif. 94404) under the trademark ABI Prism® 7700.

The steps of a representative protocol for quantitating gene expression using fixed, paraffin-embedded tissues as the RNA source, including mRNA isolation, purification, primer extension and amplification are given in various published journal articles (see Godfrey et al., J. Mol. Diagn. 2: 84 91, 2000; Specht et al., Am. J. Pathol. 158: 419 29, 2001). Briefly, a representative process starts with cutting about 10 µm thick sections of paraffin-embedded tissue sample. The RNA is then extracted, and protein and DNA are removed. After analysis of the RNA concentration, RNA repair and/or amplification steps can be included, if necessary, and RNA is reverse transcribed using gene specific promoters followed by RT-PCR.

An alternative quantitative nucleic acid amplification procedure is described in U.S. Pat. No. 5,219,727, which is incorporated herein by reference. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

In further embodiments, the methods disclosed herein include detecting methylation level of at least one BPH virus nucleic acid, such as a regulatory sequence nucleic acid (such as an ARE sequence nucleic acid, for example a nucleic acid sequence of SEQ ID NOs: 34-38). Without being bound by theory, in some examples, altered methylation (such as increased or decreased methylation as compared to a control) of at least one BPH virus nucleic acid indicates that the virus may be transcriptionally active. Presence of transcriptionally active virus can be used to select a subject for treatment for BPH virus infection (such as by administering an anti-viral agent) or for administration of an agent that decreases DNA methylation (such as 5-aza-2'-deoxycytidine, decitabine, or zebularine). In some examples, methylation level of BPH virus DNA is compared to a control, such as a normal prostate tissue sample (such as a prostate tissue sample from a subject without BPH or without prostate cancer). In other examples, a control includes a recombinant positive methylation control (for example, a clone of the region of interest that has been methylated in vitro with an enzyme such as SssI methylase or recombinant DNA methyltransferase I). In a particular example, methylation of BPH virus DNA is decreased by at least about 10% (such as at least about 20%, 30%, 40%, 50%, 60%, 70%, 80%, 90%, or more) as compared with a normal prostate tissue. In another example, methylation of BPH virus DNA is increased by at least about 10% (such as at least about 20%, 30%, 40%, 50%, 60%, 70%, 80%, 90%, or more) as compared with a control.

Methods of detecting DNA methylation are well known to one of skill in the art. Such methods include methylation-specific enzyme digestion (Singer-Sam, et al., Nucleic Acids Res. 18(3): 687 (1990), Taylor, et al., Leukemia 15(4): 583-9 (2001)), bisulfite DNA sequencing (Frommer, et al., Proc. Natl. Acad. Sci. USA 89(5): 1827-31 (1992), Feil, et al., Nucleic Acids Res. 22(4): 695-6 (1994)), methylation-specific PCR (MSP) (Herman, et al., Proc. Natl. Acad. Sci. USA 93(18): 9821-6 (1996)), methylation-sensitive single nucleotide primer extension (MS-SnuPE) (Gonzalgo, et al., Nucleic Acids Res. 25(12): 2529-31 (1997)), restriction landmark genomic scanning (RLGS) (Kawai, Mol. Cell Biol.

14(11): 7421-7 (1994), Akama, et al., *Cancer Res.* 57(15): 3294-9 (1997)), and differential methylation hybridization (DMH) (Huang, et al., *Hum. Mol. Genet.* 8(3): 459-70 (1999)). See also U.S. Pat. Nos. 7,229,759; 7,144,701; 7,125,857; 7,118,868; 6,960,436; 6,905,669; 6,605,432; 6,265,171; 5,856,094; 5,786,146; 6,017,704; 6,200,756.

B. Detecting BPH Virus Polypeptides

As an alternative or in addition to detecting BPH virus nucleic acids, BPH virus polypeptides can be detected using routine methods such as Western blot, immunohistochemistry, or mass spectrometry. In some embodiments, the method includes an antibody that specifically binds to a BPH virus polypeptide, such as the BPH virus polypeptides disclosed herein. In some examples, the antibody is capable of specifically binding to a BPH virus polypeptide, but does not bind to an XMRV polypeptide under the same conditions.

In some examples, proteins are purified before detection. In one example, BPH virus polypeptides (such as a polypeptide having at least 75% sequence identity with an amino acid set forth as SEQ ID NOs: 39-58, or a fragment thereof) can be detected by incubating a biological sample with an antibody that specifically binds to one or more of the disclosed BPH virus polypeptides. The antibody can include a detectable label. For example, the antibody (primary antibody) can be directly labeled, or the sample can be subsequently incubated with a secondary antibody that is labeled (for example with a fluorescent label). The label can then be detected, for example by microscopy, ELISA, flow cytometry, or spectrophotometry. In another example, the biological sample is analyzed by Western blotting for detecting expression of a BPH virus polypeptide.

In one example, an antibody that specifically binds a BPH virus polypeptide is directly labeled with a detectable label. In another example, an antibody that specifically binds a BPH virus polypeptide (the first antibody) is unlabeled and a second antibody or other molecule that can bind the first antibody that specifically binds the BPH virus polypeptide is labeled. As is well known to one of skill in the art, a second antibody is chosen that is able to specifically bind the specific species and class of the first antibody. For example, if the first antibody is a human IgG, then the secondary antibody can be an anti-human-IgG. Other molecules that can bind to antibodies include, without limitation, Protein A and Protein G, both of which are available commercially.

Suitable labels for the antibody or secondary antibody include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary magnetic agent is gadolinium, and non-limiting exemplary radioactive labels include $^{125}$I, $^{131}$I, $^{35}$S or $^{3}$H.

In an alternative example, one or more BPH virus polypeptides can be assayed in a biological sample by a competition immunoassay utilizing BPH virus polypeptide standards labeled with a detectable substance and an unlabeled antibody that specifically binds the BPH virus polypeptide. In this assay, the biological sample (such as serum, tissue biopsy, or cells isolated from a tissue biopsy), the labeled BPH virus polypeptide standards and the antibody that specifically binds the BPH virus polypeptide are combined and the amount of labeled BPH virus polypeptide standard bound to the unlabeled antibody is determined. The amount of BPH virus polypeptide in the biological sample is inversely proportional to the amount of labeled BPH virus polypeptide standard bound to the antibody that specifically binds the BPH virus polypeptide.

C. Detecting BPH Virus Antibodies

In other examples, methods disclosed herein include detecting presence of antibodies to one or more BPH virus polypeptides (such as a polypeptide of SEQ ID NOS: 39-58) in a sample from a subject. In some embodiments, the method includes detecting an antibody that specifically binds to a BPH virus polypeptide, such as the BPH virus polypeptides disclosed herein. In some examples, the antibody is capable of specifically binding to a BPH virus polypeptide, but does not bind to an XMRV polypeptide under the same conditions.

In some examples, immunoassays such as enzyme-linked immunosorbent assay (ELISA), indirect fluorescence immunoassay (IFA), and immunoblotting are utilized to accomplish the detection of antibodies according to the methods of this disclosure. An ELISA method effective for the detection of the antibodies can, for example, be as follows: 1) bind a polypeptide (such as a polypeptide having at least 75% sequence identity with an amino acid sequence set forth as SEQ ID NOs: 39-58, or a fragment thereof) to a substrate; 2) contact the bound polypeptide with a fluid or tissue sample containing the antibody; 3) contact the above with a secondary antibody bound to a detectable moiety which is reactive with the bound antibody (for example, horseradish peroxidase enzyme or alkaline phosphatase enzyme); 4) contact the above with the substrate for the enzyme; 5) contact the above with a color reagent; and 6) observe/measure color change or development.

As a further example, a micro-agglutination test can be used to detect the presence of antibodies to the disclosed BPH virus polypeptides in a sample. Briefly, latex beads, red blood cells or other agglutinable particles are coated with a BPH virus polypeptide (such as a polypeptide having at least 75% sequence identity with an amino acid sequence set forth as SEQ ID NOs: 39-58, or a fragment thereof) and mixed with a sample, such that antibodies in the sample which are specifically reactive with the antigen crosslink with the antigen, causing agglutination. The agglutinated polypeptide-antibody complexes form a precipitate, visible with the naked eye or measurable by spectrophotometer.

In yet another example, a microsphere-based immunoassay can be used to detect the presence of antibodies in a sample. Briefly, microsphere beads are coated with a component of the disclosed BPH virus polypeptides (such as a polypeptide having at least 75% sequence identity with an amino acid sequence set forth as SEQ ID NOs: 39-58 or a fragment thereof) and mixed with a sample, such that antibodies in the sample which are specifically reactive with the antigen bind the antigen. The bead-bound polypeptide-antibody complexes are allowed to react with fluorescent-dye labeled anti-species antibody (such as FITC-labeled goat anti-human IgM), and are measured using a microsphere reader (such as a Luminex instrument).

EXAMPLES

Example 1

BPH Virus Primers

Primers for virus amplification were designed based on homology between XMRV and related viruses (e.g., murine leukemia virus), making the assumption that these similarities would be the most conserved regions of this family of retroviruses. The primers are shown in Table 1.

TABLE 1

PCR Primers

| Region | Primer Name | Sequence | SEQ ID NO: |
|---|---|---|---|
| Gag | 92F | CCTTGGGAGGGTCTCCTCAG | 59 |
|  | delR | CAGACGCGCGGCGCGGTTTCG | 60 |
| Envelope #1 | XMRV5741F | CGGCCGGAACAGCATGGAAA | 61 |
|  | XMRV6903R | CCGGCGGGAGAGGCCAAATA | 62 |
| Envelope #2 | XMRV6650F | CCTCAACCTCACCAGTCCCGACA | 63 |
|  | XMRV7765R | CCATGCCTTGCAAAATGGCGTTA | 64 |

TABLE 1-continued

PCR Primers

| Region | Primer Name | Sequence | SEQ ID NO: |
|---|---|---|---|
| Variable | XMRV5943F | GGGACGATGACAGACACTTTCC | 65 |
|  | XMRV6320R | TTACCCGCGTCAGTGAATTCTAGG | 66 |
| Androgen response element | XMRV7768F | CGCCATTTTGCAAGGCATGGA | 67 |
|  | XMRV8052R | GGGAGCAAAAAGCGCGGGTA | 68 |
| Genomic control | STR D7S820F | CAGGCATGTGCTACTGCATCC | 69 |
|  | STR D7S820R | TCCTCATTGACAGAATTGCACCA | 70 |

Example 2

Amplification of BPH Virus from BPH Patient Samples

Genomic DNA was isolated from 10-30 mg pieces of frozen tissue obtained from patients undergoing Trans Urethral Resection of the Prostate (TURP) for symptomatic BPH or from normal prostate tissue obtained from organ donors using the DNEasy® blood and tissue kit (Qiagen, Valencia, Calif.). PCR reactions were carried out in an Eppendorf Mastercycler® personal thermocycler (Eppendorf, Hauppauge, N.Y.) using the conditions described in Table 2. Approximately 50-100 ng of DNA was used in each PCR reaction. PCR products were subcloned and sequenced.

TABLE 2

PCR Reaction Conditions

| Region | Reagents | Conditions | |
|---|---|---|---|
| Gag | Titanium buffer (Clontech) | Denature: | 95° C. 1 min |
|  | 0.5 µM each primer | 40 cycles: | 95° C. 30 sec |
|  | 0.2 mM each dNTP |  | 68° C. 30 sec |
|  | 0.2 µl 50x Titanium Taq (Clontech) | Final extension: | 68° C. 3 min |
| Envelope #1 | Expand Long Template #1 buffer (Roche) | Denature: | 94° C. 2 min |
|  | 0.5 µM each primer | 40 cycles: | 94° C. 30 sec |
|  | 0.2 mM each dNTP |  | 62° C. 30 sec |
|  | 0.35 µl Expand Long Template Taq (Roche) |  | 68° C. 45 sec |
|  |  | Final extension: | 68° C. 7 min |
| Envelope #2 | Expand Long Template #1 buffer (Roche) | Denature: | 94° C. 2 min |
|  | 0.5 µM each primer | 40 cycles: | 94° C. 30 sec |
|  | 0.2 mM each dNTP |  | 60° C. 30 sec |
|  | 0.35 µl Expand Long Template Taq (Roche) |  | 68° C. 45 sec |
|  |  | Final extension: | 68° C. 7 min |
| Variable | Expand Long Template #1 buffer (Roche) | Denature: | 94° C. 2 min |
|  | 0.5 µM each primer | 40 cycles: | 94° C. 30 sec |
|  | 0.2 mM each dNTP |  | 63° C. 30 sec |
|  | 0.35 µl Expand Long Template Taq (Roche) |  | 68° C. 45 sec |
|  |  | Final extension: | 68° C. 7 min |
| Androgen response element | Titanium buffer (Clontech) | Denature: | 94° C. 2 min |
|  | 0.5 µM each primer | 40 cycles: | 94° C. 30 sec |
|  | 0.2 mM each dNTP |  | 61° C. 30 sec |
|  | 0.2 µl 50x Titanium Taq (Clontech) |  | 68° C. 45 sec |
|  |  | Final extension: | 68° C. 7 min |

All reactions were 25 µl total volume.

Fifteen of twenty BPH samples produced an amplified product with the gag primers shown in Table 1, while only three of twenty donor samples were amplified by these primers (FIG. 1). An immortalized, presumably non-diseased prostate stromal cell line (WPMY-1), also produced an amplified product with the gag primers, however the LNCaP prostate cancer cell line and the immortalized prostate epithelial cell line RWPE-1 did not produce an amplified product (FIG. 1). A genomic PCR was performed on all samples to determine the integrity of the DNA. For the ARE region, 4 BPH samples were tested and all were positive, as were the PC3 and WPMY cell lines; however, the LNCaP cell line was negative. For the variable envelope region HB068 and WPMY and PC3 were positive, while LNCaP was negative.

Figure 2:
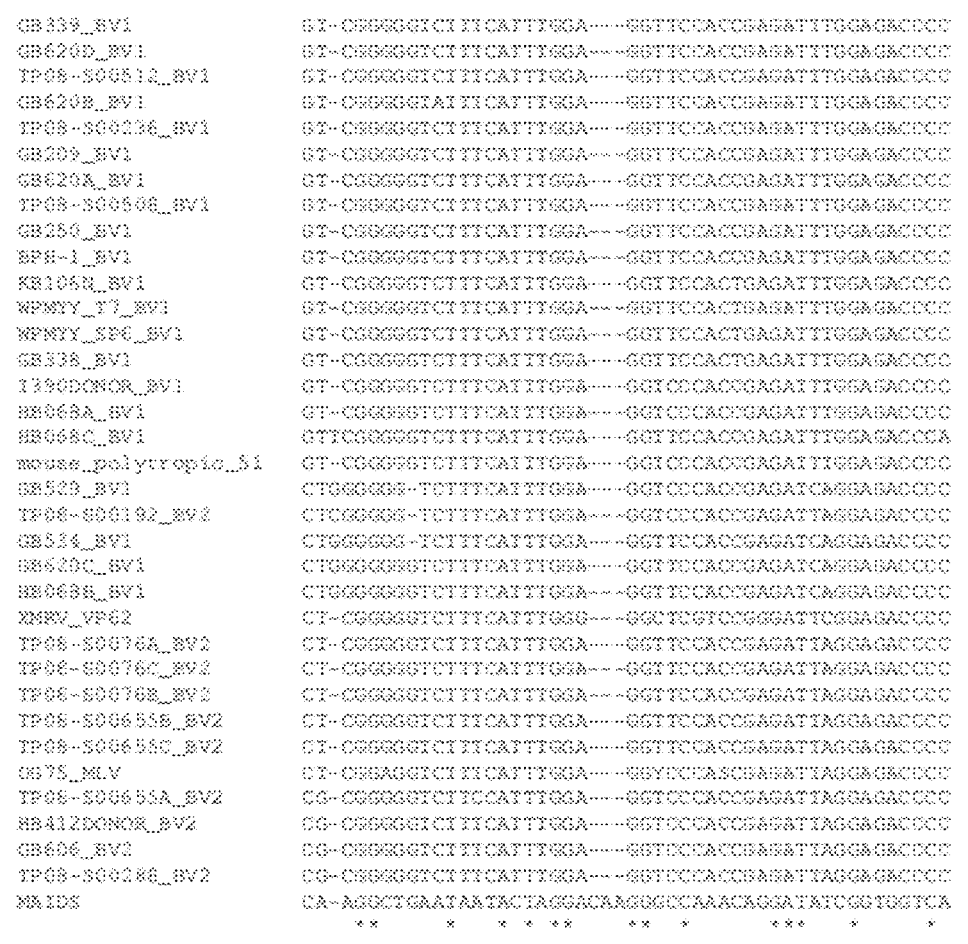
Figure 2:
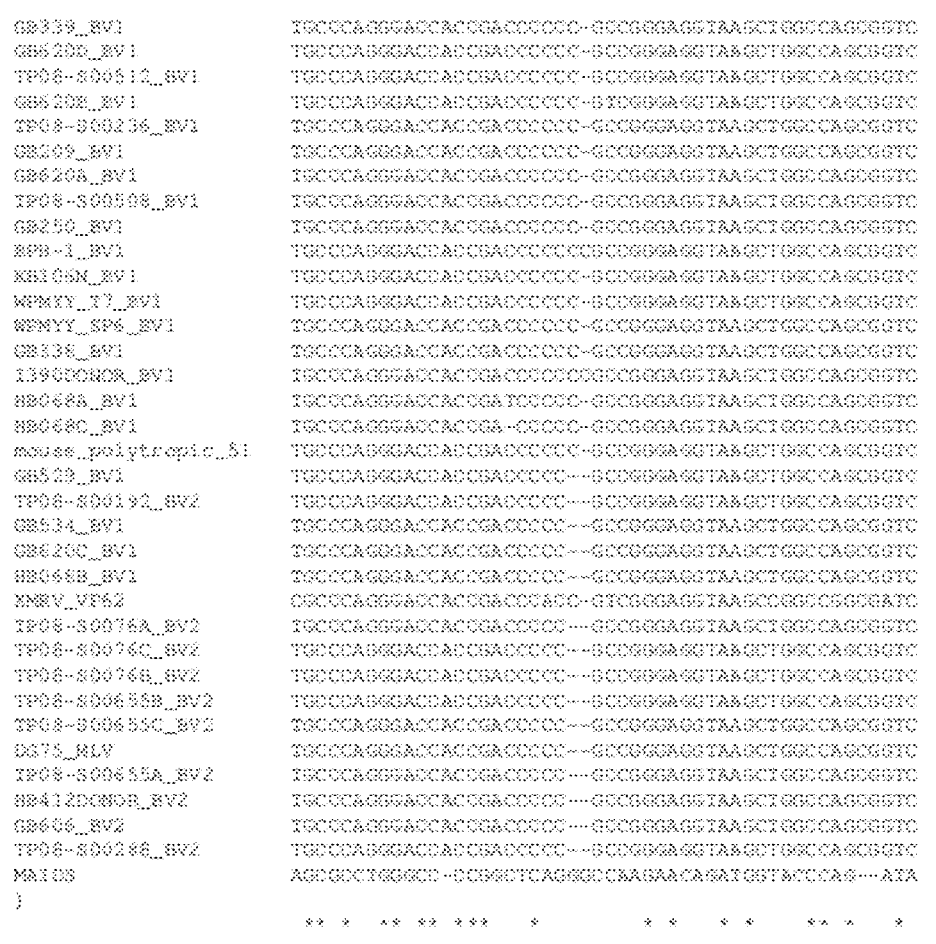
Figure 2:
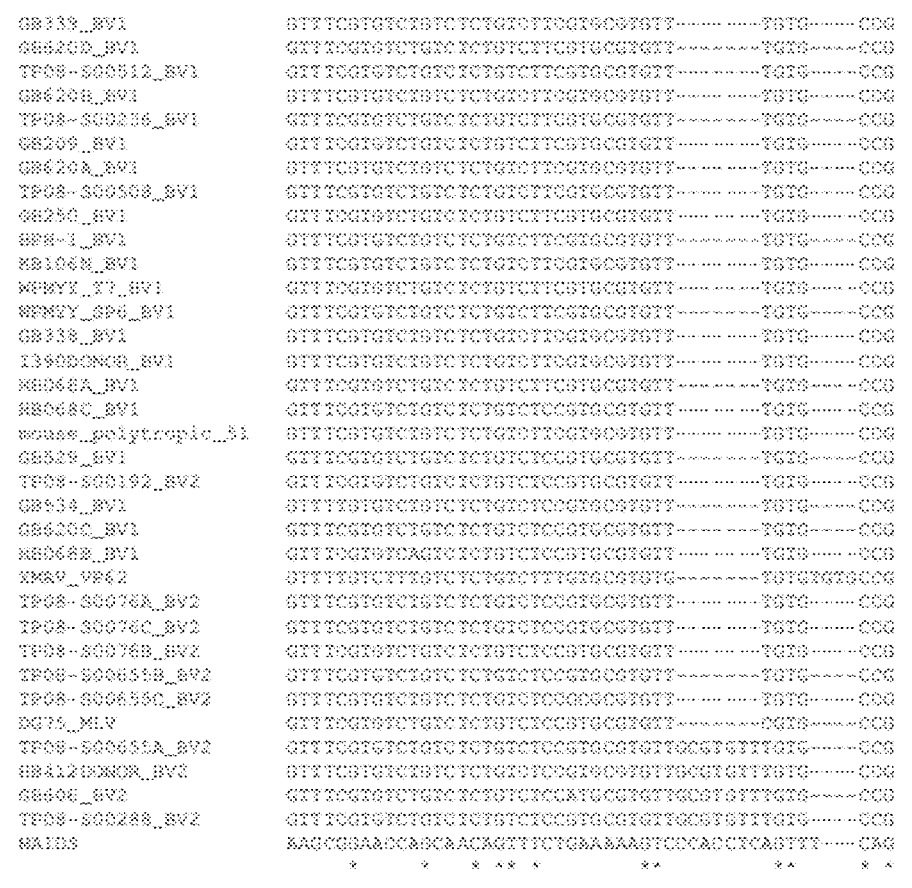
Figure 2:
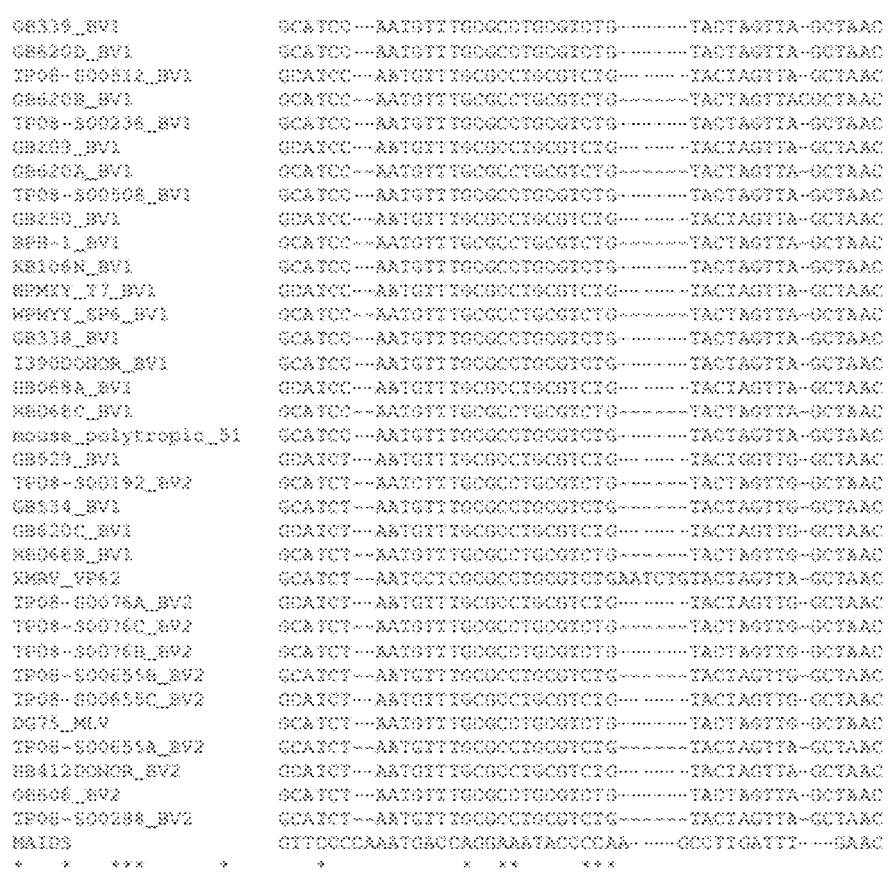
Figure 2:
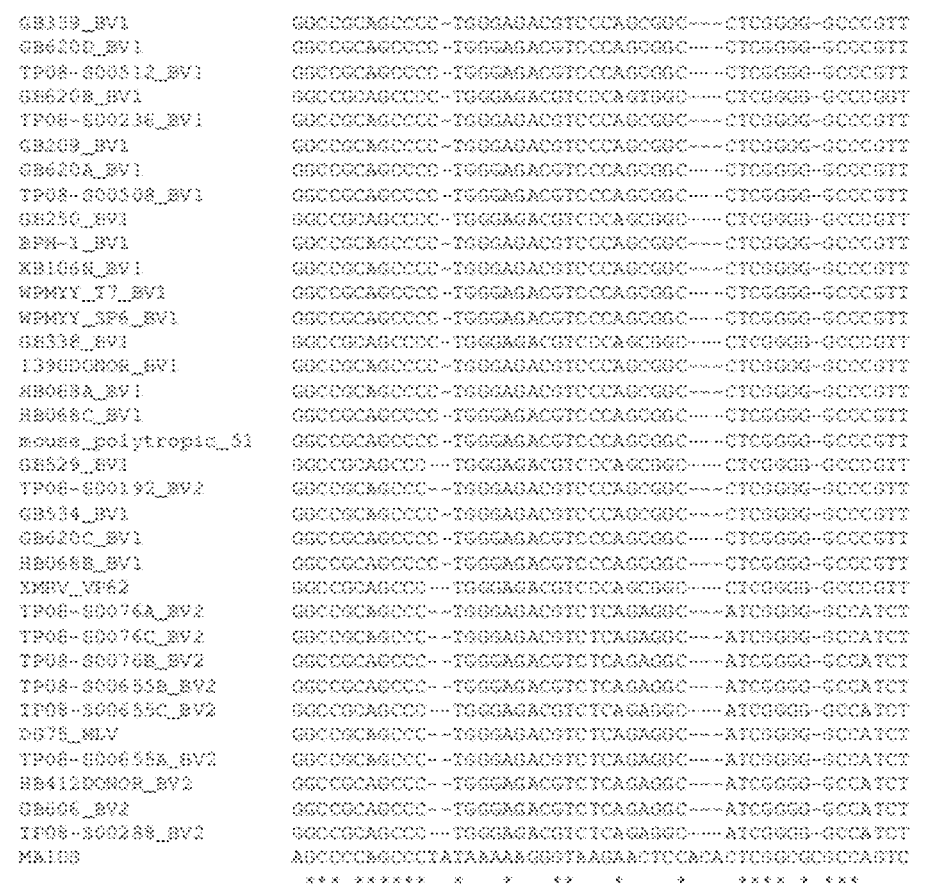
Figure 2:
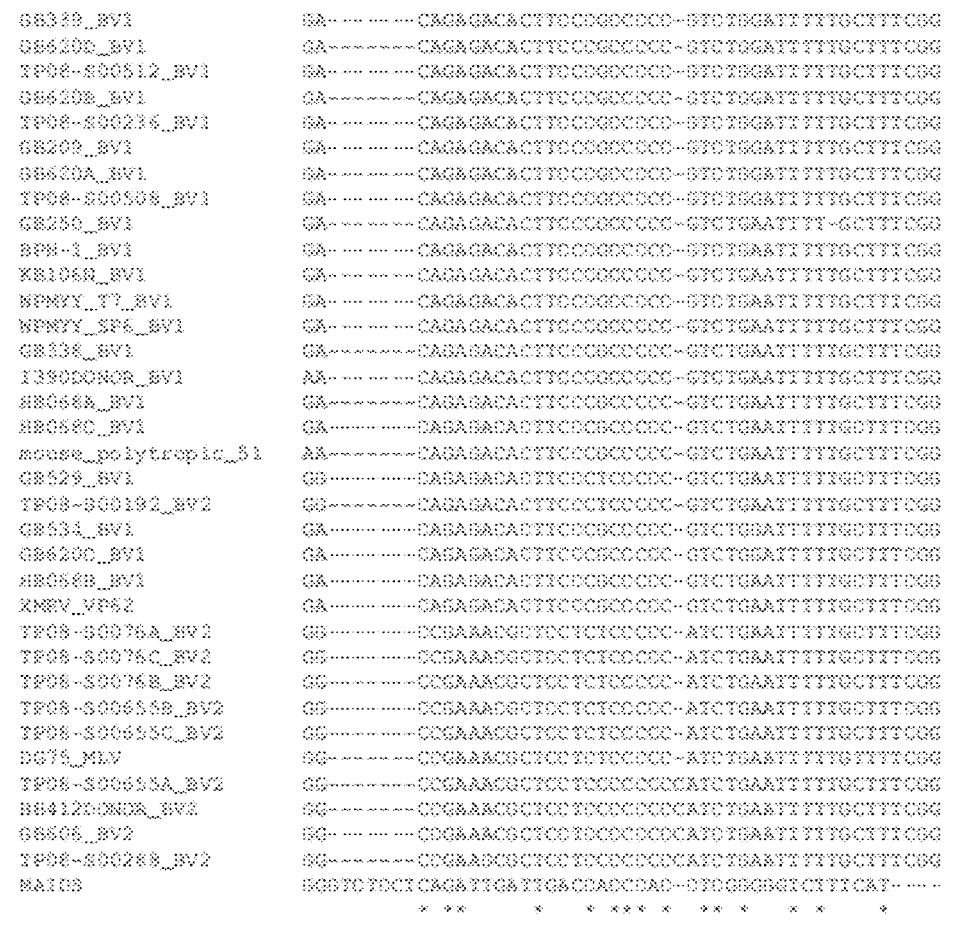
Figure 2:
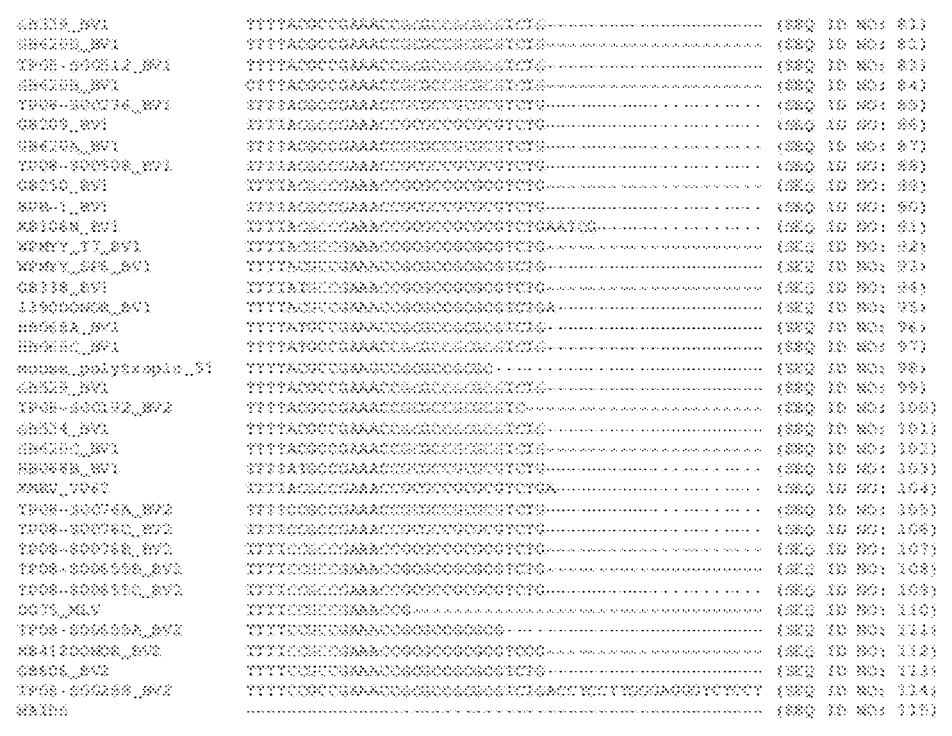
Figure 3:
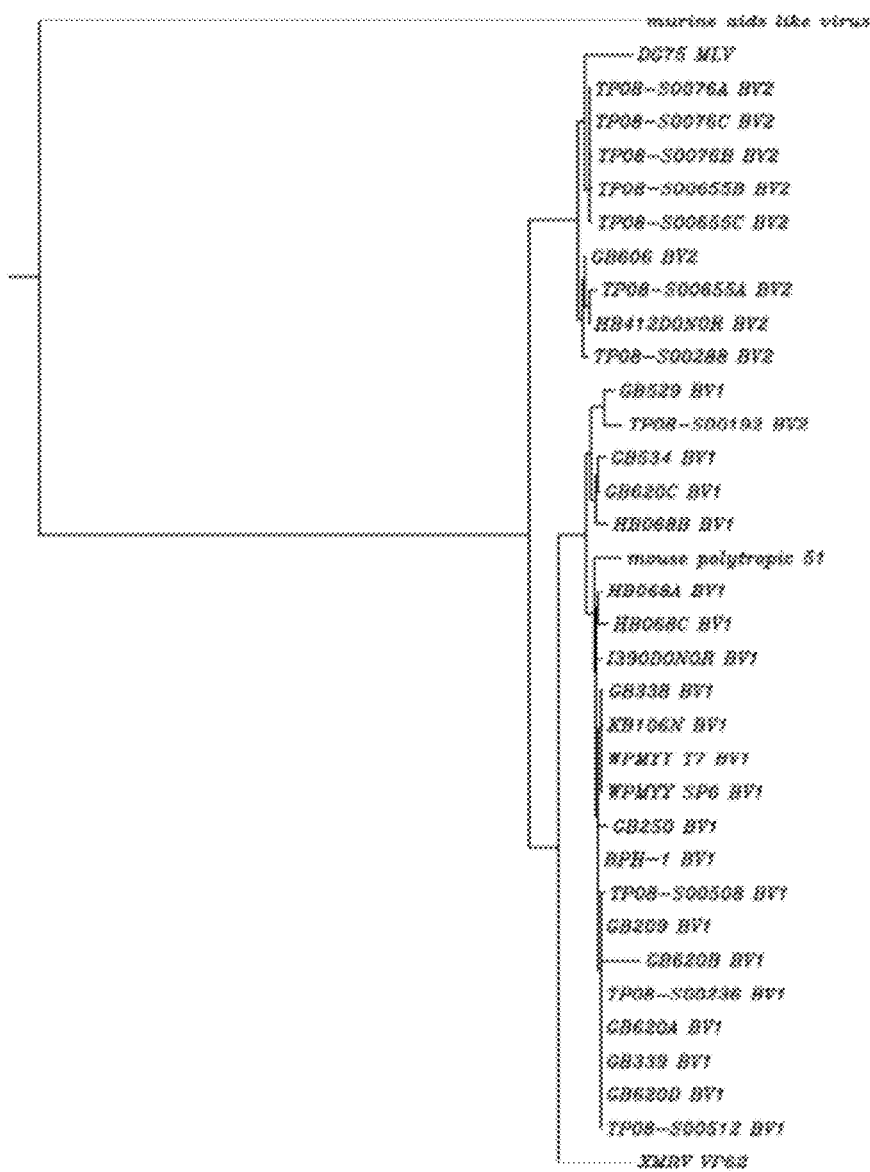
FIG. 3 is a dendrogram of the sequence alignment shown in FIG. 2.

The gag sequences obtained from the BPH and donor samples were not identical to any sequences from viruses know to infect humans. An alignment of the glyco-gag sequences is shown in FIG. 2 and a dendrogram showing the relation of these sequences to XMRV is shown in FIG. 3.

Based on the gag sequences, two genetically different BPH viruses have been identified; these have been designated BV1 and BV2. The BV1 sequences include an open reading frame that utilizes an alternative start codon, which produces a glyco-gag protein. This protein is predicted to be inserted in the cell membrane and does not become a structural part of the virus. The cell surface location of this protein makes it a target for vaccine design.

The sequence identity between the amplified gag, envelope, and variable region sequences and XMRV is shown in Table 3. Sequences obtained from the gag region from 17 BPH samples, 2 normal prostate tissues from organ donors, and the BPH and WPMY cell lines were compared. Slight variations were identified between the sequences even within the same patient's tissue, suggesting that the virus may be actively replicating and acquiring mutations.

TABLE 3

Sequence Identity to XMRV in an exemplary BPH patient sample

| Region | % Identity to XMRV |
|---|---|
| Gag | 89 |
| Envelope | 95 |
| Variable region | 93 |

Figure 4B:
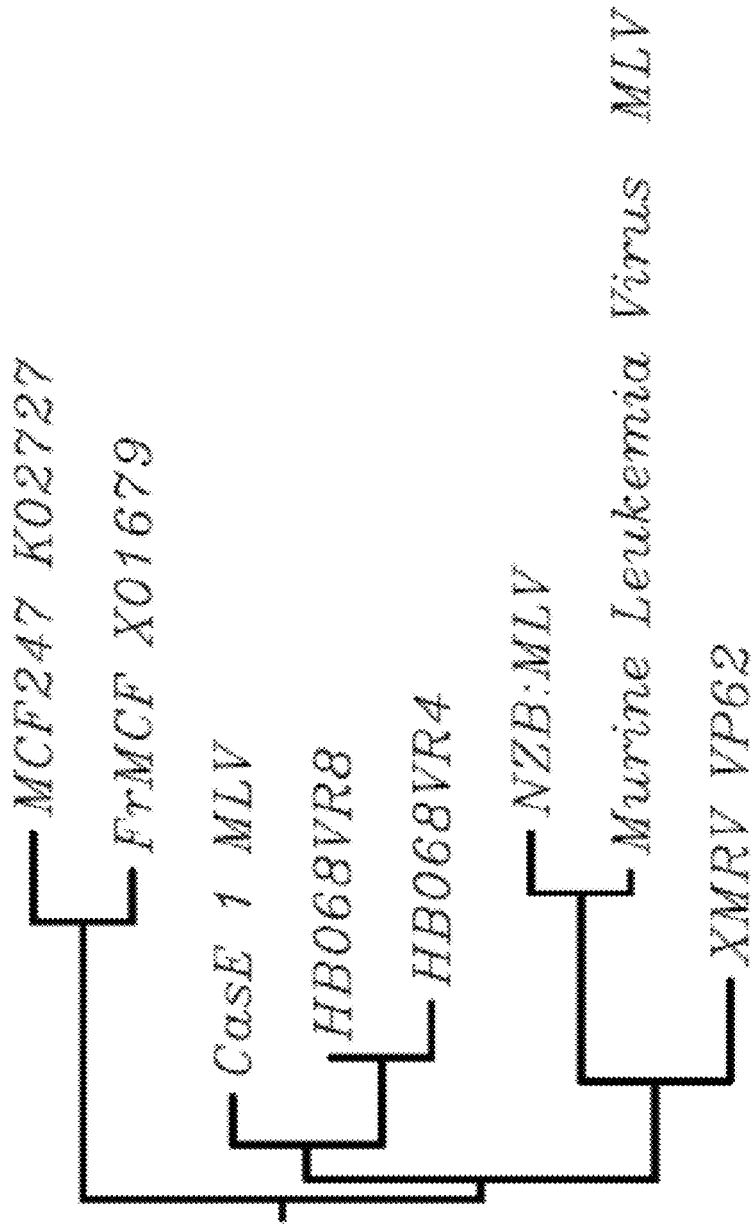
FIG. 4B is a dendrogram of the sequence alignment shown in FIG. 4A.

Comparison of the variable region (VR) sequences amplified from a BPH patient (two clones from the same individual), Casitas wild mouse (Genbank accession number EF606901.1), and XMRV identified several amino acids that differ between BPH virus and XMRV. An alignment is shown in FIG. 4A and a dendrogram is shown in FIG. 4B.

Androgen response element (ARE) sequences amplified from three BPH patients were compared to the ARE consensus sequence (Nelson et al., *Proc. Natl. Acad. Sci. USA* 99:11890-11895, 2002). The alignment is shown in FIG. 5. The ARE sequence found in BPH tissue may be involved in androgen driven transcription of the BPH virus identified here.

Example 3

Real-Time PCR Detection of BPH Virus

This example describes real-time PCR detection of BPH virus is samples from subjects with BPH.

PCR primers and probes were designed to detect and differentiate BV1 and BV2 sequences described in Example 2. The primers amplify both BV1 and BV2; unique probes for each virus were designed. Primer and probe sequences are shown in Table 4.

TABLE 4

BV1 and BV2 real-time PCR primers and probes

| Primer/Probe | Product (bp) | Sequence | SEQ ID NO: |
|---|---|---|---|
| BPH virus | | | |
| BV forward | | TTGTGGCCCAWTCTGTATC | 71 |
| BV reverse | | ACCGAAAGCAAAAATTCAG | 72 |
| BV1 probe | 129 | TCCGCCACTGTACGTGGCTTTG* | 73 |
| BV2 probe | 140 | CCTCTCCTTTGACCGAGGGATACGT* | 74 |

TABLE 4-continued

BV1 and BV2 real-time PCR primers and probes

| Primer/Probe | Product (bp) | Sequence | SEQ ID NO: |
|---|---|---|---|
| RNase P | | | |
| RNase P forward | | CAGGTTAACTACAGCTCCCAG | 75 |
| RNase P reverse | | GTCCAAATCTGCAAACACCG | 76 |
| RNase P probe | | TGAAGTCCCATGACCGTCCGC* | 77 |

*probe includes internal ZEN quencher 9 bases from the 5' fluorophore

Figure 6:
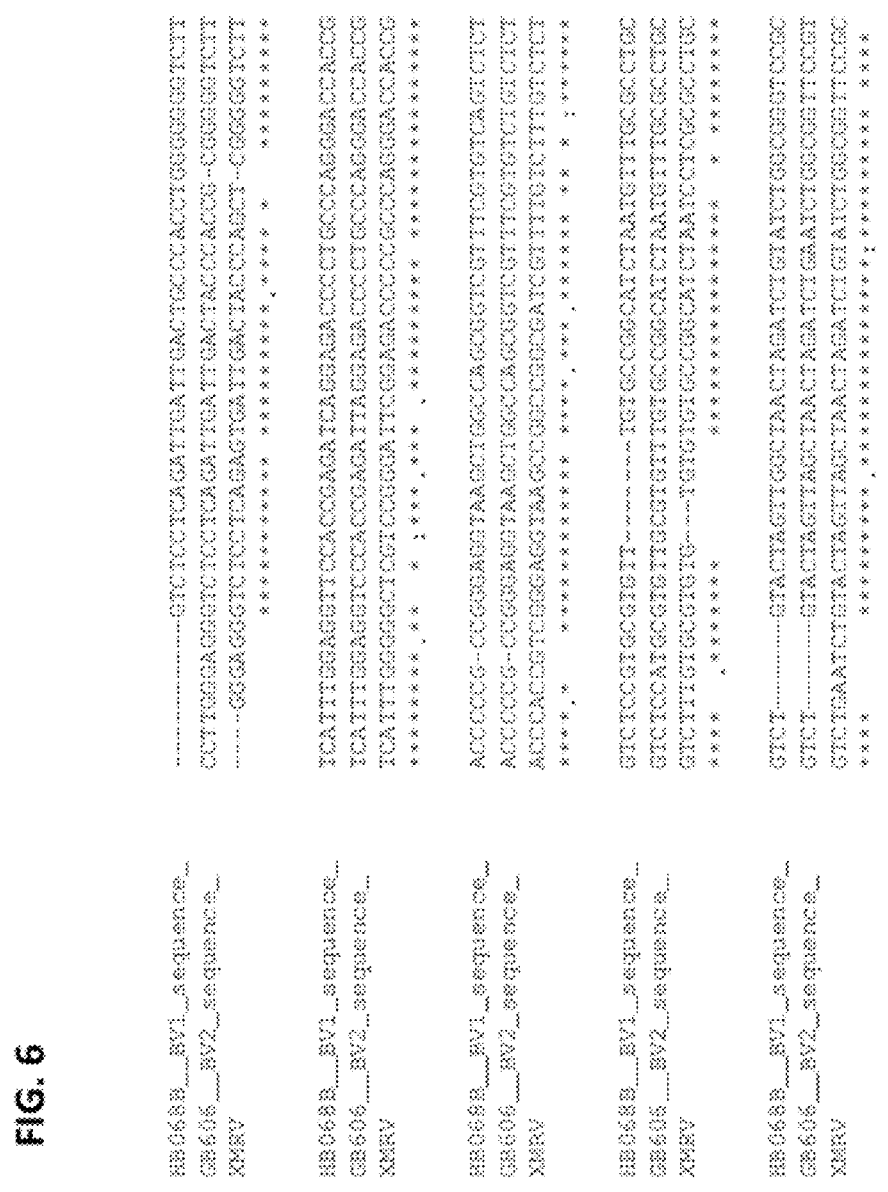

Primers and probes were obtained from Integrated DNA Technologies (Coralville, Iowa). Probes were labeled at the 5' end with FAM and quenched with a ZEN™ internal quencher and Iowa Black® FQ at the 3' end. BPH virus PCR reactions included 300 nM of each primer (BV forward and BV reverse), 200 nM of probe (either BV1 probe or BV2 probe), 100 ng DNA, and SsoFast™ Supermix (Bio-Rad, Hercules, Calif.) in a 20 µl reaction. Thermocycling was 4.5 minutes at 94° C., followed by 50 cycles of 5 seconds at 94° C. and 30 seconds at 62° C. on an iQ™5 thermocycler with real-time data collection (Bio-Rad). RNase P was used as a positive control to detect genomic DNA in the sample. RNase P PCR reactions included 1.25 µM of each primer (RNase P forward and RNase P reverse), 250 nM probe, 100 ng of DNA, and iQ™ Supermix (Bio-Rad) in a 20 µl reaction. Thermocycling was 3 minutes at 94° C., followed by 45 cycles of 15 seconds at 94° C. and 60 seconds at 58° C. on an iQ™5 thermocycler with real-time data collection (Bio-Rad). The BV1 and BV2 probes were designed against a region that has a 24 nucleotide deletion in XMRV, therefore, the probes are specific for BPH virus. An alignment of the gag region from a BV1 sample, a BV2 sample, and XMRV is shown in FIG. 6. The alignment indicates the location of the forward and reverse primers and the BV1 and BV2 probes. The alignment also indicates the 24 nucleotide deletion in XMRV as compared to BV1 and BV2.

Example 4

Methylation of BPH Virus LTR Region

This example describes detection of methylation of LTR region in BPH virus positive samples.

Bisulfite modified DNA was prepared from BPH TURP tissue samples positive for the BPH virus gag region (as described in Collard et al., *Prostate* 66:687-695, 200. Methylation specific real-time PCR was performed with BPHV meth F (AGGGATTATCGATTTATCGTC; SEQ ID NO: 78) and BPHV meth R (AATTCAAACGCAAACGCG; SEQ ID NO: 79) primers using IQ Sybr green supermix. Cycling conditions were 95° C. for 8.5 minutes, followed by 60 cycles of 95° C. for 15 seconds and 53.7° C. for 1 minute, followed by 71 cycles of 60° C. for 30 seconds.

Samples from three patients positive for BPH virus were tested. One sample had a methylated LTR, based on these primers. The presence of methylation may indicate that the virus was expressed less in this patient.

Example 5

Anti-Viral Response in BPH Samples

This example describes the presence of an anti-viral response in samples from subjects with symptomatic BPH.

Inflammation is commonly observed in BPH. In support of this and our data demonstrating the presence of virus in symptomatic BPH/TURP samples, an anti-viral immune response was observed in BPH samples. Expression of genes involved in the anti-viral immune response was measured in BPH tissues from men undergoing transurethral resection of the prostate (TURP) to alleviate symptoms, asymptomatic BPH (histologic BPH obtained from men undergoing prostatectomy for prostate cancer with AUA symptom scores less than 12), no BPH (normal transitional zone from cancer patients), and histologically normal prostate tissue from organ donors.

Complement factor I (CFI) was significantly upregulated in the tissue samples from symptomatic patients when compared to the other three tissue types (p<0.012). CFI inactivates C3b and C4b, two key players in activation of the complement pathway. Additionally, 2'-5'-oligoadenylate synthase (OAS2) was significantly upregulated in symptomatic BPH compared to asymptomatic BPH (p=0.004). OAS proteins recognize the double-stranded RNA of viruses. Without being bound by theory, it is believed that in the presence of virus in symptomatic BPH, CFI expression is deactivating the complement pathway, allowing for viruses to infect cells of the prostate. OAS2 is then likely being induced due to the presence of virus.

Example 6

Detection of BPH Virus in a Sample

This example describes exemplary methods that can be used to detect a BPH virus nucleic acid, polypeptide, or antibody in a sample from a subject. However, one skilled in the art will appreciate that methods that deviate from these specific methods can also be used to successfully detect a BPH virus nucleic acid, polypeptide, or antibody in a sample. In some examples, detecting a BPH virus nucleic acid, polypeptide, or antibody in a sample from a subject diagnoses the subject as having BPH or at risk of developing BPH.

Clinical samples are obtained from a subject (such as a subject suspected of having BPH or suspected of having BPH), such as a prostate tissue sample, a urine sample, or a blood sample. In some examples, nucleic acids are extracted from the sample using routine methods (for example using a commercial kit).

In one example, real-time PCR is performed in a reaction including a reaction mix (e.g., buffers, $MgCl_2$, dNTPs, and DNA polymerase), sample DNA, and probes and primers. The probes and primers are included in the reaction as follows: 300 nM each of BV forward primer (SEQ ID NO: 71) and BV reverse primer (SEQ ID NO: 72) and 200 nM of BV1 probe (SEQ ID NO: 73) or BV2 probe (SEQ ID NO: 74). Probes are labeled with 5' FAM, internal ZEN™ quencher, and 3' Iowa Black® FQ. The assay is performed using a real-time PCR system (such as the iQ™ system, Bio-Rad). Exemplary thermocycling conditions are 4.5 minutes at 94° C., followed by 50 cycles of 94° C. for 5 seconds and 62° C. for 30 seconds. Positive samples are those with a positive $C_t$ value for one or more BPH virus probes.

In another example, a BPH virus polypeptide is detected in a subject utilizing an enzyme immunoassay such as IFA, ELISA or immunoblotting. An exemplary ELISA method effective for the detection of BPH virus antibodies can, for example, be as follows: 1) bind a BPH virus polypeptide (such as a polypeptide of SEQ ID NOs: 39-58, or at least 8 consecutive amino acids thereof) to a substrate; 2) contact the bound polypeptide with a fluid or tissue sample from the subject; 3) contact the above with a secondary antibody bound to a detectable moiety which is reactive with the bound antibody (for example, horseradish peroxidase enzyme or alkaline phosphatase enzyme); 4) contact the above with the substrate for the enzyme; 5) contact the above with a color reagent; and 6) observe/measure color change or development.

In some examples, detection of a BPH virus nucleic acid, polypeptide, and/or antibody in a sample from a subject indicates that the subject has or is at risk of developing BPH. In further examples, a therapy is selected for a subject diagnosed with BPH virus, BPH, or risk of BPH, for example, antiviral therapy, 5-alpha-reductase inhibitor, anti-androgen, alpha-1-adrenergic antagonist, gonadotropin-releasing hormone agonist, or a combination of two or more thereof.

Example 7

Methods of Treating or Inhibiting BPH in a Subject

This example describes methods that can be used to treat a subject that has or is at risk of having BPH that can be treated by eliciting an immune response to a BPH virus polypeptide described herein. In particular examples, the method includes selecting a subject having, thought to have, or at risk of having BPH. Subjects having or thought to have BPH include those with symptoms such as nocturia, frequent urination, urinary urgency, weak or intermittent urinary stream, and enlarged prostate (for example detected by digital rectal exam). Subjects at risk of BPH include males over 40 years of age, family history of BPH, diabetes, obesity, and/or circulatory disease.

Subjects selected for treatment can be administered a therapeutic amount of a disclosed BPH virus polynucleotide, a polypeptide encoded by the disclosed polynucleotides, or an immunogenic fragment thereof. In some examples, a BPH virus polypeptide or immunogenic fragment thereof is administered at doses of 1 µg/kg body weight to about 1 mg/kg body weight per dose, such as about 1 µg/kg body weight-100 µg/kg body weight per dose, 100 µg/kg body weight-500 µg/kg body weight per dose, or about 500 µg/kg body weight to 1000 µg/kg body weight per dose. However, the particular dose can be determined by a skilled clinician. The disclosed BPH virus polynucleotide or polypeptide (or immunogenic fragment thereof) can be administered in one or several doses, for example continuously, daily, weekly, or monthly. When administered sequentially the time separating the administration of the disclosed BPH virus polynucleotide or polypeptide (or immunogenic fragment thereof) can be seconds, minutes, hours, days, or even weeks.

The mode of administration can be any used in the art. The amount of agent administered to the subject can be determined by a clinician, and may depend on the particular subject treated. Specific exemplary amounts are provided herein (but the disclosure is not limited to such doses).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of detecting benign prostatic hyperplasia (BPH) virus in a human subject, comprising:
    contacting a sample obtained from the human subject with a detectably labeled probe comprising the nucleic acid sequence of SEQ ID NO: 73 or SEQ ID NO: 74, a forward primer comprising the nucleic acid sequence of SEQ ID NO: 71 and a reverse primer comprising the nucleic acid sequence of SEQ ID NO: 72;
    carrying out real-time PCR; and
    detecting the detectably labeled probe, thereby detecting presence of BPH virus in the human subject.

2. The method of claim 1, wherein the sample obtained from the subject comprises prostate tissue.

3. The method of claim 1, wherein presence of BPH virus in the subject indicates the subject has BPH or is at risk of BPH.

4. The method of claim 3, further comprising selecting a therapy for the subject.

* * * * *

SEQUENCE LISTING

<160> NUMBER OF SEQ ID NOS: 126

<210> SEQ ID NO 1
<211> LENGTH: 464
<212> TYPE: DNA
<213> ORGANISM: Benign prostatic hyperplasia virus

<400> SEQUENCE: 1

| ccttgggagg gtctcctcag attgattgac tacccacgtc gggggtcttt catttggagg | 60 |
| ttccaccgag atttggagac ccctgcccag ggaccaccga ccccccgccg ggaggtaagc | 120 |
| tggccagcgg tcgtttcgtg tctgtctctg tcttcgtgcg tgtttgtgcc ggcatccaat | 180 |
| gtttgcgcct gcgtctgtac tagttagcta actagatctg tatctggcgg ttccgcggaa | 240 |
| gaactgacga gttcgtattc ccggccgcag ccccctgggag acgtcccagc ggcctcgggg | 300 |
| gcccgttttg tggcccattc tgtatcagtt aacctacccg agtcggactt tttggagctc | 360 |
| cgccactgta cgtggctttg ttgggggacg agagacagag acacttcccg cccccgtctg | 420 |
| gattttttgct ttcggttttta cgccgaaacc gcgccgcgcg tctg | 464 |

<210> SEQ ID NO 2
<211> LENGTH: 463
<212> TYPE: DNA
<213> ORGANISM: Benign prostatic hyperplasia virus

<400> SEQUENCE: 2

| ccttgggagg gtctcctcag attgattgac tacccacgtc gggggtcttt catttggagg | 60 |
| ttccaccgag atttggagac ccctgcccag ggaccaccga ccccccgccg ggaggtaagc | 120 |
| tggccagcgg tcgtttcgtg tctgtctctg tcttcgtgcg tgtttgtgcc ggcatccaat | 180 |
| gtttgcgcct gcgtctgtac tagttagcta actagatctg tatctggcgg ttccacggaa | 240 |
| gaactgacga gttcgtactc ccggccgcag ccccctgggag acgtcccagc ggcctcgggg | 300 |
| gcccgttttg tggcccattc tgtagcagtt aacctacccg agtcggactt tttggagctc | 360 |
| cgccactgta cgtggctttg ttgggggacg agagacagag acacttcccg cccccgtctg | 420 |
| aattttgctt tcggtttttac gccgaaaccg cgccgcgcgt ctg | 463 |

<210> SEQ ID NO 3
<211> LENGTH: 464
<212> TYPE: DNA
<213> ORGANISM: Benign prostatic hyperplasia virus

<400> SEQUENCE: 3

| ccttgggagg gtctcctcag attgattgac tacccacgtc gggggtcttt catttggagg | 60 |
| ttccactgag atttggagac ccctgcccag ggaccaccga ccccccgccg ggaggtaagc | 120 |
| tggccagcgg tcgtttcgtg tctgtctctg tcttcgtgcg tgtttgtgcc ggcatccaat | 180 |
| gtttgcgcct gcgtctgtac tagttagcta actagatctg tatctggcgg ttccgcggaa | 240 |
| gaactgacga gttcgtattc ccggccgcag ccccctgggag acgtcccagc ggcctcgggg | 300 |
| gcccgttttg tggcccattc tgtatcagtt aacctacccg agtcggactt tttggagctc | 360 |
| cgccactgta cgtggctttg ttgggggacg agagacagag acacttcccg cccccgtctg | 420 |
| aattttgct ttcggtttta tgccgaaacc gcgccgcgcg tctg | 464 |

<210> SEQ ID NO 4
<211> LENGTH: 462
<212> TYPE: DNA
<213> ORGANISM: Benign prostatic hyperplasia virus

<400> SEQUENCE: 4

```
ccttgggagg gtctcctcag attgattgac tgcccacctg ggggtctttt catttggagg        60
tcccaccgag atcaggagac ccctgcccag ggaccaccga ccccgccgg gaggtaagct        120
ggccagcggt cgtttcgtgt ctgtctctgt ctccgtgcgt gtttgtgccg gcatctaatg       180
tttgcgcctg cgtctgtact ggttggctaa ctagatctgt atctggcggt tccgtggaag       240
aactgacgag ttcgtattcc cggccgcagc cctgggagac gtcccagcgg cctcgggggc       300
ccgttttgtg gcccattctg tatcagttaa cctacccgag tcggactttt tggagctcct       360
ccactgtacg tggctttgtc ggggacgag aggcagagac acttccctcc cccgtctgaa        420
tttttgcttt cggttttacg ccgaaaccgc ccgcgcgtc tg                            462
```

<210> SEQ ID NO 5
<211> LENGTH: 463
<212> TYPE: DNA
<213> ORGANISM: Benign prostatic hyperplasia virus

<400> SEQUENCE: 5

```
ccttgggagg gtctcctcag attgattgac tgcccacctg ggggtctttt catttggagg        60
ttccaccgag atcaggagac ccctgcccag ggaccaccga ccccgccgg gaggtaagct        120
ggccagcggt cgttttgtgt ctgtctctgt ctccgtgcgt gtttgtgccg gcatctaatg       180
tttgcgcctg cgtctgtact agttggctaa ctagatctgt atctggcggt ttcgcggaag       240
aactgacgag ttcgtattcc cggccgcagc cctgggagac gtcccagcgg gcctcggggg       300
cccgttttgt ggcccattct gtatcagtta aactacccga gtcggactttt ttggagctcc      360
gccactgtac gtggctttgt tggggacga gagacagaga cacttcccgc cccgtctgg         420
atttttgctt tcggttttac gccgaaaccg ccgcgcgt ctg                            463
```

<210> SEQ ID NO 6
<211> LENGTH: 465
<212> TYPE: DNA
<213> ORGANISM: Benign prostatic hyperplasia virus

<400> SEQUENCE: 6

```
ccttgggagg gtctcctcag attgattgac tacccacgtc ggggtatttt catttggagg        60
ttccaccgag atttggagac ccctgcccag ggaccaccga ccccccgtcg ggaggtaagc       120
tggccagcgg tcgtttcgtg tctgtctctg tcttcgtgcg tgtttgtgcc ggcatccaat       180
gtttgcgcct gcgtctgtac tagttacgct aactagatct gtatctggag gatccgcgga      240
agaactgagg agttcgtatt cccggccgca gccctggga gacgtcccag tggcctcggg        300
ggcccggttt gtggtccatt ctgtatcact gaacctaccc gagtctgact ttttggagct      360
ccgccactgt acgtgggttt ggtggggac gagagacaga gacacttccc gccccgtct        420
ggattttgc tttcggcttt acgccgaaac cgcgccgcgc gtctg                        465
```

<210> SEQ ID NO 7
<211> LENGTH: 464
<212> TYPE: DNA
<213> ORGANISM: Benign prostatic hyperplasia virus

<400> SEQUENCE: 7

```
ccttgggagg gtctcctcag attgattgac tgcccacctg ggggggtctt tcatttggag        60
gttccaccga gatcaggaga ccctgcccca gggaccaccg accccgccg ggaggtaagc       120
```

| | |
|---|---|
| tggccagcgg tcgtttcgtg tctgtctctg tctccgtgcg tgtttgtgcc ggcatctaat | 180 |
| gtttgcgcct gcgtctgtac tagttggcta actagatctg tatctggcgg ttccgcggaa | 240 |
| gaactgacga gttcgtattc ccggccgcag cccctgggag acgtcccagc ggcctcgggg | 300 |
| gcccgttttg tggcccattc tgtatcagtt aacctacccg agtcggactt tttggagctc | 360 |
| cgccactgta cgtggctttg ttggggggacg agagacagag acacttcccg cccccgtctg | 420 |
| gattttttgct ttcggtttta cgccgaaacc gcgccgcgcg tctg | 464 |

<210> SEQ ID NO 8
<211> LENGTH: 464
<212> TYPE: DNA
<213> ORGANISM: Benign prostatic hyperplasia virus

<400> SEQUENCE: 8

| | |
|---|---|
| ccttgggagg gtctcctcag attgattgac tacccacgtc gggggtctttt catttggagg | 60 |
| tcccaccgag atttggagac ccctgcccag ggaccaccga tccccgccg ggaggtaagc | 120 |
| tggccagcgg tcgtttcgtg tctgtctctg tcttcgtgcg tgtttgtgcc ggcatccaat | 180 |
| gtttgcgcct gcgtctgtac tagttagcta actagatctg tatctggcgg ttccgcggaa | 240 |
| gaactgacga gttcgtattc ccggccgcag cccctgggag acgtcccagc ggcctcgggg | 300 |
| gcccgttttg tggcccattc tgtatcagtt aacctacccg agtcggactt tttggagctc | 360 |
| cgccactgta cgtggctttg ttggggggacg agagacagag acacttcccg cccccgtctg | 420 |
| aattttttgct ttcggtttta tgccgaaacc gcgccgcgcg tctg | 464 |

<210> SEQ ID NO 9
<211> LENGTH: 464
<212> TYPE: DNA
<213> ORGANISM: Benign prostatic hyperplasia virus

<400> SEQUENCE: 9

| | |
|---|---|
| ccttgggagg gtctcctcag attgattgac tacccacgtt cggggggtctt tcatttggag | 60 |
| gttccaccga gatttggaga cccatgccca gggaccaccg accccgccg ggaggtaagc | 120 |
| tggccagcgg tcgtttcgtg tctgtctctg tctccgtgcg tgtttgtgcc ggcatccaat | 180 |
| gtttgcgcct gcgtctgtac tagttagcta actagatctg tatctggcgg taccgcggaa | 240 |
| gaactgacga gttcgtattc ccggccgcag cccctgggag acgtcccagc ggcctcgggg | 300 |
| gcccgttttg tggcccattc tgtatcagtt aacctacccg agtcggactt tttggagctc | 360 |
| cgccactgta cgtggctttg ttggggggacg agagacagag acacttcccg cccccgtctg | 420 |
| aattttttgct ttcggtttta tgccgaaacc gcgccgcgcg tctg | 464 |

<210> SEQ ID NO 10
<211> LENGTH: 454
<212> TYPE: DNA
<213> ORGANISM: Benign prostatic hyperplasia virus

<400> SEQUENCE: 10

| | |
|---|---|
| gtctcctcag attgattgac tgcccacctg gggggggtctt tcatttggag gttccaccga | 60 |
| gatcaggaga ccctgcccca gggaccaccg accccgccg ggaggtaagc tggccagcgg | 120 |
| tcgtttcgtg tcagtctctg tctccgtgcg tgtttgtgcc ggcatctaat gtttgcgcct | 180 |
| gcgtctgtac tagttggcta actagatctg tatctggcgg gtccgcggaa gaactgacga | 240 |
| gttcgtattc ccggccgcag cccctgggag acgtcccagc ggcctcgggg gcccgttttg | 300 |
| tggcccattc tgtatcagtt aacctacccg agtcggactt tttggagctc cgccactgta | 360 |

```
cgtggctttg ttgggggacg agagacagag acacttcccg cccccgtctg aattttttgct    420 ttcggtttta tgccgaaacc gcgccgcgcg tctg                                 454

<210> SEQ ID NO 11
<211> LENGTH: 469
<212> TYPE: DNA
<213> ORGANISM: Benign prostatic hyperplasia virus

<400> SEQUENCE: 11
ccttgggagg gtctcctcag attgattgac tacccacgtc ggggtcttt catttggagg     60 ttccactgag atttggagac ccctgcccag ggaccaccga cccccgccg ggaggtaagc    120 tggccagcgg tcgtttcgtg tctgtctctg tcttcgtgcg tgtttgtgcc ggcatccaat   180
gtttgcgcct gcgtctgtac tagttagcta actagatctg tatctggcgg ttccgcggaa   240
gaactgacga gttcgtattc ccggccgcag ccctgggag acgtcccagc ggcctcgggg   300
gcccgttttg tggcccattc tgtatcagtt aacctacccg agtcggactt tttggagctc   360
cgccactgta cgtggctttg ttgggggacg agagacagag acacttcccg ccccgtctg    420 aattttttgct ttcggtttta cgccgaaacc gcgccgcgcg tctgaatcg              469

<210> SEQ ID NO 12
<211> LENGTH: 464
<212> TYPE: DNA
<213> ORGANISM: Benign prostatic hyperplasia virus

<400> SEQUENCE: 12
ccttgggagg gtctcctcag attgattgac tacccacgtc ggggtcttt catttggagg     60 ttccaccgag atttggagac ccctgcccag ggaccaccga cccccgccg ggaggtaagc    120 tggccagcgg tcgtttcgtg tctgtctctg tcttcgtgcg tgtttgtgcc ggcatccaat   180
gtttgcgcct gcgtctgtac tagttagcta actagatctg tatctggcgg ttccgcggaa   240
gaactgacga gttcgtattc ccggccgcag ccctgggag acgtcccagc ggcctcgggg   300
gcccgttttg tggcccattc tgtatcagtt aacctacccg agtcggactt tttggagctc   360
cgccactgta cgtggctttg ttggggggcg agagacagag acacttcccg ccccgtctg    420 gattttttgct ttcggtttta cgccgaaacc gcgccgcgcg tctg                   464

<210> SEQ ID NO 13
<211> LENGTH: 465
<212> TYPE: DNA
<213> ORGANISM: Benign prostatic hyperplasia virus

<400> SEQUENCE: 13
ccttgggagg gtctcctcag attgattgac tacccacgtc ggggtcttt catttggagg     60 ttccaccgag atttggagac ccctgcccag ggaccaccga ccccccgcc gggaggtaag    120 ctggccagcg tcgtttcgt gtctgtctct gtcttcgtgc gtgtttgtgc cggcatccaa    180
tgtttgcgcc tgcgtctgta ctagttagct aactagatct gtatctggcg gttccgcgga   240
agaactgacg agttcgtatt ccggccgca gccctgggaa gacgtcccag cggcctcggg    300
ggcccgtttt gtggcccatt ctgtatcagt taacctaccc gagtcggact ttttggagct   360
ccgccactgt acgtggcttt gttggggac gagagacaga gacacttccc gccccgtct    420 gaattttttgc tttcggtttt acgccgaaac cgcgccgcgc gtctg                  465

<210> SEQ ID NO 14
```

```
<211> LENGTH: 466
<212> TYPE: DNA
<213> ORGANISM: Benign prostatic hyperplasia virus

<400> SEQUENCE: 14
ccttgggagg gtctcctcag attgattgac tacccacgtc gggggtctttt catttggagg      60
tcccaccgag atttggagac ccctgcccag ggaccaccga ccccccgcc gggaggtaag       120
ctggccagcg tcgtttcgt gtctgtctct gtcttcgtgc gtgtttgtgc cggcatccaa      180
tgtttgcgcc tgcgtctgta ctagttagct aactagatct gtatctggcg gttccgcgga    240
agaactgacg agttcgtatt cccggccgca gccctggga gacgtcccag cggcctcggg     300
ggcccgtttt gtggcccatt ctgtatcagt taacctaccc gagtcggact ttttggagct    360
ccgccactgt acgtggcttt gttggggac gagaaacaga gacacttccc gccccgtct      420
gaattttttgc tttcggtttt acgccgaaac cgcgccgcgc gtctga                    466

<210> SEQ ID NO 15
<211> LENGTH: 435
<212> TYPE: DNA
<213> ORGANISM: Benign prostatic hyperplasia virus

<400> SEQUENCE: 15
tctcctcaga ttgattgacc acccacctcg ggggtctttc atttggaggt tccaccgaga    60
ttaggagacc cctgcccagg gaccaccgac ccccgccggg aggtaagctg ccagcggtc     120
gtttcgtgtc tgtctctgtc tccgtgcgtg tttgtgccgg catctaatgt tgcgcctgc    180
gtctgtacta gttggctaac tagatctgaa tctggcggtt ccgtggaaga actgacgagt    240
tcatattccc ggccgcagcc ctgggagacg tctcagaggc atcgggggcc atctttgtgg    300
cccaatctgt atctgagaac ccgacccgtc tcggactcct tggagcctct cctttgaccg    360
agggatacgt ggttctgttg gcggcgagg ggccgaaacg ctcctctccc ccatctgaat   420
ttttgctttc ggttt                                                     435

<210> SEQ ID NO 16
<211> LENGTH: 464
<212> TYPE: DNA
<213> ORGANISM: Benign prostatic hyperplasia virus

<400> SEQUENCE: 16
ccttgggagg gtctcctcag attgattgac tacccacgtc gggggtcttt catttggagg   60
ttccactgag atttggagac ccctgcccag ggaccaccga ccccccgccg ggaggtaagc  120
tggccagcgg tcgtttcgtg tctgtctctg tcttcgtgcg tgtttgtgcc ggcatccaat  180
gtttgcgcct gcgtctgtac tagttagcta actagatctg tatctggcgg ttccgcggaa  240
gaactgacga gttcgtattc ccggccgcag ccctgggag acgtcccagc ggcctcgggg   300
gcccgttttg tggcccattc tgtatcagtt aacctacccg agtcggactt tttggagctc  360
cgccactgta cgtggctttg ttgggggacg agagacagag acacttcccg ccccgtctg   420
aatttttgct ttcggtttta cgccgaaacc gcgccgcgcg tctg                    464

<210> SEQ ID NO 17
<211> LENGTH: 480
<212> TYPE: DNA
<213> ORGANISM: Benign prostatic hyperplasia virus

<400> SEQUENCE: 17
ccttgggagg gtctcctcag attgattgac tacccaccgc gggggtcttt catttggagg   60
```

```
tcccaccgag attaggagac ccctgcccag ggaccaccga ccccgccgg gaggtaagct    120 ggccagcggt cgtttcgtgt ctgtctctgt ctccatgcgt gttgcgtgtt tgtgccggca    180
tctaatgttt gcgcctgcgt ctgtactagt tagctaacta gatctgaatc tggcggttcc    240
gtggaagaac tgacgagttc atattcccgg ccgcagccct gggagacgtc tcagaggcat    300
cgggggccat ctttgtggcc caatctgtat ctgagaaccc gacccgtctc ggactctttg    360
gagcctctcc tttgaccgag ggatacgtgg ttctgttggg cggcgagggg ccgaaacgct    420
cctccccccc catctgaatt tttgctttcg gttttccgcc gaaaccgcgc gcgcgtctg    480
```

<210> SEQ ID NO 18
<211> LENGTH: 472
<212> TYPE: DNA
<213> ORGANISM: Benign prostatic hyperplasia virus

<400> SEQUENCE: 18

```
ccttgggagg gtctcctcag attgattgac cacccacctc ggggtctttt catttggagg     60
ttccaccgag attaggagac ccctgcccag ggaccaccga ccccgccgg gaggtaagct    120 ggccagcggt cgtttcgtgt ctgtctctgt ctccgtgcgt gtttgtgccg gcatctaatg    180
tttgcgcctg cgtctgtact agttggctaa ctagatctga atctggcggt tccgtggaag    240
aactgacgag ttcatattcc cggccgcagc cctgggagac gtctcagagg catcgggggc    300
catctttgtg gcccaatctg tatctgagaa cccgacccgt ctcggactcc ttggagcctc    360
tcctttgacc gagggatacg tggttctgtt gggcggcgag gggccgaaac gctcctctcc    420
cccatctgaa ttttgcttt cggttttccg ccgaaaccgc gccgcgcgtc tg           472
```

<210> SEQ ID NO 19
<211> LENGTH: 472
<212> TYPE: DNA
<213> ORGANISM: Benign prostatic hyperplasia virus

<400> SEQUENCE: 19

```
ccttgggagg gtctcctcag attgattgac cacccatctc ggggtctttt catttggagg     60
ttccaccgag attaggagac ccctgcccag ggaccaccga ccccgccgg gaggtaagct    120 ggccagcggt cgtttcgtgt ctgtctctgt ctccgtgcgt gtttgtgccg gcatctaatg    180
tttgcgcctg cgtctgtact agttggctaa ctagatctga atctggcggt tccgtggaag    240
aactgacgag ttcatattcc cggccgcagc cctgggagac gtctcagagg catcgggggc    300
catctttgtg gcccaatctg tatctgagaa cccgacccgt ctcggactcc ttggagcctc    360
tcctttgacc gagggatacg tggttctgtt gggcggcgag gggccgaaac gctcctctcc    420
cccatctgaa ttttgcttt cggttttccg ccgaaaccgc gccgcgcgtc tg           472
```

<210> SEQ ID NO 20
<211> LENGTH: 415
<212> TYPE: DNA
<213> ORGANISM: Benign prostatic hyperplasia virus

<400> SEQUENCE: 20

```
ccttgggagg gtctcctcag attgattgac tacccacgtc ggggtctttt catttggagg     60
tcccaccgag atttggagac ccctgcccag ggaccaccga tccccgccg ggaggtaagc    120 tggccagcgg tcgtttcgtg tctgtctctg tcttcgtgcg tgtttgtgcc ggcatccaat    180
gtttgcgcct gcgtctgtac tagttagcta actagatctg tatctggcgg ttccgcggaa    240
```

```
gaactgacga gttcgtattc ctggccgcag ccctgggag acgtcccagc ggcctcgggg     300
gcccgttttg tggcccattc tgtatcagtt aacctacccg agtcggactt tttggagctc    360
cgccactgta cgtggctttg ttgggggacg agagacagag acacttcccg ccccc         415
```

<210> SEQ ID NO 21
<211> LENGTH: 470
<212> TYPE: DNA
<213> ORGANISM: Benign prostatic hyperplasia virus

<400> SEQUENCE: 21

```
ccttgggagg gtctcctcag attgattgac tacccacctc ggggtctttt catttggagg     60
tcccaccgag attaggagac ccctgcccag ggaccaccga ccccgccgg gaggtaagct     120 ggccagcggt cgtttcgtgt ctgtctctgt ctccgtgcgt gtttgtgccg gcatctaatc    180
tttgcgcctg cgtctgtact agttggctaa ctagatctgt atctggcggt tccgcggaag    240
aactgacgag ttcgtattcc ggccgcagc cctgggagac gtcccagcgg cctcggggc      300 ccgttttgtg gcccattctg tatcagttaa ctgcccgag tcggattttt ttggagctcc     360
tccactgtcc gaggggtacg tggctttgtc ggggacgag aggcagagac acttccctcc    420
cccgtctgaa ttttgctttt cggttttacg ccgaaaccgc gccgcgcgtc                470
```

<210> SEQ ID NO 22
<211> LENGTH: 536
<212> TYPE: DNA
<213> ORGANISM: Benign prostatic hyperplasia virus

<400> SEQUENCE: 22

```
ccttgggagg gtctcctcag attgattgac tacccaccgc ggggtctttt catttggagg     60
tcccaccgag attaggagac ccctgcccag ggaccaccga ccccgccgg gaggtaagct    120 ggccagcggt cgtttcgtgt ctgtctctgt ctccgtgcgt gttgcgtgtt tgtgccggca    180
tctaatgttt gcgcctgcgt ctgtactagt tagctaacta gatctgaatc tggcggttcc    240
gtggaagaac tgacgagttc atattcccgg ccgcagccct gggagacgtc tcagaggcat    300
cgggggccat ctttgtggcc caatctgtat ctgagaaccc gacccgtctc ggactctttg    360
gagcctctcc tttgaccgag ggatacgtgg ttctgtcggg cggcgagggg ccgaagcgct    420
cctccccccc catctgaatt tttgctttcg gttttccgcc gaaaccgcgc gcgcgtctg    480 acctccttgg gagggtctcc tcagttgcgg tgagccgaaa ccgcgccgcg cgtctg        536
```

<210> SEQ ID NO 23
<211> LENGTH: 476
<212> TYPE: DNA
<213> ORGANISM: Benign prostatic hyperplasia virus

<400> SEQUENCE: 23

```
ccttgggagg gtctcctcag attgattgac tacccaccgc ggggtcttc catttggagg      60 tcccaccgag attaggagac ccctgcccag ggaccaccga ccccgccgg gaggtaagct    120 ggccagcggt cgtttcgtgt ctgtctctgt ctccgtgcgt gttgcgtgtt tgtgccggca    180
tctaatgttt gcgcctgcgt ctgtactagt tagctaacta gatctgaatc tggcggttcc    240
gtggaagaac tgacgagttc atattcccgg ccgcagccct gggagacgtc tcagaggcat    300
cgggggccat ctttgtggcc caatctgtat ctgagaaccc gacccgtctc ggactctttg    360
gagcctctcc tttgaccgag ggatacgtgg ttctgttggg cggcgagggg ccgaaacgct    420
cctccccccc catctgaatt tttgctttcg gttttccgcc gaaaccgcgc cgcgcg         476
```

<210> SEQ ID NO 24
<211> LENGTH: 472
<212> TYPE: DNA
<213> ORGANISM: Benign prostatic hyperplasia virus

<400> SEQUENCE: 24

```
ccttgggagg gtctcctcag attgattgac cacccacctc ggggtctttt catttggagg      60
ttccaccgag attaggagac ccctgcccag ggaccaccga ccccgccgg gaggtaagct      120
ggccagcggt cgtttcgtgt ctgtctctgt ctccgtgcgt gtttgtgccg gcatctaatg    180
tttgcgcctg cgtctgtact agttggctaa ctagatctga atctggcggt tccgtggaag    240
aactgacgag ttcatattcc cggccgcagc cctgggagac gtctcagagg catcggggc     300
catctttgcg gcccaatctg tatctgagaa cccgacccgt ctcggactcc ttggagcctc    360
tcctttgacc gagggatacg tggttctgtt gggcggcgag gggccgaaac gctcctctcc    420
cccatctgaa ttttttgcttt cggttttccg ccgaaaccgc gccgcgcgtc tg           472
```

<210> SEQ ID NO 25
<211> LENGTH: 472
<212> TYPE: DNA
<213> ORGANISM: Benign prostatic hyperplasia virus

<400> SEQUENCE: 25

```
ccttgggagg gtctcctcag attgattgac cacccacctc ggggtctttt catttggagg      60
ttccaccgag attaggagac ccctgcccag ggaccaccga ccccgccgg gaggtaagct      120
ggccagcggt cgtttcgtgt ctgtctctgt ctccgcgcgt gtttgtgccg gcatctaatg    180
tttgcgcctg cgtctgtact agttggctaa ctagatctga atctggcggt tccgtggaag    240
aactgacgag ttcatattcc cggccgcagc cctgggagac gtctcagagg catcggggc     300
catctttgtg gcccaatctg tatctgagaa cccgacccgt ctcggactcc ttggagcctc    360
tcctttgacc gagggatacg tggttctgtt gggcggcgag gggccgaaac gctcctctcc    420
cccatctgaa ttttttgcttt cggttttccg ccgaaaccgc gccgcgcgtc tg           472
```

<210> SEQ ID NO 26
<211> LENGTH: 480
<212> TYPE: DNA
<213> ORGANISM: Benign prostatic hyperplasia virus

<400> SEQUENCE: 26

```
ccttgggagg gtctcctcag attgattgac tacccaccgc ggggtctttt catttggagg      60
tcccaccgag attaggagac ccctgcccag ggaccaccga ccccgccgg gaggtaagct      120
ggccagcggt cgtttcgtgt ctgtctctgt ctccgtgcgt gttgcgtgtt tgtgccggca    180
tctaatgttt gcgcctgcgt ctgtactagt tagctaacta gatctgaatc tggcggttcc    240
gtggaagaac tgacgagttc atattcccgg ccgcagccct gggagacgtc tcagaggcat    300
cgggggccat ctttgtggcc caatctgtat ctgagaaccc gacccgtctc ggactctttg    360
gagcctctcc tttgaccgag ggatacgtgg ttctgttggg cggcgagggg ccgaaacgct    420
cctcccccc catctgaatt tttgctttcg gttttccgcc gaaaccgcgc cgcgcgtccg     480
```

<210> SEQ ID NO 27
<211> LENGTH: 481
<212> TYPE: DNA
<213> ORGANISM: Benign prostatic hyperplasia virus

<400> SEQUENCE: 27

```
ccttgggagg gtctcctcag attgattgac tacccaccgc gggggtcttt catttggagg      60
tcccaccgag attaggagac ccctgcccag ggaccaccga ccccgccgg gaggtaagct      120
ggccagcggt cgtttcgtgt ctgtctctgt ctccgtgcgt gttgcgtgtt tgtgccggca     180
tctaatgttt gcgcctgcgt ctgtactagt tagctaacta gatctgaatc tggcggttcc     240
gtggaagaac tgacgagttc atattcccgg ccgcagccct gggagacgtc tcagaggcat     300
cgggggccat ctttgtggcc caatctgtat ctgagaaccc gacccgtctc ggactctttg     360
gagcctctcc tttgaccgag ggatacgtgg ttctgttggg cggcgagggg ccgaaacgct     420
cctcccccc ccatctgaat ttttgctttc ggttttccgc cgaaaccgcg ccgcgcgtct    480
g                                                                     481
```

<210> SEQ ID NO 28
<211> LENGTH: 1057
<212> TYPE: DNA
<213> ORGANISM: Benign prostatic hyperplasia virus

<400> SEQUENCE: 28

```
cctcaacctc accagtcccg acaaaaccca agagtgctgg ttgtgtctgg tatcgggacc      60
cccctactac gaaggggttg ccgtcctagg tacctactcc aaccatacct ctgccccagc     120
taactgctcc gtggcctccc aacacaagct gaccctgtcc gaagtgaccg acagggact      180
ctgcgtagga gcagttccca aaacccatca ggccctgtgt aataccaccc agaagacgag     240
cgacgggtcc tactatctgg ctgctcccgc cgggaccatc tgggcttgca acaccgggct     300
cactccctgc ctatctacta ctgtactcaa cctcaccacc gattactgtg tcctggttga     360
gctctggcca aaggtgaccct accactcccc tggttatgct tatggccagt ttgagagaaa     420
aaccaaatat aaaagagagc cggtgtcatt aactctggcc ctgctgttgg gaggacttac     480
tatgggcggc atagctgcag gagtaggaac agggactaca gccctagtgg ccaccaaaca     540
attcgagcag ctccaggcag ccatacatac agaccttagg gccttagaaa aatcagtcag     600
tgccctagaa aagtctctga cctcgttgtc tgaggtggtc ctacagaacc ggagaggatt     660
agatctgctg ttcctaaaag aaggaggatt atgtgctgcc ctaaaagaag aatgctgttt     720
ctacgcggac cacactggcg tagtgagaga tagcatggca aagctaagag aaaggttaaa     780
ccagagacaa aaattgttcg aatcaggaca agggtggttt gagggactgt taacaggtc     840
cccatggttc acgaccttga tatccaccat tatgggcccc ttgataatac ttttattaat     900
cctactcctc ggaccctgta ttctcaaccg cttggtccag tttgtaaaaa aagaatttcg     960
gggggggcagg ccctggttct gacccacagt atccccactc aattaataaa tcccaaaaaa    1020
aaggcgtccc tgcagaaaaa atttattatt tttccgg                              1057
```

<210> SEQ ID NO 29
<211> LENGTH: 1053
<212> TYPE: DNA
<213> ORGANISM: Benign prostatic hyperplasia virus

<400> SEQUENCE: 29

```
ccatgccttg caaaatggcg ttactgcagc tagcttgcta agcctgatgg tggggtcttt      60
cattccccc tctttctgga aactgaataa aatctttat tcacgtgatt ccacttcttc      120
tggatctatt gatttgagtt ggtgatactg ttgggtcaaa gccagggcct gcactaccga     180
aattctgtct tttacaaact ggaccaagcg gttgagaata cagggtccga agagtaggat     240
```

```
taataaaagt attatcaagg ggcccataat ggtagatatt aaggtcgtga accatgggga      300
cctgttaaac agtccctcag accacccttg tcctgattcg aacaattttt gtctctggtt      360
caacctttct cttagctttg ccatgctatc tcttactacg ccagtgtggt ccgcgtagaa      420
acagcattct tcttttaggg cagcacataa tcctccttct tttaggaaca gtagatctaa      480 tccctccgg ttctgtagga ccacctcaga caacgaggtc agagacttt ctagggcact        540 gactgacttt tctaaagccc caaggtctgt atgtatggct gcctggagct gctcgaattg      600
tttggtggcc actagggctg tagtcccggt tcctactcct gcagctatgc cgcccatagt      660
aagtcctccc aacagcaggg ccagagttaa tgacaccggc tctctttat atttggtttt       720 tttctcaaac tggccataaa cataaccagg ggagtggtag gtcacctttg ccagagctc       780 aaccaggaca cagtaatcgg tggttaagtt aagcacagta gtagatagac agggagtgag     840
cccggtgctg caggcccaaa tggtcccggc gggagaggcc aaatagtagg acccgtcgct     900
cgtcttctgg gtggtattac acagggcctg atggggtttt gggaactgc tcctacgcag      960 aaaccctggt ccggtccctt cggacagggt caccttgggt tggggaggcc cggaacagtt    1020
agctggggca aaaaagggt gggaaaaggt acc                                  1053
```

```
<210> SEQ ID NO 30
<211> LENGTH: 401
<212> TYPE: DNA
<213> ORGANISM: Benign prostatic hyperplasia virus

<400> SEQUENCE: 30
gggacgatga cagacacttt ccctaaacta tattttgact tgtgtggttt agttggagat       60
aactgggatg acccggaatc ctctagtgga catggttgcc gctctccgg ggaagaaaa        120 gggacaagaa catttgattt ctatgtttgc cccggtcata ctgtactaac agggtgtgga     180
gggccgaggg agggctactg tggcaaatgg ggatgtgaga ccactggaca ggcatactgg     240
aagccatcat catcatggga cctaattttcc cttaagcgag gaaacactcc taggagtcag    300 ggccctgtt atgattcctc agtggtctcc agtagcgtcc agggtgccac accggggggt      360
cgatgcaacc ccctagtcct agaattcact gacgcgggta a                         401
```

```
<210> SEQ ID NO 31
<211> LENGTH: 350
<212> TYPE: DNA
<213> ORGANISM: Benign prostatic hyperplasia virus

<400> SEQUENCE: 31
gggacgatga cagacacttt ccctaaacta tattttgact tgtgtgattt agttggagat       60
aactgggatg acccggaatc ctctagtgga catggttgcc gctctccgg ggaagaaaa        120 aggacaagaa catttgattt ctatgtttgc cccggtcata ctgtactaac agggtgtgga     180
gggccgaggg agggctactg tggcaaatgg ggatgtgaga ccactggaca ggcatactgg     240
aagccatcat catcatggga cctaattttcc cttaagcgag gaaacactcc taggagtcag    300 ggccctgtt atgattcctc agtggtctcc agtagcgtcc agggtgccac                 350
```

```
<210> SEQ ID NO 32
<211> LENGTH: 394
<212> TYPE: DNA
<213> ORGANISM: Benign prostatic hyperplasia virus

<400> SEQUENCE: 32
```

```
tacccgcgtc agtgaattct aggactaggg ggttgcatcg accccccggt gtggcaccct    60
ggacgccact ggagaccgag gaatcataac aggggccctg atccttagga gtgtttcctc   120
gcttaaggga aattaggtcc catgatgatg atggcttcca gtatgcctgt ccagtggtct   180
cacatcccca tttgccacag tagccctctc ccggccctcc acaccctatt ggtacagtat   240
gaccggggca aacatagaag tcatacagtc ttgtcctttt tcttcccccg ggagagcggc   300
aaccatctcc atctgggtca tcccaatccc agtagtctcc tactaaatca cacaggtcaa   360
aatatagttt agggaaagtg tctgtcatcg tccc                              394

<210> SEQ ID NO 33
<211> LENGTH: 388
<212> TYPE: DNA
<213> ORGANISM: Benign prostatic hyperplasia virus

<400> SEQUENCE: 33
tacccgcgtc agtgaattct aggactaggg ggttgcatcg accccccggt gtggcaccct    60
ggacgtcact ggagaccgag gaatcataac aggggccctg atccttagga gtgtttcctc   120
gcttaaggga aattaggtcc catgatgatg atggcttcca gtatgcctgt ccagtggtct   180
cacatcccca tttgccacag tagccctctc tcggccctcc acaccctatt ggtacagtat   240
gaccggggca aacatagaag tcatacagtc ttgtcctttt tcttcccccg ggagagcggc   300
aaccatctcc atctgggtca tcccagtagt ctcctactaa atcacacagg tcaaaatata   360
gtttagggaa agtgtctgtc atcgtccc                                     388

<210> SEQ ID NO 34
<211> LENGTH: 303
<212> TYPE: DNA
<213> ORGANISM: Benign prostatic hyperplasia virus

<400> SEQUENCE: 34
gggagcaaaa agcgcgggta cagaagcgag aagcgagctg attggttagt ttaaatgagg    60
cttggggttg atccccggtc atctggggaa ccttgagaca gtttctgggt ctcttgaaac   120
tgttgttgtt ttagctattt ctggggacca tctgttcttg gccctgggcc ggggccctag   180
tgcttgacca cagatacccct gtttggccct agtcccggta cttttcagcc tctctgtact   240
tccttgttct tgttttttctg agaacatcag ctctggtatt ttcccatgcc ttgcaaaatg   300
gcg                                                                303

<210> SEQ ID NO 35
<211> LENGTH: 354
<212> TYPE: DNA
<213> ORGANISM: Benign prostatic hyperplasia virus

<400> SEQUENCE: 35
cgccattttg caaggcatgg aaaagtacca gagctgagtt ctcaaaagtt acaaggaagt    60
tcagttaaag attaacagtt aaaaatcaag gctgaataat actaggacaa gggccaagaa   120
ccgatggtac ccaccggggc cccggctcaa ggccaagaac cgatggtacc cacctgggcc   180
ccggctcagg gccaagaaca gatggtaccc agataaggcg gaaccagcaa cagtttctaa   240
aaaagtccca cctcagtttc aggttcccca aatgaccagg aaatacccca gccttgatt   300 tgaactaacc actcagctcg cttctcgctt ctgtacccgc gcttttttgct cccc         354

<210> SEQ ID NO 36
<211> LENGTH: 477
```

```
<212> TYPE: DNA
<213> ORGANISM: Benign prostatic hyperplasia virus

<400> SEQUENCE: 36
cgccattttg caaggcatgg caaaagtacc agagctgagt tctcaaaagt tacaagaaag    60
ttcagttaaa gattaacagt taaagattaa ggctgaataa tactgggaca ggggccaaat   120
atcggtggtc aagcacctgg gccccggctc agggccaaga acagatggct ctcagacgtc   180
agtgttagca gaactagctt cactgattta gaaaaataga ggtgcacaat gctctggcca   240
ctccttgaac ctgtgtgtct gccaatgttc tgaccaggtg tgtgcccatt gctgcacctt   300
cattagactc tttccttgta cccctcccat acccatttct tgaaaataga cattgtttag   360
atctaaaaag ttccacctca gtttcaggtt ccccaaatga ccggaaaata ccccaaacct   420
tatttgaact aaccaaccag ctcgcttctt gcttctgtac ccgcgctttt tgctccc      477

<210> SEQ ID NO 37
<211> LENGTH: 367
<212> TYPE: DNA
<213> ORGANISM: Benign prostatic hyperplasia virus

<400> SEQUENCE: 37
cgccattttg caaggcatgg aaaagtacta gagctgagac ctcaaaagtt acaaggaagt    60
tcagttaaag tttaaggcta aataacaacg ggacaggggc caaacaggat atctatggtc   120
aagcacctgg gccccggctc agggccaaga acagatggta cccagataga gcggaaccag   180
caacagtttc gagactgccc caccagccaa gaacagatgg tacccagata gagcggaacc   240
agcaacagtt tcgagactgc cccacatcag tttcaaggtt ccccaaatgg ccgggacttt   300
cccctagcct tatttgaact aaccaatcag ctcgcttctc gcttctgtac ccgcgctttt   360
tgctccc                                                             367

<210> SEQ ID NO 38
<211> LENGTH: 304
<212> TYPE: DNA
<213> ORGANISM: Benign prostatic hyperplasia virus

<400> SEQUENCE: 38
gggagcaaaa agcgcgggta cagaagcgag aagcgagctg attggttagt ttaaataagg    60
cttggggtat ttcccggtca tttggggaac ctgaaactga ggtgggactt tccagaaact   120
gttgctagtt tcgctttatc tgagtaccat ctgttcttgg ccctgagccg ggcccaggt    180
gcttgaccac agatatcctg tttggcccct gtcccagtat tattcagcct tattcttaa    240
ctaaacttcc ttgtaacttt tgagaactca gctctggtac ttttccatgc cttgcaaaat   300
ggcg                                                                304

<210> SEQ ID NO 39
<211> LENGTH: 73
<212> TYPE: PRT
<213> ORGANISM: Benign prostatic hyperplasia virus

<400> SEQUENCE: 39

Leu Thr Ser Ser Tyr Ser Arg Pro Gln Pro Leu Gly Asp Val Pro Ala
1               5                   10                  15

Ala Ser Gly Ala Arg Phe Val Ala His Ser Val Ala Val Asn Leu Pro
            20                  25                  30

Glu Ser Asp Phe Leu Glu Leu Arg His Cys Thr Trp Leu Cys Trp Gly
        35                  40                  45
```

```
Thr Arg Asp Arg Asp Thr Ser Arg Pro Arg Leu Asn Phe Ala Phe Gly
        50                  55                  60

Phe Thr Pro Lys Pro Arg Arg Ala Ser
65                  70

<210> SEQ ID NO 40
<211> LENGTH: 72
<212> TYPE: PRT
<213> ORGANISM: Benign prostatic hyperplasia virus

<400> SEQUENCE: 40

Leu Thr Ser Ser Tyr Ser Arg Pro Gln Pro Trp Glu Thr Ser Gln Arg
1               5                   10                  15

Pro Arg Gly Pro Val Leu Trp Pro Ile Leu Tyr Gln Leu Thr Tyr Pro
                20                  25                  30

Ser Arg Thr Phe Trp Ser Ser Thr Val Arg Gly Phe Val Gly Gly
            35                  40                  45

Arg Glu Ala Glu Thr Leu Pro Ser Pro Val Ile Phe Ala Phe Gly Phe
        50                  55                  60

Thr Pro Lys Pro Arg Arg Ala Ser
65                  70

<210> SEQ ID NO 41
<211> LENGTH: 73
<212> TYPE: PRT
<213> ORGANISM: Benign prostatic hyperplasia virus

<400> SEQUENCE: 41

Leu Thr Ser Ser Tyr Ser Arg Pro Gln Pro Leu Gly Asp Val Pro Ala
1               5                   10                  15

Ala Ser Gly Ala Arg Phe Val Ala His Ser Val Ser Val Asn Leu Pro
                20                  25                  30

Glu Ser Asp Phe Leu Glu Leu Arg His Cys Thr Cys Leu Cys Trp Gly
            35                  40                  45

Thr Arg Asp Arg Asp Thr Ser Arg Pro Arg Leu Asp Phe Cys Phe Arg
        50                  55                  60

Phe Tyr Ala Glu Thr Ala Pro Arg Val
65                  70

<210> SEQ ID NO 42
<211> LENGTH: 73
<212> TYPE: PRT
<213> ORGANISM: Benign prostatic hyperplasia virus

<400> SEQUENCE: 42

Leu Thr Ser Ser Tyr Ser Arg Pro Gln Pro Trp Glu Thr Ser Gln Arg
1               5                   10                  15

His Arg Gly Pro Ser Leu Trp Pro Asn Leu Tyr Leu Arg Thr Arg Pro
                20                  25                  30

Val Ser Asp Ser Leu Glu Pro Leu Leu Pro Arg Asp Thr Trp Phe Cys
            35                  40                  45

Trp Ala Ala Arg Gly Arg Asn Ala Pro Pro Pro Ser Glu Phe Leu
        50                  55                  60

Leu Ser Val Phe Arg Arg Asn Arg Ala
65                  70

<210> SEQ ID NO 43
<211> LENGTH: 73
```

```
<212> TYPE: PRT
<213> ORGANISM: Benign prostatic hyperplasia virus

<400> SEQUENCE: 43

Leu Arg Ser Ser Tyr Ser Arg Pro Gln Pro Leu Gly Asp Val Pro Val
1               5                   10                  15

Ala Ser Gly Ala Arg Phe Val Val His Ser Val Ser Leu Asn Leu Pro
            20                  25                  30

Glu Ser Asp Phe Leu Glu Leu Arg His Cys Thr Trp Val Trp Trp Gly
        35                  40                  45

Thr Arg Asp Arg Asp Thr Ser Arg Pro Arg Leu Asp Phe Cys Phe Arg
    50                  55                  60

Leu Tyr Ala Glu Thr Ala Pro Arg Val
65                  70

<210> SEQ ID NO 44
<211> LENGTH: 73
<212> TYPE: PRT
<213> ORGANISM: Benign prostatic hyperplasia virus

<400> SEQUENCE: 44

Leu Thr Ser Ser Tyr Ser Arg Pro Gln Pro Leu Gly Asp Val Pro Ala
1               5                   10                  15

Ala Ser Gly Ala Arg Phe Val Ala His Ser Val Ser Val Asn Leu Pro
            20                  25                  30

Glu Ser Asp Phe Leu Glu Leu Arg His Cys Thr Trp Leu Cys Trp Gly
        35                  40                  45

Thr Arg Asp Arg Asp Thr Ser Arg Pro Arg Leu Asn Phe Cys Phe Arg
    50                  55                  60

Phe Tyr Ala Glu Thr Ala Pro Arg Val
65                  70

<210> SEQ ID NO 45
<211> LENGTH: 73
<212> TYPE: PRT
<213> ORGANISM: Benign prostatic hyperplasia virus

<400> SEQUENCE: 45

Leu Thr Ser Ser Tyr Ser Arg Pro Gln Pro Leu Gly Asp Val Pro Ala
1               5                   10                  15

Ala Ser Gly Ala Arg Phe Val Ala His Ser Val Ser Val Asn Leu Pro
            20                  25                  30

Glu Ser Asp Phe Leu Glu Leu Arg His Cys Thr Trp Leu Cys Trp Gly
        35                  40                  45

Ala Arg Asp Arg Asp Thr Ser Arg Pro Arg Leu Asp Phe Cys Phe Arg
    50                  55                  60

Phe Tyr Ala Glu Thr Ala Pro Arg Val
65                  70

<210> SEQ ID NO 46
<211> LENGTH: 75
<212> TYPE: PRT
<213> ORGANISM: Benign prostatic hyperplasia virus
<220> FEATURE:
<221> NAME/KEY: misc_feature
<222> LOCATION: (68)..(68)
<223> OTHER INFORMATION: Xaa can be any naturally occurring amino acid

<400> SEQUENCE: 46

Leu Thr Ser Ser Tyr Ser Arg Pro Gln Pro Trp Glu Thr Ser Gln Arg
```

```
                1               5                  10                 15
His Arg Gly Pro Ser Leu Trp Pro Asn Leu Tyr Leu Arg Thr Arg Pro
                20                  25                 30

Val Ser Asp Ser Leu Glu Pro Leu Pro Arg Asp Thr Trp Phe Cys
        35                  40                 45

Trp Ala Ala Arg Gly Arg Asn Ala Pro Leu Pro His Leu Asn Phe Cys
    50                  55                 60

Phe Arg Phe Xaa Ala Glu Thr Ala Pro Arg Val
65                  70                 75

<210> SEQ ID NO 47
<211> LENGTH: 75
<212> TYPE: PRT
<213> ORGANISM: Benign prostatic hyperplasia virus

<400> SEQUENCE: 47

Leu Thr Ser Ser Tyr Ser Arg Pro Gln Pro Trp Glu Thr Ser Gln Arg
1               5                  10                 15

His Arg Gly Pro Ser Leu Trp Pro Asn Leu Tyr Leu Arg Thr Arg Pro
                20                  25                 30

Val Ser Asp Ser Leu Glu Pro Leu Pro Arg Asp Thr Trp Phe Cys
        35                  40                 45

Trp Ala Ala Arg Gly Arg Asn Ala Pro Leu Pro His Leu Asn Phe Cys
    50                  55                 60

Phe Arg Phe Ser Ala Glu Thr Ala Pro Arg Val
65                  70                 75

<210> SEQ ID NO 48
<211> LENGTH: 76
<212> TYPE: PRT
<213> ORGANISM: Benign prostatic hyperplasia virus

<400> SEQUENCE: 48

Leu Thr Ser Ser Tyr Ser Arg Pro Gln Pro Trp Glu Thr Ser Gln Arg
1               5                  10                 15

Pro Arg Gly Pro Val Leu Trp Pro Ile Leu Tyr Gln Leu Thr Cys Pro
                20                  25                 30

Ser Arg Ile Phe Leu Glu Leu Leu His Cys Pro Arg Gly Thr Trp Leu
        35                  40                 45

Cys Arg Gly Thr Arg Gly Arg Asp Thr Ser Leu Pro Arg Leu Asn Phe
    50                  55                 60

Cys Phe Arg Phe Tyr Ala Glu Thr Ala Pro Arg Val
65                  70                 75

<210> SEQ ID NO 49
<211> LENGTH: 93
<212> TYPE: PRT
<213> ORGANISM: Benign prostatic hyperplasia virus

<400> SEQUENCE: 49

Leu Thr Ser Ser Tyr Ser Arg Pro Gln Pro Trp Glu Thr Ser Gln Arg
1               5                  10                 15

His Arg Gly Pro Ser Leu Trp Pro Asn Leu Tyr Leu Arg Thr Arg Pro
                20                  25                 30

Val Ser Asp Ser Leu Glu Pro Leu Pro Arg Asp Thr Trp Phe Cys
        35                  40                 45

Arg Ala Ala Arg Gly Arg Ser Ala Pro Pro Pro Ser Glu Phe Leu
    50                  55                 60
```

```
Leu Ser Val Phe Arg Arg Asn Arg Ala Ala Arg Leu Thr Ser Leu Gly
65                  70                  75                  80

Gly Ser Pro Gln Leu Arg Ala Glu Thr Ala Pro Arg Val
                85                  90
```

<210> SEQ ID NO 50
<211> LENGTH: 75
<212> TYPE: PRT
<213> ORGANISM: Benign prostatic hyperplasia virus

<400> SEQUENCE: 50

```
Leu Thr Ser Ser Tyr Ser Arg Pro Gln Pro Trp Glu Thr Ser Gln Arg
1               5                   10                  15

His Arg Gly Pro Ser Leu Arg Pro Asn Leu Tyr Leu Arg Thr Arg Pro
                20                  25                  30

Val Ser Asp Ser Leu Glu Pro Leu Pro Arg Asp Thr Trp Phe Cys
            35                  40                  45

Trp Ala Ala Arg Gly Arg Asn Ala Pro Leu Pro His Leu Asn Phe Cys
    50                  55                  60

Phe Arg Phe Ser Ala Glu Thr Ala Pro Arg Val
65                  70                  75
```

<210> SEQ ID NO 51
<211> LENGTH: 73
<212> TYPE: PRT
<213> ORGANISM: Benign prostatic hyperplasia virus
<220> FEATURE:
<221> NAME/KEY: misc_feature
<222> LOCATION: (65)..(65)
<223> OTHER INFORMATION: Xaa can be any naturally occurring amino acid

<400> SEQUENCE: 51

```
Leu Thr Ser Ser Tyr Ser Arg Pro Gln Pro Leu Gly Asp Val Pro Ala
1               5                   10                  15

Gly Ser Gly Ala Arg Phe Val Ala His Ser Val Ser Val Asn Leu Pro
                20                  25                  30

Glu Ser Asp Phe Leu Glu Leu Arg His Cys Thr Trp Leu Cys Trp Gly
            35                  40                  45

Thr Arg Asp Arg Asp Thr Ser Arg Pro Arg Leu Asn Phe Cys Phe Arg
    50                  55                  60

Xaa Tyr Ala Glu Thr Ala Pro Arg Val
65                  70
```

<210> SEQ ID NO 52
<211> LENGTH: 73
<212> TYPE: PRT
<213> ORGANISM: Benign prostatic hyperplasia virus

<400> SEQUENCE: 52

```
Leu Thr Ser Ser Tyr Ser Arg Pro Gln Pro Leu Gly Asp Val Pro Ala
1               5                   10                  15

Ala Ser Gly Ala Arg Phe Val Ala His Ser Val Ser Val Asn Leu Pro
                20                  25                  30

Glu Ser Asp Phe Leu Glu Leu Arg His Cys Thr Trp Leu Cys Trp Gly
            35                  40                  45

Thr Arg Asp Arg Asp Thr Ser Arg Pro Arg Leu Asp Phe Cys Phe Arg
    50                  55                  60

Phe Tyr Ala Glu Thr Ala Pro Arg Val
65                  70
```

<210> SEQ ID NO 53
<211> LENGTH: 73
<212> TYPE: PRT
<213> ORGANISM: Benign prostatic hyperplasia virus

<400> SEQUENCE: 53

Leu Thr Ser Ser Tyr Ser Arg Pro Gln Pro Leu Gly Asp Val Pro Ala
1               5                   10                  15

Ala Ser Gly Ala Arg Phe Val Ala His Ser Val Ser Val Asn Leu Pro
            20                  25                  30

Glu Ser Asp Phe Leu Glu Leu Arg His Cys Thr Trp Leu Cys Trp Gly
        35                  40                  45

Thr Arg Asp Arg Asp Thr Ser Arg Pro Arg Leu Asp Phe Cys Phe Arg
    50                  55                  60

Phe Tyr Ala Glu Thr Ala Pro Arg Val
65                  70

<210> SEQ ID NO 54
<211> LENGTH: 73
<212> TYPE: PRT
<213> ORGANISM: Benign prostatic hyperplasia virus

<400> SEQUENCE: 54

Leu Thr Ser Ser Tyr Ser Trp Pro Gln Pro Leu Gly Asp Val Pro Ala
1               5                   10                  15

Ala Ser Gly Ala Arg Phe Val Ala His Ser Val Ser Val Asn Leu Pro
            20                  25                  30

Glu Ser Asp Phe Leu Glu Leu Arg His Cys Thr Trp Leu Cys Trp Gly
        35                  40                  45

Thr Arg Asp Arg Asp Thr Ser Arg Pro Arg Leu Asp Phe Cys Phe Arg
    50                  55                  60

Phe Tyr Ala Glu Thr Ala Pro Arg Val
65                  70

<210> SEQ ID NO 55
<211> LENGTH: 326
<212> TYPE: PRT
<213> ORGANISM: Benign prostatic hyperplasia virus

<400> SEQUENCE: 55

Leu Asn Leu Thr Ser Pro Asp Lys Thr Gln Glu Cys Trp Leu Cys Leu
1               5                   10                  15

Val Ser Gly Pro Pro Tyr Tyr Glu Gly Val Ala Val Leu Gly Thr Tyr
            20                  25                  30

Ser Asn His Thr Ser Ala Pro Ala Asn Cys Ser Val Ala Ser Gln His
        35                  40                  45

Lys Leu Thr Leu Ser Glu Val Thr Gly Gln Gly Leu Cys Val Gly Ala
    50                  55                  60

Val Pro Lys Thr His Gln Ala Leu Cys Asn Thr Thr Gln Lys Thr Ser
65                  70                  75                  80

Asp Gly Ser Tyr Tyr Leu Ala Ala Pro Ala Gly Thr Ile Trp Ala Cys
                85                  90                  95

Asn Thr Gly Leu Thr Pro Cys Leu Ser Thr Thr Val Leu Asn Leu Thr
            100                 105                 110

Thr Asp Tyr Cys Val Leu Val Glu Leu Trp Pro Lys Val Thr Tyr His
        115                 120                 125

```
Ser Pro Gly Tyr Ala Tyr Gly Gln Phe Glu Arg Lys Thr Lys Tyr Lys
    130                 135                 140

Arg Glu Pro Val Ser Leu Thr Leu Ala Leu Leu Leu Gly Gly Leu Thr
145                 150                 155                 160

Met Gly Gly Ile Ala Ala Gly Val Gly Thr Gly Thr Thr Ala Leu Val
                165                 170                 175

Ala Thr Lys Gln Phe Glu Gln Leu Gln Ala Ala Ile His Thr Asp Leu
            180                 185                 190

Arg Ala Leu Glu Lys Ser Val Ser Ala Leu Glu Lys Ser Leu Thr Ser
        195                 200                 205

Leu Ser Glu Val Val Leu Gln Asn Arg Arg Gly Leu Asp Leu Leu Phe
    210                 215                 220

Leu Lys Glu Gly Gly Leu Cys Ala Ala Leu Lys Glu Glu Cys Cys Phe
225                 230                 235                 240

Tyr Ala Asp His Thr Gly Val Val Arg Asp Ser Met Ala Lys Leu Arg
                245                 250                 255

Glu Arg Leu Asn Gln Arg Gln Lys Leu Phe Glu Ser Gly Gln Gly Trp
            260                 265                 270

Phe Glu Gly Leu Phe Asn Arg Ser Pro Trp Phe Thr Thr Leu Ile Ser
        275                 280                 285

Thr Ile Met Gly Pro Leu Ile Ile Leu Leu Leu Ile Leu Leu Leu Gly
    290                 295                 300

Pro Cys Ile Leu Asn Arg Leu Val Gln Phe Val Lys Lys Glu Phe Arg
305                 310                 315                 320

Gly Gly Arg Pro Trp Phe
                325

<210> SEQ ID NO 56
<211> LENGTH: 318
<212> TYPE: PRT
<213> ORGANISM: Benign prostatic hyperplasia virus

<400> SEQUENCE: 56

Gly Thr Phe Ser His Pro Phe Ala Pro Ala Asn Cys Ser Gly Pro
1               5                   10                  15

Pro Gln Pro Lys Val Thr Leu Ser Glu Gly Thr Gly Pro Gly Phe Leu
            20                  25                  30

Arg Arg Ser Ser Pro Lys Pro His Gln Ala Leu Cys Asn Thr Thr
        35                  40                  45

Gln Lys Thr Ser Asp Gly Ser Tyr Tyr Leu Ala Ser Pro Ala Gly Thr
    50                  55                  60

Ile Trp Ala Cys Ser Thr Gly Leu Thr Pro Cys Leu Ser Thr Thr Val
65                  70                  75                  80

Leu Asn Leu Thr Thr Asp Tyr Cys Val Leu Val Glu Leu Trp Pro Lys
                85                  90                  95

Val Thr Tyr His Ser Pro Gly Tyr Val Tyr Gly Gln Phe Glu Lys Lys
            100                 105                 110

Thr Lys Tyr Lys Arg Glu Pro Val Ser Leu Thr Leu Ala Leu Leu Leu
        115                 120                 125

Gly Gly Leu Thr Met Gly Gly Ile Ala Ala Gly Val Gly Thr Gly Thr
    130                 135                 140

Thr Ala Leu Val Ala Thr Lys Gln Phe Glu Gln Leu Gln Ala Ala Ile
145                 150                 155                 160

His Thr Asp Leu Gly Ala Leu Glu Lys Ser Val Ser Ala Leu Glu Lys
                165                 170                 175
```

```
Ser Leu Thr Ser Leu Ser Glu Val Val Leu Gln Asn Arg Arg Gly Leu
            180                 185                 190

Asp Leu Leu Phe Leu Lys Glu Gly Leu Cys Ala Ala Leu Lys Glu
            195                 200                 205

Glu Cys Cys Phe Tyr Ala Asp His Thr Gly Val Val Arg Asp Ser Met
210                 215                 220

Ala Lys Leu Arg Glu Arg Leu Asn Gln Arg Gln Lys Leu Phe Glu Ser
225                 230                 235                 240

Gly Gln Gly Trp Ser Glu Gly Leu Phe Asn Arg Ser Pro Trp Phe Thr
                245                 250                 255

Thr Leu Ile Ser Thr Ile Met Gly Pro Leu Ile Ile Leu Leu Leu Ile
            260                 265                 270

Leu Leu Phe Gly Pro Cys Ile Leu Asn Arg Leu Val Gln Phe Val Lys
            275                 280                 285

Asp Arg Ile Ser Val Val Gln Ala Leu Ala Leu Thr Gln Gln Tyr His
            290                 295                 300

Gln Leu Lys Ser Ile Asp Pro Glu Glu Val Glu Ser Arg Glu
305                 310                 315

<210> SEQ ID NO 57
<211> LENGTH: 133
<212> TYPE: PRT
<213> ORGANISM: Benign prostatic hyperplasia virus

<400> SEQUENCE: 57

Gly Thr Met Thr Asp Thr Phe Pro Lys Leu Tyr Phe Asp Leu Cys Asp
1               5                   10                  15

Leu Val Gly Asp Asn Trp Asp Asp Pro Glu Ser Ser Ser Gly His Gly
            20                  25                  30

Cys Arg Ser Pro Gly Gly Arg Lys Arg Thr Arg Thr Phe Asp Phe Tyr
        35                  40                  45

Val Cys Pro Gly His Thr Val Leu Thr Gly Cys Gly Gly Pro Arg Glu
50                  55                  60

Gly Tyr Cys Gly Lys Trp Gly Cys Glu Thr Thr Gly Gln Ala Tyr Trp
65                  70                  75                  80

Lys Pro Ser Ser Ser Trp Asp Leu Ile Ser Leu Lys Arg Gly Asn Thr
                85                  90                  95

Pro Arg Ser Gln Gly Pro Cys Tyr Asp Ser Ser Val Val Ser Ser Ser
            100                 105                 110

Val Gln Gly Ala Thr Pro Gly Gly Arg Cys Asn Pro Leu Val Leu Glu
        115                 120                 125

Phe Thr Asp Ala Gly
    130

<210> SEQ ID NO 58
<211> LENGTH: 133
<212> TYPE: PRT
<213> ORGANISM: Benign prostatic hyperplasia virus

<400> SEQUENCE: 58

Gly Thr Met Thr Asp Thr Phe Pro Lys Leu Tyr Phe Asp Leu Cys Gly
1               5                   10                  15

Leu Val Gly Asp Asn Trp Asp Asp Pro Glu Ser Ser Ser Gly His Gly
            20                  25                  30

Cys Arg Ser Pro Gly Gly Arg Lys Gly Thr Arg Thr Phe Asp Phe Tyr
        35                  40                  45
```

```
Val Cys Pro Gly His Thr Val Leu Thr Gly Cys Gly Pro Arg Glu
    50                  55                  60

Gly Tyr Cys Gly Lys Trp Gly Cys Glu Thr Thr Gly Gln Ala Tyr Trp
 65                  70                  75                  80

Lys Pro Ser Ser Ser Trp Asp Leu Ile Ser Leu Lys Arg Gly Asn Thr
                85                  90                  95

Pro Arg Ser Gln Gly Pro Cys Tyr Asp Ser Ser Val Val Ser Ser Ser
                100                 105                 110

Val Gln Gly Ala Thr Pro Gly Gly Arg Cys Asn Pro Leu Val Leu Glu
            115                 120                 125

Phe Thr Asp Ala Gly
        130

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide primer - GagF

<400> SEQUENCE: 59
ccttgggagg gtctcctcag                                             20

<210> SEQ ID NO 60
<211> LENGTH: 21
<212> TYPE: DNA
<213> ORGANISM: Artificial Sequence
<220> FEATURE:
<223> OTHER INFORMATION: Synthetic oligonucleotide primer - GagR

<400> SEQUENCE: 60
cagacgcgcg gcgcggtttc g                                           21

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide primer - Env1F

<400> SEQUENCE: 61
cggccggaac agcatggaaa                                             20

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide primer - Env1R

<400> SEQUENCE: 62
ccggcgggag aggccaaata                                             20

<210> SEQ ID NO 63
<211> LENGTH: 23
<212> TYPE: DNA
<213> ORGANISM: Artificial Sequence
<220> FEATURE:
<223> OTHER INFORMATION: Synthetic oligonucleotide primer - Env2F

<400> SEQUENCE: 63
cctcaacctc accagtcccg aca                                         23
```

```
<210> SEQ ID NO 64
<211> LENGTH: 23
<212> TYPE: DNA
<213> ORGANISM: Artificial Sequence
<220> FEATURE:
<223> OTHER INFORMATION: Synthetic oligonucleotide primer - Env2R

<400> SEQUENCE: 64
ccatgccttg caaaatggcg tta                                              23

<210> SEQ ID NO 65
<211> LENGTH: 22
<212> TYPE: DNA
<213> ORGANISM: Artificial Sequence
<220> FEATURE:
<223> OTHER INFORMATION: Synthetic oligonucleotide primer - VariableF

<400> SEQUENCE: 65
gggacgatga cagacactttt cc                                              22

<210> SEQ ID NO 66
<211> LENGTH: 24
<212> TYPE: DNA
<213> ORGANISM: Artificial Sequence
<220> FEATURE:
<223> OTHER INFORMATION: Synthetic oligonucleotide primer - VariableR

<400> SEQUENCE: 66
ttacccgcgt cagtgaattc tagg                                             24

<210> SEQ ID NO 67
<211> LENGTH: 21
<212> TYPE: DNA
<213> ORGANISM: Artificial Sequence
<220> FEATURE:
<223> OTHER INFORMATION: Synthetic oligonucleotide primer - AREF

<400> SEQUENCE: 67
cgccattttg caaggcatgg a                                                21

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide primer - ARER

<400> SEQUENCE: 68
gggagcaaaa agcgcgggta                                                  20

<210> SEQ ID NO 69
<211> LENGTH: 21
<212> TYPE: DNA
<213> ORGANISM: Artificial Sequence
<220> FEATURE:
<223> OTHER INFORMATION: Synthetic oligonucleotide primer - controlF

<400> SEQUENCE: 69
caggcatgtg ctactgcatc c                                                21

<210> SEQ ID NO 70
<211> LENGTH: 23
<212> TYPE: DNA
<213> ORGANISM: Artificial Sequence
<220> FEATURE:
<223> OTHER INFORMATION: Synthetic oligonucleotide primer - controlR
```

<400> SEQUENCE: 70
tcctcattga cagaattgca cca                                                23

<210> SEQ ID NO 71
<211> LENGTH: 19
<212> TYPE: DNA
<213> ORGANISM: Artificial Sequence
<220> FEATURE:
<223> OTHER INFORMATION: Synthetic oligonuceotide primer - BVF

<400> SEQUENCE: 71
ttgtggccca wtctgtatc                                                     19

<210> SEQ ID NO 72
<211> LENGTH: 19
<212> TYPE: DNA
<213> ORGANISM: Artificial Sequence
<220> FEATURE:
<223> OTHER INFORMATION: Synthetic oligonucleotide primer - BVR

<400> SEQUENCE: 72
accgaaagca aaaattcag                                                     19

<210> SEQ ID NO 73
<211> LENGTH: 22
<212> TYPE: DNA
<213> ORGANISM: Artificial Sequence
<220> FEATURE:
<223> OTHER INFORMATION: Synthetic oligonucleotide probe - BV1

<400> SEQUENCE: 73
tccgccactg tacgtggctt tg                                                 22

<210> SEQ ID NO 74
<211> LENGTH: 25
<212> TYPE: DNA
<213> ORGANISM: Artificial Sequence
<220> FEATURE:
<223> OTHER INFORMATION: Synthetic oligonucleotide probe - BV2

<400> SEQUENCE: 74 cctctcctttt gaccgaggga tacgt                                             25

<210> SEQ ID NO 75
<211> LENGTH: 21
<212> TYPE: DNA
<213> ORGANISM: Artificial Sequence
<220> FEATURE:
<223> OTHER INFORMATION: Synthetic oligonucleotide primer - RNasePF

<400> SEQUENCE: 75
caggttaact acagctccca g                                                  21

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide primer - RNasePR

<400> SEQUENCE: 76
gtccaaatct gcaaacaccg                                                    20

<210> SEQ ID NO 77

```
<211> LENGTH: 21
<212> TYPE: DNA
<213> ORGANISM: Artificial Sequence
<220> FEATURE:
<223> OTHER INFORMATION: Synthetic oligonucleotide probe - RNaseP

<400> SEQUENCE: 77
tgaagtccca tgaccgtccg c                                              21

<210> SEQ ID NO 78
<211> LENGTH: 21
<212> TYPE: DNA
<213> ORGANISM: Artificial Sequence
<220> FEATURE:
<223> OTHER INFORMATION: Synthetic oligonucleotide primer - BPHV methF

<400> SEQUENCE: 78
agggattatc gatttatcgt c                                              21

<210> SEQ ID NO 79
<211> LENGTH: 18
<212> TYPE: DNA
<213> ORGANISM: Artificial Sequence
<220> FEATURE:
<223> OTHER INFORMATION: Synthetic oligonucleotide primer - BPHV methR

<400> SEQUENCE: 79
aattcaaacg caaacgcg                                                  18

<210> SEQ ID NO 80
<211> LENGTH: 8185
<212> TYPE: DNA
<213> ORGANISM: Xenotropic murine leukemia virus-related virus

<400> SEQUENCE: 80
gcgccagtca tccgatagac tgagtcgccc gggtacccgt gttcccaata aagccttttg      60
ctgtttgcat ccgaagcgtg gcctcgctgt tccttgggag ggtctcctca gagtgattga     120
ctacccagct cgggggtctt tcatttgggg gctcgtccgg gattcggaga ccccgccca     180 ggaccaccg acccaccgtc gggaggtaag ccggccggcg atcgttttgt ctttgtctct     240
gtctttgtgc gtgtgtgtgt gtgccggcat ctaatcctcg cgcctgcgtc tgaatctgta     300
ctagttagct aactagatct gtatctggcg gttccgcgga agaactgacg agttcgtatt     360
cccggccgca gccctgggag acgtcccagc ggcctcgggg gccgtttttg tggcccattc     420
tgtatcagtt aacctacccg agtcggactt tttggagtgg ctttgttggg ggacgagaga     480
cagagacact tcccgccccc gtctgaattt ttgctttcgg ttttacgccg aaaccgcgcc     540
gcgcgtctga tttgttttgt tgttcttctg ttccttcgtta gttttcttct gtctttaagt     600
gttctcgaga tcatgggaca gaccgtaact accccctctga gtctaacctt gcagcactgg     660
ggagatgtcc agcgcattgc atccaaccag tctgtggatg tcaagaagag gcgctgggtt     720
accttctgtt ccgccaatg gccaactttc aatgtaggat ggcctcagga tggtactttt     780
aatttaggtg ttatctctca ggtcaagtct agagtgtttt gtcctggtcc ccacggacac     840
ccggatcagg tccatatat cgtcacctgg gaggcacttg cctatgaccc ccctccgtgg     900
gtcaaaccgt ttgtctctcc taaacccccct ccttaccga cagctcccgt cctccgccc     960 ggtccttctg cgcaacctcc gtcccgatct gccctttacc ctgcccttac cccctctata    1020
aagtccaaac tcctaagcc ccaggttctc cctgatagcg gcggacctct cattgacctt    1080
ctcacagagg atcccccgcc gtacgagca caaccttcct cctctgccag ggagaacaat    1140
```

```
gaagaagagg cggccaccac ctccgaggtt tccccccctt ctcccatggt gtctcgactg    1200
cggggaagga gagaccctcc cgcagcggac tccaccacct cccaggcatt cccactccgc    1260
atggggggag atggccagct tcagtactgg ccgttttcct cctctgattt atataattgg    1320
aaaaataata acccttcctt ttctgaagat ccaggtaaat tgacggcctt gattgagtcc    1380
gtcctcatca cccaccagcc cacctgggac gactgtcagc agttgttggg gaccctgctg    1440 accgagaag aaaagcagcg ggtgctccta gaggctagaa aggcagtccg gggcaatgat    1500
ggacgcccca ctcagttgcc taatgaagtc aatgctgctt ttccccttga gcgccccgat    1560
tgggattaca ccactacaga aggtaggaac cacctagtcc tctaccgcca gttgctctta    1620
gcgggtctcc aaaacgcggg caggagcccc accaatttgg ccaaggtaaa agggataacc    1680
cagggaccta atgagtctcc ctcagccttt ttagagagac tcaaggaggc ctatcgcagg    1740
tacactcctt atgaccctga ggacccaggg caagaaacca atgtgtccat gtcattcatc    1800
tggcagtctg ccccggatat cggacgaaag ttagagcggt tagaagattt aaagagcaag    1860
accttaggag acttagtgag ggaagctgaa aagatctttta ataagcgaga aaccccggaa    1920
gaaagagagg aacgtatcag gagagaaata gaggaaaaag aagaacgccg tagggcagag    1980
gatgagcaga gagagagaga aagggaccgc agaagacata gagagatgag caagctcttg    2040
gccactgtag ttattggtca gagacaggat agacaggggg gagagcggag gaggccccaa    2100
cttgataagg accaatgcgc ctactgcaaa gaaaagggac actgggctaa ggactgccca    2160
aagaagccac gagggccccg aggaccgagg cccccagacct ccctcctgac cttaggtgac    2220
tagggaggtc agggtcagga gcccccccct gaacccagga taaccctcaa agtcgggggg    2280
caacccgtca ccttcctggt agatactggg gcccaacact ccgtgctgac ccaaaatcct    2340
ggacccctaa gtgacaagtc tgcctgggtc caagggctaa ctggaggaaa gcggtatcgc    2400
tggaccacgg atcgcaaagt acatctggct accggtaagg tcacccactc tttcctccat    2460
gtaccagact gcccctatcc tctgctagga agagacttgc tgactaaact aaaagcccaa    2520
atccactttg agggatcagg agctcaggtt gtgggaccga tgggacagcc cctgcaagtg    2580
ctgacagtaa acatagaaga tgagtattgg ctacatgata ccaggaaaga gccagatgtt    2640
cctctagggt ccacatggct ttctgatttc cttcaggcct gggcggaaac cggggcatg    2700 ggactggcag ttcgccaagc tcctctgatc atacctctga aggcaacctc tacccccgtg    2760
tccataaaac aataccccat gtcacaagaa gccagactgg ggatcaagcc ccacatacag    2820
aggctgttgg accagggaat actggtaccc tgccagtccc cctggaacac gcccctgcta    2880
cccgttaaga aaccagggac taatgattat aggcctgtcc aggatctgag agaagtcaac    2940
aagcgggtgg aagacatcca ccccaccgtg cccaaccctt acaacctctt gagcgggctc    3000
ccaccgtccc accagtggta cactgtgctt gatttaaagg atgcctttt ctgcctgaga    3060 ctccacccca ccagtcagcc tctcttcgcc tttgagtgga gagatccaga gatgggaatc    3120
tcaggacaac tgacctggac cagactccca cagggtttca aaacagtcc caccctgttt    3180 gatgaggcac tgcacagaga cctagcagat ttcggatcc agcacccaga cttgatcctg    3240
ctacagtacg tggatgactt actgctggcc gccacttctg agcaagactg ccaacgaggt    3300
actcgggccc tattacaaac cctagggaac ctcgggtatc gggcctcggc caagaaagcc    3360
caaatttgcc agaaacaggt caagtatctg gggtatctcc taaaagaggg acagagatgc    3420
ctgactgagg ccagaaaaga gactgtgatg gggcagccca ctccgaagac ccctcgacaa    3480
```

```
ctaagggagt tcctagggac ggcaggcttc tgtcgcctct ggatccctgg gtttgcagaa    3540
atggcagccc ccttgtaccc tcttaccaaa acggggactc tgtttaattg gggcccagac    3600
cagcaaaagg cctatcaaga aatcaaacag gctcttctaa ctgccccgc cctgggattg     3660 ccagatttga ctaagccctt tgaactcttt gtcgacgaga agcagggcta cgccaaaggc    3720
gtcctaacgc aaaaactggg accttggcgt cggcctgtgg cctacctgtc caaaaagcta    3780
gacccagtgg cagctgggtg gccccttgc ctacggatgg tagcagccat tgccgttctg     3840
acaaaaaatg caggcaagct aactatggga cagccgctag tcattctggc ccccatgcg    3900 gtagaagcac tggtcaaaca ccccctgac cgttggctat ccaatgcccg catgacccac    3960
tatcaggcaa tgctcctgga tacagaccgg gttcagttcg gaccggtggt ggccctcaac    4020
ccggccaccc tgctcccct accggaaaag gaagccccc atgactgcct cgagatcttg      4080
gctgagacgc acggaaccag accggacctc acggaccagc ccatcccaga cgctgattac    4140
acttggtaca cagatggaag cagcttccta caagaaggac aacggagagc tggagcagcg    4200
gtgactactg agaccgaggt aatctgggcg agggctctgc cggctggaac atccgcccaa    4260
cgagccgaac tgatagcact cacccaagcc ttaaagatgg cagaaggtaa gaagctaaat    4320
gtttacactg atagccgcta tgccttcgcc acggcccatg tccatggaga atatatagg     4380 aggcgagggt tgctgacctc agaaggcaga gaaattaaaa acaagaacga gatcttggcc    4440
ttgctaaaag ctctctttct gcccaaacga cttagtataa ttcactgtcc aggacatcaa    4500
aaaggaaaca gtgctgaggc cagaggcaac cgtatggcag atcaagcagc ccgagaggca    4560
gccatgaagg cagttctaga aacctctaca ctcctcatag aggactcaac cccgtatacg    4620 cctcccatt tccattacac cgaaacagat ctcaaaagac tacgggaact gggagccacc    4680
tacaatcaga caaaggata ttgggtccta caaggcaaac ctgtgatgcc cgatcagtcc      4740
gtgtttgaac tgttagactc cctacacaga ctcacccatc tgagccctca aaagatgaag    4800
gcactcctcg acagagaaga aagcccctac tacatgttaa accgggacag aactatccag    4860
tatgtgactg agacctgcac cgcctgtgcc caagtaaatg ccagcaaagc caaaattggg    4920
gcaggggtgc gagtacgcgg acatcggcca ggcacccatt gggaagttga tttcacggaa    4980
gtaaagccag gactgtatgg gtacaagtac ctcctagtgt ttgtagacac cttctctggc    5040
tgggtagagg cattcccgac caagcgggaa actgccaagg tcgtgtccaa aaagctgtta    5100
gaagacattt ttccgagatt tggaatgccg caggtattgg gatctgataa cgggcctgcc    5160
ttcgcctccc aggtaagtca gtcagtggcc gatttactgg ggatcgattg gaagttacat    5220
tgtgcttata gaccccagag ttcaggacag gtagaaagaa tgaatagaac aattaaggag    5280
actttgacca aattaacgct tgcatctggc actagagact gggtactcct actcccctta    5340
gccctctacc gagcccggaa tactccgggc ccccacggac tgactccgta tgaaattctg    5400 tatgggcac cccgccct tgtcaatttt catgatcctg aaatgtcaaa gttaactaat        5460
agtccctctc tccaagctca cttacaggcc ctccaagcag tacaacaaga ggtctggaag    5520
ccgctggccg ctgcttatca ggaccagcta gatcagccag tgataccaca cccttccgt     5580 gtcggtgacg ccgtgtgggt acgcggcac cagactaaga acttagaacc tcgctggaaa    5640
ggaccctaca ccgtcctgct gacaacccc accgctctca agtagacgg catctctgcg      5700 tggatacacg ccgctcacgt aaaggcggcg acaactcctc cggccggaac agcatggaaa    5760
gtccagcgtt ctcaaaaccc cttaaagata agattaaccc gtgggccccc tgataatta     5820 tggggatctt ggtgagggca ggagcctcag tacaacgtga cagccctcac caggtcttta    5880
```

```
atgtcacttg gaaaattacc aacctaatga caggacaaac agctaatgct acctccctcc   5940
tggggacgat gacagacact ttccctaaac tatattttga cttgtgtgat ttagttggag   6000
acaactggga tgacccggaa cccgatattg gagatggttg ccgctctccc ggggaagaa    6060
aaaggacaag actatatgat ttctatgttt gccccggtca tactgtatta cagggtgtg    6120
gagggccgag agagggctac tgtggcaaat ggggatgtga ccactggaca ggcatact     6180
ggaagccatc atcatcatgg acctaatttt cccttaagcg aggaaacact cctaagggtc   6240
agggcccctg ttttgattcc tcagtgggct ccggtagcat ccagggtgcc acccggggg    6300
gtcgatgcaa cccctagtc ctagaattca ctgacgcggg taaagggcc agctgggatg     6360
cccccaaaac atggggacta agactgtatc gatccactgg ggccgacccg gtgaccctgt   6420
tctctctgac ccgccaggtc ctcaatgtag ggccccgcgt ccccattggg cctaatcccg   6480
tgatcactga acagctaccc ccctcccaac ccgtgcagat catgctcccc aggactcctc   6540
gtcctcctcc ttcaggcgcg gcctctatgg tgcctgggc tcccccgcct tctcaacaac    6600
ctgggacggg agacaggctg ctaaacctgg tagaaggagc ctacctagcc ctcaacctca   6660
ccagtcccga caaacccaa gagtgctggc tgtgtctagt atcgggaccc ccctactacg     6720
aaggggtggc cgtcctaggt acttactcca accatacctc tgccccggct aactgctccg   6780
tgacctccca acacaagctg accctgtccg aagtgaccgg gcaggactc tgcataggag     6840
cagttcccaa aacccatcag gccctgtgta ataccaccca gaagacgagc gacgggtcct   6900
actatttggc ctctcccgcc gggaccattt gggcttgcag caccgggctc actccctgtc   6960
tatctactac tgtgcttaac ttaaccactg attactgtgt cctggttgaa ctctggccaa   7020
aggtaaccta ccactcccct aattatgttt atggccagtt tgaaaagaaa actaaatata   7080
aaagagagcc ggtgtcatta actctggccc tgctgttggg aggacttact atgggcggca   7140
tagctgcagg agttggaaca gggactacag ccctagtggc caccaaacaa ttcgagcagc   7200
tccaggcagc catacataca gaccttgggg ccttagaaaa atcagtcagt gccctagaaa   7260
agtctctgac ctcgttgtct gaggtggtcc tacagaaccg gagggatta gatctactgt    7320
tcctaaaaga aggaggatta tgtgctgccc taaaagaaga atgctgtttt tacgcggacc   7380
acactggcgt agtaagagat agcatggcaa agctaagaga aggttaaac cagagacaaa     7440
aattgttcga atcaggacaa gggtggtttg agggactgtt taacaggtcc ccatggttca   7500
cgaccctgat atccaccatt atgggccctc tgatagtact tttattaatc ctactcttcg   7560
gaccctgtat tctcaaccgc ttggtccagt ttgtaaaaga cagaatttcg gtagtgcagg   7620
ccctggttct gacccaacag tatcaccaac tcaaatcaat agatccagaa gaagtggaat   7680
cacgtgaata aaagatttta ttcagtttcc agaagagggg gggaatgaaa gaccccacca   7740
taaggcttag cacgctagct acagtaacgc cattttgcaa ggcatggaaa agtaccagag   7800
ctgagttctc aaaagttaca aggaagttta attaaagaat aaggctgaat aacactggga   7860
cagggccaa acaggatatc tgtagtcagg cacctgggcc ccggctcagg gccaagaaca    7920
gatggtcctc agataaagcg aaactaacaa cagtttctgg aaagtcccac ctcagtttca   7980
agttccccaa aagaccggga aatacccaa gccttattta aactaaccaa tcagctcgct    8040
tctcgcttct gtaccgcgc ttttgctcc ccagtcctag ccctataaaa aagggtaag     8100
aactccacac tcgcgcgcc agtcatccga tagactgagt cgcccgggta cccgtgttcc    8160
caataaagcc ttttgctgtt tgcaa                                        8185
```

<210> SEQ ID NO 81
<211> LENGTH: 464
<212> TYPE: DNA
<213> ORGANISM: Benign prostatic hyperplasia virus

<400> SEQUENCE: 81

| | | | | | |
|---|---|---|---|---|---|
| ccttgggagg | gtctcctcag | attgattgac | tacccacgtc | gggggtcttt | catttggagg | 60 |
| ttccaccgag | atttggagac | ccctgcccag | ggaccaccga | cccccgccg | ggaggtaagc | 120 |
| tggccagcgg | tcgtttcgtg | tctgtctctg | tcttcgtgcg | tgtttgtgcc | ggcatccaat | 180 |
| gtttgcgcct | gcgtctgtac | tagttagcta | actagatctg | tatctggcgg | ttccgcggaa | 240 |
| gaactgacga | gttcgtattc | ccggccgcag | ccctgggag | acgtcccagc | ggcctcgggg | 300 |
| gcccgttttg | tggcccattc | tgtatcagtt | aacctacccg | agtcggactt | tttgagctc | 360 |
| cgccactgta | cgtggctttg | ttgggggacg | agagacagag | acacttcccg | cccccgtctg | 420 |
| gattttgct | ttcggtttta | cgccgaaacc | gcgccgcgcg | tctg | | 464 |

<210> SEQ ID NO 82
<211> LENGTH: 462
<212> TYPE: DNA
<213> ORGANISM: Benign prostatic hyperplasia virus

<400> SEQUENCE: 82

| | | | | | |
|---|---|---|---|---|---|
| ttgggagggt | ctcctcagat | tgattgacta | cccacgtcgg | gggtctttca | tttggaggtt | 60 |
| ccaccgagat | ttggagaccc | ctgcccaggg | accaccgacc | cccgccggg | aggtaagctg | 120 |
| gccagcggtc | gtttcgtgtc | tgtctctgtc | ttcgtgcgtg | tttgtgccgg | catccaatgt | 180 |
| ttgcgcctgc | gtctgtacta | gttagctaac | tagatctgta | tctggcggtt | ccgcggaaga | 240 |
| actgacgagt | tcgtattccc | ggccgcagcc | ctgggagac | gtcccagcgg | cctcgggggc | 300 |
| ccgttttgtg | gcccattctg | tatcagttaa | cctacccgag | tcggactttt | tggagctccg | 360 |
| ccactgtacg | tggctttgtt | ggggacgag | agacagagac | ttcccgcc | ccgtctgga | 420 |
| tttttgcttt | cggttttacg | ccgaaaccgc | gccgcgcgtc | tg | | 462 |

<210> SEQ ID NO 83
<211> LENGTH: 464
<212> TYPE: DNA
<213> ORGANISM: Benign prostatic hyperplasia virus

<400> SEQUENCE: 83

| | | | | | |
|---|---|---|---|---|---|
| ccttgggagg | gtctcctcag | attgattgac | tacccacgtc | gggggtcttt | catttggagg | 60 |
| ttccaccgag | atttggagac | ccctgcccag | ggaccaccga | ccccccgccg | ggaggtaagc | 120 |
| tggccagcgg | tcgtttcgtg | tctgtctctg | tcttcgtgcg | tgtttgtgcc | ggcatccaat | 180 |
| gtttgcgcct | gcgtctgtac | tagttagcta | actagatctg | tatctggcgg | ttccgcggaa | 240 |
| gaactgacga | gttcgtattc | ccggccgcag | ccctgggag | acgtcccagc | ggcctcgggg | 300 |
| gcccgttttg | tggcccattc | tgtatcagtt | aacctacccg | agtcggactt | tttgagctc | 360 |
| cgccactgta | cgtggctttg | ttgggggacg | agagacagag | acacttcccg | cccccgtctg | 420 |
| gattttgct | ttcggtttta | cgccgaaacc | gcgccgcgcg | tctg | | 464 |

<210> SEQ ID NO 84
<211> LENGTH: 465
<212> TYPE: DNA
<213> ORGANISM: Benign prostatic hyperplasia virus

<400> SEQUENCE: 84

```
ccttgggagg gtctcctcag attgattgac tacccacgtc gggggtattt catttggagg      60
ttccaccgag atttggagac ccctgcccag ggaccaccga ccccccgtcg ggaggtaagc     120
tggccagcgg tcgtttcgtg tctgtctctg tcttcgtgcg tgtttgtgcc ggcatccaat     180
gtttgcgcct gcgtctgtac tagttacgct aactagatct gtatctggag gatccgcgga     240
agaactgagg agttcgtatt cccggccgca gcccctggga gacgtcccag tggcctcggg     300
ggcccggttt gtggtccatt ctgtatcact gaacctaccc gagtctgact ttttggagct     360
ccgccactgt acgtgggttt ggtggggac gagagacaga gacacttccc gcccccgtct      420 ggattttgc tttcggcttt acgccgaaac cgcgccgcgc gtctg                      465
```

<210> SEQ ID NO 85
<211> LENGTH: 462
<212> TYPE: DNA
<213> ORGANISM: Benign prostatic hyperplasia virus

<400> SEQUENCE: 85

```
cttgggaggg ctcctcagat tgattgacta cccacgtcgg ggtctttca tttgaggtt       60 ccaccgagat ttgagaccc ctgcccaggg accaccgacc cccgccggg aggtaagctg      120 gccagcggtc gtttcgtgtc tgtctctgtc ttcgtgcgtg tttgtgccgg catccaatgt    180
ttgcgcctgc gtctgtacta gttagctaac tagatctgta tctggcggtt ccgcggaaga    240
actgacgagt tcgtattccc ggccgcagcc ctgggagac gtcccagcgg cctcgggggc      300
ccgttttgtg gcccattctg tatcagttaa cctacccgag tcggactttt tggagctccg    360
ccactgtacg tggctttgtt ggggacgag agacagagac acttcccgcc cccgtctgga     420
tttttgcttt cggttttacg ccgaaaccgc gccgcgcgtc tg                       462
```

<210> SEQ ID NO 86
<211> LENGTH: 464
<212> TYPE: DNA
<213> ORGANISM: Benign prostatic hyperplasia virus

<400> SEQUENCE: 86

```
ccttgggagg gtctcctcag attgattgac tacccacgtc ggggtctttc atttggagg      60 ttccaccgag atttggagac ccctgcccag ggaccaccga ccccccgccg ggaggtaagc    120
tggccagcgg tcgtttcgtg tctgtctctg tcttcgtgcg tgtttgtgcc ggcatccaat    180
gtttgcgcct gcgtctgtac tagttagcta actagatctg tatctggcgg ttccgcggaa    240
gaactgacga gttcgtattc ccggccgcag cccctgggaa cgtcccagc ggcctcgggg     300 gcccgttttg tggcccattc tgtatcagtt aacctacccg agtcggactt tttggagctc    360
cgccactgta cgtggctttg ttggggacg agagacagag acacttcccg ccccgtctg      420 gattttgct ttcggtttta cgccgaaacc gcgccgcgcg tctg                      464
```

<210> SEQ ID NO 87
<211> LENGTH: 464
<212> TYPE: DNA
<213> ORGANISM: Benign prostatic hyperplasia virus

<400> SEQUENCE: 87

```
ccttgggagg gtctcctcag attgattgac tacccacgtc ggggtctttc atttggagg      60 ttccaccgag atttggagac ccctgcccag ggaccaccga ccccccgccg ggaggtaagc    120
tggccagcgg tcgtttcgtg tctgtctctg tcttcgtgcg tgtttgtgcc ggcatccaat    180
```

```
gtttgcgcct gcgtctgtac tagttagcta actagatctg tatctggcgg ttccgcggaa      240
gaactgacga gttcgtattc ccggccgcag cccctgggag acgtcccagc ggcctcgggg      300
gcccgttttg tggcccattc tgtatcagtt aacctacccg agtcggactt tttggagctc      360
cgccactgta cgtggctttg ttggggggacg agagacagag acacttcccg ccccgtctg       420 gattttgct ttcggtttta cgccgaaacc gcgccgcgcg tctg                        464

<210> SEQ ID NO 88
<211> LENGTH: 464
<212> TYPE: DNA
<213> ORGANISM: Benign prostatic hyperplasia virus

<400> SEQUENCE: 88
ccttgggagg gtctcctcag attgattgac tacccacgtc gggggtcttt catttggagg      60
ttccaccgag atttggagac ccctgcccag ggaccaccga ccccccgccg ggaggtaagc      120
tggccagcgg tcgtttcgtg tctgtctctg tcttcgtgcg tgtttgtgcc ggcatccaat      180
gtttgcgcct gcgtctgtac tagttagcta actagatctg tatctggcgg ttccgcggaa      240
gaactgacga gttcgtattc ccggccgcag cccctgggag acgtcccagc ggcctcgggg      300
gcccgttttg tggcccattc tgtatcagtt aacctacccg agtcggactt tttggagctc      360
cgccactgta cgtggctttg ttggggggcg agagacagag acacttcccg ccccgtctg       420 gattttgct ttcggtttta cgccgaaacc gcgccgcgcg tctg                        464

<210> SEQ ID NO 89
<211> LENGTH: 463
<212> TYPE: DNA
<213> ORGANISM: Benign prostatic hyperplasia virus

<400> SEQUENCE: 89
ccttgggagg gtctcctcag attgattgac tacccacgtc gggggtcttt catttggagg      60
ttccaccgag atttggagac ccctgcccag ggaccaccga ccccccgccg ggaggtaagc      120
tggccagcgg tcgtttcgtg tctgtctctg tcttcgtgcg tgtttgtgcc ggcatccaat      180
gtttgcgcct gcgtctgtac tagttagcta actagatctg tatctggcgg ttccacggaa      240
gaactgacga gttcgtactc ccggccgcag cccctgggag acgtcccagc ggcctcgggg      300
gcccgttttg tggcccattc tgtagcagtt aacctacccg agtcggactt tttggagctc      360
cgccactgta cgtggctttg ttggggacg agagacagag acacttcccg ccccgtctg        420 aattttgctt tcggttttac gccgaaaccg cgccgcgcgt ctg                        463

<210> SEQ ID NO 90
<211> LENGTH: 465
<212> TYPE: DNA
<213> ORGANISM: Benign prostatic hyperplasia virus

<400> SEQUENCE: 90
ccttgggagg gtctcctcag attgattgac tacccacgtc gggggtcttt catttggagg      60
ttccaccgag atttggagac ccctgcccag ggaccaccga cccccccgcc gggaggtaag      120
ctggccagcg tcgtttcgt gtctgtctct gtcttcgtgc gtgtttgtgc cggcatccaa      180
tgtttgcgcc tgcgtctgta ctagttagct aactagatct gtatctggcg gttccgcgga      240
agaactgacg agttcgtatt cccggccgca gcccctggga cgtcccag cggcctcggg      300 ggcccgtttt gtggcccatt ctgtatcagt taacctaccc gagtcggact ttttggagct      360
ccgccactgt acgtggcttt gttggggac gagagacaga gacacttccc gccccgtct       420
```

```
gaattttgc tttcggtttt acgccgaaac cgcgccgcgc gtctg            465
```

<210> SEQ ID NO 91
<211> LENGTH: 469
<212> TYPE: DNA
<213> ORGANISM: Benign prostatic hyperplasia virus

<400> SEQUENCE: 91

```
ccttgggagg gtctcctcag attgattgac tacccacgtc ggggggtctttt catttggagg    60
ttccactgag atttggagac ccctgcccag ggaccaccga ccccccgccg ggaggtaagc   120
tggccagcgg tcgtttcgtg tctgtctctg tcttcgtgcg tgtttgtgcc ggcatccaat   180
gtttgcgcct gcgtctgtac tagttagcta actagatctg tatctggcgg ttccgcggaa   240
gaactgacga gttcgtattc ccggccgcag cccctgggag acgtcccagc ggcctcgggg   300
gcccgttttg tggcccattc tgtatcagtt aacctacccg agtcggactt tttggagctc   360
cgccactgta cgtggctttg ttggggggacg agagacagag acacttcccg ccccccgtctg   420
aattttttgct ttcggtttta cgccgaaacc gcgccgcgcg tctgaatcg            469
```

<210> SEQ ID NO 92
<211> LENGTH: 464
<212> TYPE: DNA
<213> ORGANISM: Benign prostatic hyperplasia virus

<400> SEQUENCE: 92

```
ccttgggagg gtctcctcag attgattgac tacccacgtc ggggggtctttt catttggagg    60
ttccactgag atttggagac ccctgcccag ggaccaccga ccccccgccg ggaggtaagc   120
tggccagcgg tcgtttcgtg tctgtctctg tcttcgtgcg tgtttgtgcc ggcatccaat   180
gtttgcgcct gcgtctgtac tagttagcta actagatctg tatctggcgg ttccgcggaa   240
gaactgacga gttcgtattc ccggccgcag cccctgggag acgtcccagc ggcctcgggg   300
gcccgttttg tggcccattc tgtatcagtt aacctacccg agtcggactt tttggagctc   360
cgccactgta cgtggctttg ttggggggacg agagacagag acacttcccg ccccccgtctg   420
aattttttgct ttcggtttta cgccgaaacc gcgccgcgcg tctg                     464
```

<210> SEQ ID NO 93
<211> LENGTH: 464
<212> TYPE: DNA
<213> ORGANISM: Benign prostatic hyperplasia virus

<400> SEQUENCE: 93

```
ccttgggagg gtctcctcag attgattgac tacccacgtc ggggggtctttt catttggagg    60
ttccactgag atttggagac ccctgcccag ggaccaccga ccccccgccg ggaggtaagc   120
tggccagcgg tcgtttcgtg tctgtctctg tcttcgtgcg tgtttgtgcc ggcatccaat   180
gtttgcgcct gcgtctgtac tagttagcta actagatctg tatctggcgg ttccgcggaa   240
gaactgacga gttcgtattc ccggccgcag cccctgggag acgtcccagc ggcctcgggg   300
gcccgttttg tggcccattc tgtatcagtt aacctacccg agtcggactt tttggagctc   360
cgccactgta cgtggctttg ttggggggacg agagacagag acacttcccg ccccccgtctg   420
aattttttgct ttcggtttta cgccgaaacc gcgccgcgcg tctg                     464
```

<210> SEQ ID NO 94
<211> LENGTH: 464
<212> TYPE: DNA

<213> ORGANISM: Benign prostatic hyperplasia virus

<400> SEQUENCE: 94
ccttgggagg gtctcctcag attgattgac tacccacgtc gggggtcttt catttggagg 60
ttccactgag atttggagac ccctgcccag ggaccaccga ccccccgccg ggaggtaagc 120
tggccagcgg tcgtttcgtg tctgtctctg tcttcgtgcg tgtttgtgcc ggcatccaat 180
gtttgcgcct gcgtctgtac tagttagcta actagatctg tatctggcgg ttccgcggaa 240
gaactgacga gttcgtattc ccggccgcag cccctgggag acgtcccagc ggcctcgggg 300
gcccgttttg tggcccattc tgtatcagtt aacctacccg agtcggactt tttggagctc 360
cgccactgta cgtggctttg ttgggggacg agagacagag acacttcccg cccccgtctg 420
aatttttgct ttcggtttta tgccgaaacc gcgccgcgcg tctg 464

<210> SEQ ID NO 95
<211> LENGTH: 466
<212> TYPE: DNA
<213> ORGANISM: Benign prostatic hyperplasia virus

<400> SEQUENCE: 95
ccttgggagg gtctcctcag attgattgac tacccacgtc gggggtcttt catttggagg 60
tcccaccgag atttggagac ccctgcccag ggaccaccga cccccccgcc gggaggtaag 120
ctggccagcg gtcgtttcgt gtctgtctct gtcttcgtgc gtgtttgtgc cggcatccaa 180
tgtttgcgcc tgcgtctgta ctagttagct aactagatct gtatctggcg gttccgcgga 240
agaactgacg agttcgtatt cccggccgca gcccctggga gacgtcccag cggcctcggg 300
ggcccgtttt gtggcccatt ctgtatcagt taacctaccc gagtcggact ttttggagct 360
ccgccactgt acgtggcttt gttgggggac gagaaacaga gacacttccc gcccccgtct 420
gaatttttgc tttcggtttt acgccgaaac cgcgccgcgc gtctga 466

<210> SEQ ID NO 96
<211> LENGTH: 464
<212> TYPE: DNA
<213> ORGANISM: Benign prostatic hyperplasia virus

<400> SEQUENCE: 96
ccttgggagg gtctcctcag attgattgac tacccacgtc gggggtcttt catttggagg 60
tcccaccgag atttggagac ccctgcccag ggaccaccga tcccccgccg ggaggtaagc 120
tggccagcgg tcgtttcgtg tctgtctctg tcttcgtgcg tgtttgtgcc ggcatccaat 180
gtttgcgcct gcgtctgtac tagttagcta actagatctg tatctggcgg ttccgcggaa 240
gaactgacga gttcgtattc ccggccgcag cccctgggag acgtcccagc ggcctcgggg 300
gcccgttttg tggcccattc tgtatcagtt aacctacccg agtcggactt tttggagctc 360
cgccactgta cgtggctttg ttgggggacg agagacagag acacttcccg cccccgtctg 420
aatttttgct ttcggtttta tgccgaaacc gcgccgcgcg tctg 464

<210> SEQ ID NO 97
<211> LENGTH: 464
<212> TYPE: DNA
<213> ORGANISM: Benign prostatic hyperplasia virus

<400> SEQUENCE: 97
ccttgggagg gtctcctcag attgattgac tacccacgtt cgggggtctt tcatttggag 60
gttccaccga gatttggaga cccatgccca gggaccaccg acccccgccg ggaggtaagc 120

```
tggccagcgg tcgtttcgtg tctgtctctg tctccgtgcg tgtttgtgcc ggcatccaat    180
gtttgcgcct gcgtctgtac tagttagcta actagatctg tatctggcgg taccgcggaa    240
gaactgacga gttcgtattc ccggccgcag ccctgggag acgtcccagc ggcctcgggg     300
gcccgttttg tggcccattc tgtatcagtt aacctacccg agtcggactt tttggagctc    360
cgccactgta cgtggctttg ttggggacg agagacagag acacttcccg cccccgtctg     420 aattttttgct ttcggtttta tgccgaaacc gcgccgcgcg tctg                    464
```

<210> SEQ ID NO 98
<211> LENGTH: 470
<212> TYPE: DNA
<213> ORGANISM: Polytropic murine leukemia virus

<400> SEQUENCE: 98

```
gtctcgctgg tccttgagag ggtttcctca aattgattga ctacccacgt cgggggtctt    60
tcatttggag gtcccaccga gatttggaga cccctgccca gggaccaccg accccccgcc    120
gggaggtaag ctggccagcg gtcgtttcgt gtctgtctct gtcttcgtgc gtgtttgtgc    180
cggcatccaa tgtttgcgcc tgcgtctgta ctagttagct aactagatct gtatctggcg    240
gttccgcgga agaactgacg agttcgtatt cccggccgca gccctgggga gacgtcccag    300
cggcctcggg ggcccgtttt gtggcccatt ctgtatcagt taacctaccc gagtcggact    360
ttttggagct ccgccactgt acgtggcttt gttggggac gagaaacaga gacacttccc    420
gcccccgtct gaattttgc tttcggtttt acgccgaagc cgcgccgcgc                 470
```

<210> SEQ ID NO 99
<211> LENGTH: 463
<212> TYPE: DNA
<213> ORGANISM: Benign prostatic hyperplasia virus

<400> SEQUENCE: 99

```
ccttgggagg gtctcctcag attgattgac tgcccacctg ggggtctttt catttggagg    60
tcccaccgag atcaggagac ccctgcccag ggaccaccga ccccgccgg gaggtaagct     120 ggccagcggt cgtttcgtgt ctgtctctgt ctccgtgcgt gtttgtgccg gcatctaatg    180
tttgcgcctg cgtctgtact ggttggctaa ctagatctgt atctggcggt tccgtggaag    240
aactgacgag ttcgtattcc cggccgcagc cctgggaga cgtcccagcg gcctcggggg     300
cccgttttgt ggcccattct gtatcagtta acctacccga gtcggacttt ttggagctcc    360
tccactgtac gtggctttgt cggggacga gaggcagaga cacttcctc cccgtctga     420 attttttgctt tcggttttac gccgaaaccg cgccgcgcgt ctg                     463
```

<210> SEQ ID NO 100
<211> LENGTH: 470
<212> TYPE: DNA
<213> ORGANISM: Benign prostatic hyperplasia virus

<400> SEQUENCE: 100

```
ccttgggagg gtctcctcag attgattgac tacccacctc ggggtctttt catttggagg    60
tcccaccgag attaggagac ccctgcccag ggaccaccga ccccgccgg gaggtaagct     120 ggccagcggt cgtttcgtgt ctgtctctgt ctccgtgcgt gtttgtgccg gcatctaatc    180
tttgcgcctg cgtctgtact agttggctaa ctagatctgt atctggcggt tccgcggaag    240
aactgacgag ttcgtattcc cggccgcagc cctgggagac gtcccagcgg cctcggggc     300
```

```
ccgttttgtg gcccattctg tatcagttaa cctgcccgag tcggattttt ttggagctcc    360
tccactgtcc gagggtacg tggctttgtc ggggacgag aggcagagac acttccctcc     420
cccgtctgaa ttttgcttt cggttttacg ccgaaaccgc gccgcgcgtc               470
```

<210> SEQ ID NO 101
<211> LENGTH: 463
<212> TYPE: DNA
<213> ORGANISM: Benign prostatic hyperplasia virus

<400> SEQUENCE: 101

```
ccttgggagg gtctcctcag attgattgac tgcccacctg gggggtctttt catttggagg    60
ttccaccgag atcaggagac ccctgcccag ggaccaccga cccccgccgg gaggtaagct   120
ggccagcggt cgttttgtgt ctgtctctgt ctccgtgcgt gtttgtgccg gcatctaatg   180
tttgcgcctg cgtctgtact agttggctaa ctagatctgt atctggcggt ttcgcggaag   240
aactgacgag ttcgtattcc cggccgcagc ccctgggaga cgtcccagcg gcctcggggg   300
cccgttttgt ggcccattct gtatcagtta aactacccga gtcggacttt ttggagctcc   360
gccactgtac gtggctttgt tgggggacga gagacagaga cacttcccgc cccgtctgg    420
attttttgctt tcggttttac gccgaaaccg cgccgcgcgt ctg                   463
```

<210> SEQ ID NO 102
<211> LENGTH: 464
<212> TYPE: DNA
<213> ORGANISM: Benign prostatic hyperplasia virus

<400> SEQUENCE: 102

```
ccttgggagg gtctcctcag attgattgac tgcccacctg gggggggtctt tcatttggag     60
gttccaccga gatcaggaga ccctgcccca gggaccaccg accccgccg ggaggtaagc    120
tggccagcgg tcgtttcgtg tctgtctctg tctccgtgcg tgtttgtgcc ggcatctaat    180
gtttgcgcct gcgtctgtac tagttggcta actagatctg tatctggcgg ttcgcggaa     240
gaactgacga gttcgtattc ccggccgcag cccctgggag acgtcccagc ggcctcgggg    300
gcccgttttg tgcccattc tgtatcagtt aacctacccg agtcggactt tttgagctc     360
cgccactgta cgtggctttg ttgggggacg agagacagag acacttcccg ccccgtctg    420
gattttgct tcggttttta cgccgaaacc gcgccgcgcg tctg                     464
```

<210> SEQ ID NO 103
<211> LENGTH: 454
<212> TYPE: DNA
<213> ORGANISM: Benign prostatic hyperplasia virus

<400> SEQUENCE: 103

```
gtctcctcag attgattgac tgcccacctg gggggtctt tcatttggag gttccaccga     60
gatcaggaga ccctgcccca gggaccaccg accccgccg ggaggtaagc tggccagcgg    120
tcgtttcgtg tcagtctctg tctccgtgcg tgtttgtgcc ggcatctaat gtttgcgcct   180
gcgtctgtac tagttggcta actagatctg tatctggcgg tccgcggaa gaactgacga   240
gttcgtattc ccggccgcag cccctgggag acgtcccagc ggcctcgggg gcccgttttg   300
tgcccattc tgtatcagtt aacctacccg agtcggactt tttgagctc cgccactgta    360
cgtggctttg ttgggggacg agagacagag acacttcccg ccccgtctg aattttgct    420
tcggttttta tgccgaaacc gcgccgcgcg tctg                               454
```

<210> SEQ ID NO 104
<211> LENGTH: 470
<212> TYPE: DNA
<213> ORGANISM: Xenotropic murine leukemia virus-related virs

<400> SEQUENCE: 104

```
gcctcgctgt tccttgggag ggtctcctca gagtgattga ctacccagct cggggtctt      60 tcatttgggg gctcgtccgg gattcggaga ccccgccca gggaccaccg acccaccgtc     120
gggaggtaag ccggccggcg atcgttttgt ctttgtctct gtctttgtgc gtgtgtgtgt     180
gtgccggcat ctaatcctcg cgcctgcgtc tgaatctgta ctagttagct aactagatct     240
gtatctggcg gttccgcgga agaactgacg agttcgtatt cccggccgca gccctgggag     300
acgtcccagc ggcctcgggg gcccgttttg tggcccattc tgtatcagtt aacctacccg     360
agtcggactt tttggagtgg ctttgttggg ggacgagaga cagagacact tcccgccccc     420
gtctgaattt ttgctttcgg ttttacgccg aaaccgcgcc gcgcgtctga              470
```

<210> SEQ ID NO 105
<211> LENGTH: 472
<212> TYPE: DNA
<213> ORGANISM: Benign prostatic hyperplasia virus

<400> SEQUENCE: 105

```
ccttgggagg gtctcctcag attgattgac cacccacctc ggggtctttt catttggagg      60
ttccaccgag attaggagac ccctgcccag ggaccaccga ccccgccgg gaggtaagct     120 ggccagcggt cgtttcgtgt ctgtctctgt ctccgtgcgt gtttgtgccg gcatctaatg     180
tttgcgcctg cgtctgtact agttggctaa ctagatctga atctggcggt tccgtggaag     240
aactgacgag ttcatattcc cggccgcagc cctgggagac gtctcagagg catcggggggc     300 catctttgtg gcccaatctg tatctgagaa cccgacccgt ctcggactcc ttggagcctc     360
tcctttgacc gagggatacg tggttctgtt gggcggcgag gggccgaaac gctcctctcc     420
cccatctgaa tttttgcttt cggttttccg ccgaaaccgc gccgcgcgtc tg              472
```

<210> SEQ ID NO 106
<211> LENGTH: 472
<212> TYPE: DNA
<213> ORGANISM: Benign prostatic hyperplasia virus

<400> SEQUENCE: 106

```
ccttgggagg gtctcctcag attgattgac cacccacctc ggggtctttt catttggagg      60
ttccaccgag attaggagac ccctgcccag ggaccaccga ccccgccgg gaggtaagct     120 ggccagcggt cgtttcgtgt ctgtctctgt ctccgtgcgt gtttgtgccg gcatctaatg     180
tttgcgcctg cgtctgtact agttggctaa ctagatctga atctggcggt tccgtggaag     240
aactgacgag ttcatattcc cggccgcagc cctgggagac gtctcagagg catcggggggc     300 catctttgtg gcccaatctg tatctgagaa cccgacccgt ctcggactcc ttggagcctc     360
tcctttgacc gagggatacg tggttctgtt gggcggcgag gggccgaaac gctcctctcc     420
cccatctgaa tttttgcttt cggttttccg ccgaaaccgc gccgcgcgtc tg              472
```

<210> SEQ ID NO 107
<211> LENGTH: 472
<212> TYPE: DNA
<213> ORGANISM: Benign prostatic hyperplasia virus

<400> SEQUENCE: 107

```
ccttgggagg gtctcctcag attgattgac cacccatctc ggggtctttt catttggagg    60
ttccaccgag attaggagac ccctgcccag ggaccaccga ccccgccgg gaggtaagct    120 ggccagcggt cgtttcgtgt ctgtctctgt ctccgtgcgt gtttgtgccg gcatctaatg    180
tttgcgcctg cgtctgtact agttggctaa ctagatctga atctggcggt tccgtggaag    240
aactgacgag ttcatattcc cggccgcagc cctgggagac gtctcagagg catcgggggc    300
catctttgtg gcccaatctg tatctgagaa cccgacccgt ctcggactcc ttggagcctc    360
tcctttgacc gagggatacg tggttctgtt gggcggcgag gggccgaaac gctcctctcc    420
cccatctgaa tttttgcttt cggttttccg ccgaaaccgc gccgcgcgtc tg             472
```

<210> SEQ ID NO 108
<211> LENGTH: 472
<212> TYPE: DNA
<213> ORGANISM: Benign prostatic hyperplasia virus

<400> SEQUENCE: 108

```
ccttgggagg gtctcctcag attgattgac cacccacctc ggggtctttt catttggagg    60
ttccaccgag attaggagac ccctgcccag ggaccaccga ccccgccgg gaggtaagct    120 ggccagcggt cgtttcgtgt ctgtctctgt ctccgtgcgt gtttgtgccg gcatctaatg    180
tttgcgcctg cgtctgtact agttggctaa ctagatctga atctggcggt tccgtggaag    240
aactgacgag ttcatattcc cggccgcagc cctgggagac gtctcagagg catcgggggc    300
catctttgcg gcccaatctg tatctgagaa cccgacccgt ctcggactcc ttggagcctc    360
tcctttgacc gagggatacg tggttctgtt gggcggcgag gggccgaaac gctcctctcc    420
cccatctgaa tttttgcttt cggttttccg ccgaaaccgc gccgcgcgtc tg             472
```

<210> SEQ ID NO 109
<211> LENGTH: 472
<212> TYPE: DNA
<213> ORGANISM: Benign prostatic hyperplasia virus

<400> SEQUENCE: 109

```
ccttgggagg gtctcctcag attgattgac cacccacctc ggggtctttt catttggagg    60
ttccaccgag attaggagac ccctgcccag ggaccaccga ccccgccgg gaggtaagct    120 ggccagcggt cgtttcgtgt ctgtctctgt ctccgcgcgt gtttgtgccg gcatctaatg    180
tttgcgcctg cgtctgtact agttggctaa ctagatctga atctggcggt tccgtggaag    240
aactgacgag ttcatattcc cggccgcagc cctgggagac gtctcagagg catcgggggc    300
catctttgtg gcccaatctg tatctgagaa cccgacccgt ctcggactcc ttggagcctc    360
tcctttgacc gagggatacg tggttctgtt gggcggcgag gggccgaaac gctcctctcc    420
cccatctgaa tttttgcttt cggttttccg ccgaaaccgc gccgcgcgtc tg             472
```

<210> SEQ ID NO 110
<211> LENGTH: 470
<212> TYPE: DNA
<213> ORGANISM: Benign prostatic hyperplasia virus

<400> SEQUENCE: 110

```
gtctcgctga tccttgggag gtctcctca gattgattga ccacccacct cggaggtctt    60
tcatttggag gycccascga gattaggaga ccctgcccca gggaccaccg accccgccg    120 ggaggtaagc tggccagcgg tcgtttcgtg tctgtctctg tctccgtgcg tgttcgtgcc    180
ggcatctaat gtttgcgcct gcgtctgtac tagttggcta actagatctg aatctggcgg    240
```

```
ttccgtggaa gaactgacga gttcatattc ccggccgcag ccctgggaga cgtctcagag    300
gcatcggggg ccatctttgt ggcccaatct gtatctgaga acccgacccg tctcggactc    360
tttggagcct ctcctttgac cgagggatac gtggttctgt tgggcggcga ggggccgaaa    420
cgctcctctc ccccatctga attttttgttt tcggttttcc gccgaaaccg              470

<210> SEQ ID NO 111
<211> LENGTH: 476
<212> TYPE: DNA
<213> ORGANISM: Benign prostatic hyperplasia virus

<400> SEQUENCE: 111
ccttgggagg gtctcctcag attgattgac tacccaccgc gggggtcttc catttggagg     60
tcccaccgag attaggagac ccctgcccag ggaccaccga ccccgccgg gaggtaagct    120 ggccagcggt cgtttcgtgt ctgtctctgt ctccgtgcgt gttgcgtgtt tgtgccggca    180
tctaatgttt gcgcctgcgt ctgtactagt tagctaacta gatctgaatc tggcggttcc    240
gtggaagaac tgacgagttc atattcccgg ccgcagccct gggagacgtc tcagaggcat    300
cgggggccat ctttgtggcc caatctgtat ctgagaaccc gacccgtctc ggactctttg    360
gagcctctcc tttgaccgag ggatacgtgg ttctgttggg cggcgagggg ccgaaacgct    420
cctccccccc catctgaatt tttgctttcg gttttccgcc gaaaccgcgc cgcgcg        476

<210> SEQ ID NO 112
<211> LENGTH: 480
<212> TYPE: DNA
<213> ORGANISM: Benign prostatic hyperplasia virus

<400> SEQUENCE: 112
ccttgggagg gtctcctcag attgattgac tacccaccgc gggggtcttt catttggagg     60
tcccaccgag attaggagac ccctgcccag ggaccaccga ccccgccgg gaggtaagct    120 ggccagcggt cgtttcgtgt ctgtctctgt ctccgtgcgt gttgcgtgtt tgtgccggca    180
tctaatgttt gcgcctgcgt ctgtactagt tagctaacta gatctgaatc tggcggttcc    240
gtggaagaac tgacgagttc atattcccgg ccgcagccct gggagacgtc tcagaggcat    300
cgggggccat ctttgtggcc caatctgtat ctgagaaccc gacccgtctc ggactctttg    360
gagcctctcc tttgaccgag ggatacgtgg ttctgttggg cggcgagggg ccgaaacgct    420
cctccccccc catctgaatt tttgctttcg gttttccgcc gaaaccgcgc cgcgcgtccg    480

<210> SEQ ID NO 113
<211> LENGTH: 480
<212> TYPE: DNA
<213> ORGANISM: Benign prostatic hyperplasia virus

<400> SEQUENCE: 113
ccttgggagg gtctcctcag attgattgac tacccaccgc gggggtcttt catttggagg     60
tcccaccgag attaggagac ccctgcccag ggaccaccga ccccgccgg gaggtaagct    120 ggccagcggt cgtttcgtgt ctgtctctgt ctccatgcgt gttgcgtgtt tgtgccggca    180
tctaatgttt gcgcctgcgt ctgtactagt tagctaacta gatctgaatc tggcggttcc    240
gtggaagaac tgacgagttc atattcccgg ccgcagccct gggagacgtc tcagaggcat    300
cgggggccat ctttgtggcc caatctgtat ctgagaaccc gacccgtctc ggactctttg    360
gagcctctcc tttgaccgag ggatacgtgg ttctgttggg cggcgagggg ccgaaacgct    420
```
cctccccccc catctgaatt tttgctttcg gttttccgcc gaaaccgcgc cgcgcgtctg        480

<210> SEQ ID NO 114
<211> LENGTH: 501
<212> TYPE: DNA
<213> ORGANISM: Benign prostatic hyperplasia virus

<400> SEQUENCE: 114
ccttgggagg gtctcctcag attgattgac tacccaccgc ggggtctttt catttggagg         60
tcccaccgag attaggagac ccctgcccag ggaccaccga cccccgccgg gaggtaagct        120
ggccagcggt cgtttcgtgt ctgtctctgt ctccgtgcgt gttgcgtgtt tgtgccggca        180
tctaatgttt gcgcctgcgt ctgtactagt tagctaacta gatctgaatc tggcggttcc        240
gtggaagaac tgacgagttc atattcccgg ccgcagccct gggagacgtc tcagaggcat        300
cgggggccat ctttgtggcc caatctgtat ctgagaaccc gacccgtctc ggactctttg        360
gagcctctcc tttgaccgag ggatacgtgg ttctgtcggg cggcgagggg ccgaagcgct        420
cctccccccc catctgaatt tttgctttcg gttttccgcc gaaaccgcgc cgcgcgtctg        480
acctccttgg gagggtctcc t                                                  501

<210> SEQ ID NO 115
<211> LENGTH: 470
<212> TYPE: DNA
<213> ORGANISM: Murine AIDS-like virus

<400> SEQUENCE: 115
agctctcaaa agttacaagg aagttcagtt aaagattaac agttacaaat caaggctgaa         60
taatactagg acaagggcca aacaggatat cggtggtcaa gcgcctgggc cccggctcag        120
ggccaagaac agatggtacc cagataaagc ggaaccagca acagtttctg aaaaagtccc        180
acctcagttt caggttcccc aaatgaccag gaaataccec aagccttgat ttgaactaac        240
cactcagctc gcttctcgct tctgtacccg cgctttttgc tccccagccc cagccctata        300
aaaagggtaa gaactccaca ctcggcgcgc cagtcctccg acagactgag tcgcccgggt        360
acccgtgttc ccaataaagc ctcttgctga ttacatccga atcgtggtct cgctgatcct        420
tgggagggtc tcctcagatt gattgaccac ccacctcggg ggtctttcat                   470

<210> SEQ ID NO 116
<211> LENGTH: 132
<212> TYPE: PRT
<213> ORGANISM: Murine leukemia virus

<400> SEQUENCE: 116

Gly Thr Met Thr Asp Thr Phe Pro Lys Leu Tyr Phe Asp Leu Cys Asp
1               5                   10                  15

Leu Val Gly Asp Tyr Trp Asp Asp Pro Glu Pro Asp Ile Gly Asp Gly
            20                  25                  30

Cys Arg Thr Pro Gly Gly Arg Arg Thr Arg Leu Tyr Asp Phe Tyr
        35                  40                  45

Val Cys Pro Gly His Thr Val Pro Ile Gly Cys Gly Gly Pro Gly Glu
    50                  55                  60

Gly Tyr Cys Gly Lys Trp Gly Cys Glu Thr Thr Gly Gln Ala Tyr Trp
65                  70                  75                  80

Lys Pro Ser Ser Ser Trp Asp Leu Ile Ser Leu Lys Arg Gly Asn Thr
                85                  90                  95

Pro Lys Asp Gln Gly Pro Cys Tyr Asp Ser Ser Val Ser Ser Gly Val

```
              100                 105                 110
Gln Gly Ala Thr Pro Gly Gly Arg Cys Asn Pro Leu Val Leu Glu Phe
        115                 120                 125

Thr Asp Ala Gly
        130

<210> SEQ ID NO 117
<211> LENGTH: 132
<212> TYPE: PRT
<213> ORGANISM: Murine leukemia virus

<400> SEQUENCE: 117

Gly Thr Met Thr Asp Thr Phe Pro Lys Leu Tyr Phe Asp Leu Cys Asp
1               5                   10                  15

Leu Val Gly Asp His Trp Asp Asp Pro Glu Pro Asp Ile Gly Asp Gly
            20                  25                  30

Cys Arg Ser Pro Gly Gly Arg Lys Arg Thr Arg Leu Tyr Asp Phe Tyr
        35                  40                  45

Val Cys Pro Gly His Thr Val Pro Ile Gly Cys Gly Gly Pro Gly Glu
    50                  55                  60

Gly Tyr Cys Gly Lys Trp Gly Cys Glu Thr Thr Gly Gln Ala Tyr Trp
65                  70                  75                  80

Lys Pro Ser Ser Ser Trp Asp Leu Ile Ser Leu Lys Arg Gly Asn Thr
                85                  90                  95

Pro Lys Asp Gln Gly Pro Cys Tyr Asp Ser Ser Val Ser Ser Gly Val
            100                 105                 110

Gln Gly Ala Thr Pro Gly Gly Arg Cys Asn Pro Leu Val Leu Glu Phe
        115                 120                 125

Thr Asp Ala Gly
        130

<210> SEQ ID NO 118
<211> LENGTH: 133
<212> TYPE: PRT
<213> ORGANISM: Xenotropic murine leukemia virus-related virus

<400> SEQUENCE: 118

Gly Thr Met Thr Asp Thr Phe Pro Lys Leu Tyr Phe Asp Leu Cys Asp
1               5                   10                  15

Leu Val Gly Asp Asn Trp Asp Asp Pro Glu Pro Asp Ile Gly Asp Gly
            20                  25                  30

Cys Arg Ser Pro Gly Gly Arg Lys Arg Thr Arg Leu Tyr Asp Phe Tyr
        35                  40                  45

Val Cys Pro Gly His Thr Val Leu Thr Gly Cys Gly Gly Pro Arg Glu
    50                  55                  60

Gly Tyr Cys Gly Lys Trp Gly Cys Glu Thr Thr Gly Gln Ala Tyr Trp
65                  70                  75                  80

Lys Pro Ser Ser Ser Trp Asp Leu Ile Ser Leu Lys Arg Gly Asn Thr
                85                  90                  95

Pro Lys Gly Gln Gly Pro Cys Phe Asp Ser Ser Val Gly Ser Gly Ser
            100                 105                 110

Ile Gln Gly Ala Thr Pro Gly Gly Arg Cys Asn Pro Leu Val Leu Glu
        115                 120                 125

Phe Thr Asp Ala Gly
            130
```

```
<210> SEQ ID NO 119
<211> LENGTH: 133
<212> TYPE: PRT
<213> ORGANISM: Murine leukemia virus

<400> SEQUENCE: 119
```

Gly Thr Met Thr Asp Thr Phe Pro Lys Leu Tyr Phe Asp Leu Cys Asp
1               5                   10                  15

Leu Val Gly Asp Tyr Trp Asp Pro Glu Ser Ser Ile Gly His Gly
                20                  25                  30

Cys Arg Ser Pro Gly Gly Arg Lys Arg Thr Arg Thr Phe Asp Phe Tyr
            35                  40                  45

Val Cys Pro Gly His Thr Val Leu Thr Gly Cys Gly Gly Pro Arg Glu
    50                  55                  60

Gly Tyr Cys Gly Lys Trp Gly Cys Glu Thr Thr Gly Gln Ala Tyr Trp
65                  70                  75                  80

Lys Pro Ser Ser Ser Trp Asp Leu Ile Ser Leu Lys Arg Gly Asn Thr
                85                  90                  95

Pro Lys Gly Gln Gly Pro Cys Tyr Asp Ser Ser Val Val Ser Ser Ser
                100                 105                 110

Ile Gln Gly Ala Thr Pro Gly Arg Cys Asn Pro Leu Val Leu Glu
            115                 120                 125

Phe Thr Asp Ala Gly
        130

```
<210> SEQ ID NO 120
<211> LENGTH: 129
<212> TYPE: PRT
<213> ORGANISM: Mink cell focus-forming murine leukemia virus

<400> SEQUENCE: 120
```

Gly Thr Met Thr Asp Ala Phe Pro Lys Leu Tyr Phe Asp Leu Cys Asp
1               5                   10                  15

Leu Ile Gly Asp Asp Trp Asp Glu Thr Gly Leu Gly Cys Arg Thr Pro
                20                  25                  30

Gly Gly Arg Lys Arg Ala Arg Thr Phe Asp Phe Tyr Val Cys Pro Gly
            35                  40                  45

His Thr Val Pro Thr Gly Cys Gly Gly Pro Arg Glu Gly Tyr Cys Gly
    50                  55                  60

Lys Trp Gly Cys Glu Thr Thr Gly Gln Ala Tyr Trp Lys Pro Ser Ser
65                  70                  75                  80

Ser Trp Asp Leu Ile Ser Leu Lys Arg Gly Asn Thr Pro Gln Asn Gln
                85                  90                  95

Gly Pro Cys Tyr Asp Ser Ser Ala Val Ser Ser Asp Ile Lys Gly Ala
                100                 105                 110

Thr Pro Gly Gly Arg Cys Asn Pro Leu Val Leu Glu Phe Thr Asp Ala
            115                 120                 125

Gly

```
<210> SEQ ID NO 121
<211> LENGTH: 129
<212> TYPE: PRT
<213> ORGANISM: Friend mink cell focus-forming virus

<400> SEQUENCE: 121
```

Gly Thr Met Thr Asp Ala Phe Pro Met Leu Tyr Phe Asp Leu Cys Asp
1               5                   10                  15

```
Leu Ile Gly Asp Asp Trp Asp Glu Thr Gly Leu Gly Cys Arg Thr Pro
        20                  25                  30

Gly Gly Arg Lys Arg Ala Arg Thr Phe Asp Phe Tyr Val Cys Pro Gly
            35                  40                  45

His Thr Val Pro Thr Gly Cys Gly Gly Pro Arg Glu Gly Tyr Cys Gly
        50                  55                  60

Lys Trp Gly Cys Glu Thr Thr Gly Gln Ala Tyr Trp Lys Pro Ser Ser
65                  70                  75                  80

Ser Trp Asp Leu Ile Ser Leu Lys Arg Gly Asn Thr Pro Arg Asn Gln
                85                  90                  95

Gly Pro Cys Tyr Asp Ser Ser Val Val Ser Ser Gly Ile Gln Gly Ala
            100                 105                 110

Thr Pro Gly Gly Arg Cys Asn Pro Leu Val Leu Glu Phe Thr Asp Ala
            115                 120                 125

Gly
```

<210> SEQ ID NO 122
<211> LENGTH: 17
<212> TYPE: DNA
<213> ORGANISM: Benign prostatic hyperplasia virus

<400> SEQUENCE: 122
aagaacagat ggctctc                                                    17

<210> SEQ ID NO 123
<211> LENGTH: 17
<212> TYPE: DNA
<213> ORGANISM: Benign prostatic hyperplasia virus

<400> SEQUENCE: 123
aagaacagat ggtaccc                                                    17

<210> SEQ ID NO 124
<211> LENGTH: 17
<212> TYPE: DNA
<213> ORGANISM: Benign prostatic hyperplasia virus

<400> SEQUENCE: 124
aagaaccgat ggtaccc                                                    17

<210> SEQ ID NO 125
<211> LENGTH: 17
<212> TYPE: DNA
<213> ORGANISM: Benign prostatic hyperplasia virus

<400> SEQUENCE: 125
aagaacagat ggtcccc                                                    17

<210> SEQ ID NO 126
<211> LENGTH: 15
<212> TYPE: DNA
<213> ORGANISM: Artificial Sequence
<220> FEATURE:
<223> OTHER INFORMATION: androgen response element consensus sequence
<220> FEATURE:
<221> NAME/KEY: misc_feature
<222> LOCATION: (7)..(9)
<223> OTHER INFORMATION: n is a, c, g, or t

<400> SEQUENCE: 126
agaacannnt gttct                                                      15